(12) United States Patent
Divakaruni et al.

(10) Patent No.: US 11,813,277 B2
(45) Date of Patent: Nov. 14, 2023

(54) METHODS AND AGENTS FOR MODULATING INFLAMMATION

(71) Applicant: The Regents of the University of California, Oakland, CA (US)

(72) Inventors: Ajit Srinivas Divakaruni, Los Angeles, CA (US); Steven J. Bensinger, Sherman Oaks, CA (US); Anne Neville Murphy, Encinitas, CA (US); Wei Yuan Hsieh, Los Angeles, CA (US)

(73) Assignee: THE REGENTS OF THE UNIVERSITY OF CALIFORNIA, Oakland, CA (US)

( * ) Notice: Subject to any disclaimer, the term of this patent is extended or adjusted under 35 U.S.C. 154(b) by 231 days.

(21) Appl. No.: 17/252,962

(22) PCT Filed: Jun. 27, 2019

(86) PCT No.: PCT/US2019/039454
§ 371 (c)(1),
(2) Date: Dec. 16, 2020

(87) PCT Pub. No.: WO2020/006199
PCT Pub. Date: Jan. 2, 2020

(65) Prior Publication Data
US 2021/0128599 A1  May 6, 2021

Related U.S. Application Data

(60) Provisional application No. 62/690,732, filed on Jun. 27, 2018.

(51) Int. Cl.
A01N 43/04    (2006.01)
A61K 31/70    (2006.01)
A61K 31/7064  (2006.01)
A61K 45/06    (2006.01)

(52) U.S. Cl.
CPC .......... *A61K 31/7064* (2013.01); *A61K 45/06* (2013.01)

(58) Field of Classification Search
None
See application file for complete search history.

(56) References Cited

U.S. PATENT DOCUMENTS 3,819,830 A      6/1974   Yoshimura et al.
2010/0028319 A1  2/2010   Sakamoto et al.

FOREIGN PATENT DOCUMENTS

WO  WO 2008/007728  1/2008
WO  WO 2017/048322  3/2017

OTHER PUBLICATIONS

Leonardi et al. Progress in Lipid Research (2005), vol. 44, pp. 125-153.*
International Search Report and Written Opinion, dated Jan. 7, 2020, from corresponding International Application No. PCT/US19/39454, filed Jun. 27, 2019.
Stienstra et al., "Peroxisome Proliferator-activated Receptor γ Activation Promotes Infiltration of Alternatively Activated Macrophages into Adipose Tissue", Journal of Biological Chemistry, Aug. 15, 2008, 283(33): 22620-22627.
Musselman et al., "CoA protects against the deleterious effects of caloric overload in *Drosophila*", Journal of Lipid Research, Jan. 24, 2016, vol. 57, pp. 380-387.
Roberts et al., "The contrasting roles of PPARδ and PPARγ in regulating the metabolic switch between oxidation and storage of fat in white adipose tissue", Genome Biology, Aug. 11, 2011, vol. 12, No. 8, pp. 1-19.
Mauer et al., "Interleukin-6 signaling promotes alternative macrophage activation to limit obesity-associated insulin resistance and endotoxemia", Nature Immunology, May 2014, Epub Mar. 30, 2014, vol. 15, No. 5, pp. 423-430.
Odegaard et al., "Mechanisms of macrophage activation in obesity-induced insulin resistance", Nature Clinical Practice: Endocrinology and Metabolism, Nov. 2008, Epub Oct. 7, 2008, 4(11): 619-626.
Covarrubias et al., "Akt-mTORC1 signaling regulates Acly to integrate metabolic input to control of macrophage activation", eLife, Feb. 19, 2016, vol. 5, pp. 1-19.
Sharma et al., "A High-Throughput Screen Reveals New Small-Molecule Activators and Inhibitors of Pantothenate Kinases", Journal of Medical Chemistry, 2015, 58, 1563-1568.
Berge et al., "Pharmaceutical Salts", J. Pharmaceutical Sciences, 66: 1-19 (1977).
Rautio et al., "Prodrugs: design and clinical applications", Nature Reviews Drug Discovery, Mar. 2008, vol. 7, pp. 255-270.
Takeshita et al., "Identification and Characterization of the New Osteoclast Progenitor with Macrophage Phenotypes Being Able to Differentiate into Mature Osteoclasts", Journal of Bone and Mineral Research, 2000, 15(8): 1477-1488.
Schoors et al., "Fatty acid carbon is essential for dNTP synthesis in endothelial cells", Nature, Apr. 9, 2015, 520(7546): 192-197.
Gonzalez-Hurtado et al., "Loss of macrophage fatty acid oxidation does not potentiate systemic metabolic dysfunction", Am. J. Physiol. Endocrinol. Metab. 312: E381-E393 (2017).
Nomura et al., "Fatty acid oxidation in macrophage polarization", Nature Immunology, 17, 216-217 (2016).
Kushnareva et al., "Excitotoxic Injury to Mitochondria Isolated from Cultured Neurons", The Journal of Biological Chemistry, 280(32): 28894-28902, Aug. 12, 2005.

(Continued)

*Primary Examiner* — Patrick T Lewis
(74) *Attorney, Agent, or Firm* — Mark S. Cohen; PEARL COHEN ZEDEK LATZER BARATZ LLP

(57) ABSTRACT

Methods and agents for modulating intracellular coenzyme A levels are described for therapeutic purposes. Increasing intracellular coenzyme A increases alternate macrophage activation resulting in suppression or resolution of an immune response for benefit in treating inflammatory diseases. Decreasing intracellular coenzyme A levels decreases alternate macrophage activation which is beneficial in treating NASH/NAFLD and various fibrotic diseases as well as reversing immune suppressing activity of tumor-associated immune cells such as macrophages for the treatment of cancer.

2 Claims, 60 Drawing Sheets

Specification includes a Sequence Listing.

(56) References Cited

OTHER PUBLICATIONS

Rubio et al., "Cardioprotective Stimuli Mediate Phosphoinositide 3-Kinase and Phosphoinositide Dependent Kinase 1 Nuclear Accumulation in Cardiomyocytes", J. Mo.l Cell. Cardiol., Jul. 2009; 47(1): 96-103.
Rogers et al.,"High Throughput Microplate Respiratory Measurements Using Minimal Quantities Of Isolated Mitochondria", PLoS One, Jul. 2011, 6(7): e21746.
Divakaruni et al., "Thiazolidinediones are acute, specific inhibitors of the mitochondrial pyruvate carrier", Proc. Natl. Acad. Sci., Apr. 2, 2013, 110(14): 5422-5427.
Divakaruni et al., "In situ measurements of mitochondrial matrix enzyme activities using plasma and mitochondrial membrane permeabilization agents", Anal. Biochem., Jul. 1, 2018, 17(552): 60-65.
McQuaker et al., "A Prototypical Small-Molecule Modulator Uncouples Mitochondria in Response to Endogenous Hydrogen Peroxide Production", ChemBioChem., 2013, 14, 993-1000.
Mookerjee et al., "The contributions of respiration and glycolysis to extracellular acid production", Biochimica et Biophysica Acta, 1847 (2015) 171-181.
Rognstad, "Estimation of peroxisomal and mitochondrial fatty acid oxidation in rat hepatocytes using tritiated substrates", Biochem. J. (1991) 279:147-150.
Cha et al., "Impaired fatty acid metabolism in type 2 diabetic skeletal muscle cells is reversed by PPARγ agonists", Am. J. Physiol. Endocrinol. Metab., 289: E151-E159, Jul. 2005.
Divakaruni et al., "Inhibition of the mitochondrial pyruvate carrier protects from excitotoxic neuronal death", J. Cell Biol., 2017, 216(4): 1091-1105.
Xiao et al., "B-Cell-Specific Diversion of Glucose Carbon Utilization Reveals a Unique Vulnerability in B Cell Malignancies", Cell, 173, 470-484, Apr. 5, 2018.
Chen et al., "Rapid immunopurification of mitochondria for metabolite profiling and absolute quantification of matrix metabolites", Nat. Protoc., Oct. 2017, 12(10): 2215-2231.
Hui et al., "The Genetic Architecture of Diet-induced Hepatic Fibrosis in Mice", Hepatology, Dec. 2018, 68(6): 2182-2196.
Carroll et al., "An unexpected link between fatty acid synthase and cholesterol synthesis in proinflammatory macrophage activation", J. Biol. Chem. (2018) 293(15): 5509-5521.
International Preliminary Report on Patentability, dated Jan. 7, 2021, from corresponding International Patent Application No. PCT/US2019/039454.
Huang et al., "Cell-intrinsic lysosomal lipolysis is essential for macrophage alternative activation", Nat. Immunol., Sep. 2014, 15(9): 846-855.
Jordan et al., "Synthesis and Analysis of Urea and Carbamate Prodrugs as Candidates for Melanocyte-Directed Enzyme Prodrug Therapy (MDEPT)", Bioorganic & Medicinal Chemistry, 10 (2002) pp. 2625-2633.
Hay et al., "Synthesis and Evaluation of Nitroheterocyclic Carbamate Prodrugs for Use with Nitroreductase-Mediated Gene-Directed Enzyme Prodrug Therapy", Journal of Medicinal Chemistry, 2003, 46(25): 5533-5545.
Caton et al., "Notch-RBP-J signaling controls the homeostasis of CD8-dendritic cells in the spleen", Journal of Experimental Medicine, Jul. 9, 2007, 204(7):1653-1664.
Clausen et al., "Conditional gene targeting in macrophages and granulocytes using LysMcre mice", Transgenic Research 8: 265-277, 1999.
Kim et al., "Isolation and Culture of Neurons and Astrocytes from the Mouse Brain Cortex", Neurodegeneration: Methods and Protocols, Methods in Molecular Biology, (2011) vol. 793, pp. 63-75.
Divakaruni et al., "Analysis and Interpretation of Microplate-Based Oxygen Consumption and pH Data", Methods in Enzymology (2014), vol. 547, pp. 309-354.
Rogers et al., "Assessment of Fatty Acid Beta Oxidation in Cells and Isolated Mitochondria", Current Protocols in Toxicology, 25.3. 1-25.3.19, May 2014.
Divakaruni et al., "Measuring Mitochondrial Function in Permeabilized Cells Using the Seahorse XF Analyzer or a Clark-Type Oxygen Electrode", Current Protocols in Toxicology, 25.2.1-25.2.16, May 2014.
Coty et al., "Phosphate Transport in Rat Liver Mitochondria* Kinetics, Inhibitor Sensitivity, Energy Requirements, and Labelled Components", Molecular & Cellular Biochemistry, Nov. 30, 1975, 9(2): 109-124.
Klingenberg et al., "Analysis of the Reactivity of SH-Reagents with the Mitochondrial Phosphate Carrier", Eur. J. Biochem. 42, 135-150 (1974).
Paradies et al., "Effect of Aging on the Activity of the Phosphate Carrier and on the Lipid Composition in Rat Liver Mitochondria", Archives of Biochemistry and Biophysics, Feb. 1, 1991, 284(2): 332-337.

* cited by examiner

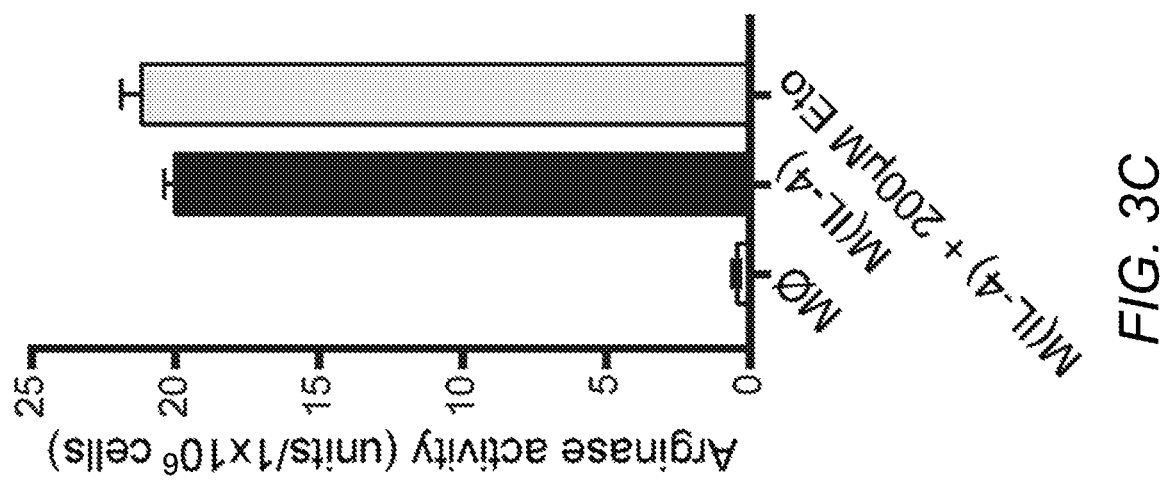

SEQUENCE LISTING

```
<160> NUMBER OF SEQ ID NOS: 10

<210> SEQ ID NO 1
<211> LENGTH: 21
<212> TYPE: DNA
<213> ORGANISM: Rattus norvegicus

<400> SEQUENCE: 1
tcgtggagaa taaggtcaag g                                          21

<210> SEQ ID NO 2
<211> LENGTH: 20
<212> TYPE: DNA
<213> ORGANISM: Rattus norvegicus

<400> SEQUENCE: 2
aggaggccca tctgttcata                                            20

<210> SEQ ID NO 3
<211> LENGTH: 20
<212> TYPE: DNA
<213> ORGANISM: Rattus norvegicus

<400> SEQUENCE: 3
aggcacccta agagccattt                                            20

<210> SEQ ID NO 4
<211> LENGTH: 20
<212> TYPE: DNA
<213> ORGANISM: Rattus norvegicus

<400> SEQUENCE: 4
ccctcttctc cagtgtgctc                                            20

<210> SEQ ID NO 5
<211> LENGTH: 20
<212> TYPE: DNA
<213> ORGANISM: Rattus norvegicus

<400> SEQUENCE: 5
taagactgga attggtgccc                                            20

<210> SEQ ID NO 6
<211> LENGTH: 20
<212> TYPE: DNA
<213> ORGANISM: Rattus norvegicus

<400> SEQUENCE: 6
taagactgga attggtgccc                                            20

<210> SEQ ID NO 7
<211> LENGTH: 20
<212> TYPE: DNA
<213> ORGANISM: Rattus norvegicus
```

```
<400> SEQUENCE: 7
ggatggaaag tcgaccacaa                                           20

<210> SEQ ID NO 8
<211> LENGTH: 20
<212> TYPE: DNA
<213> ORGANISM: Rattus norvegicus

<400> SEQUENCE: 8
tggaagtcac gcctttcata                                           20

<210> SEQ ID NO 9
<211> LENGTH: 21
<212> TYPE: DNA
<213> ORGANISM: Rattus norvegicus

<400> SEQUENCE: 9
ctgtgccagc tcagaacact g                                         21

<210> SEQ ID NO 10
<211> LENGTH: 20
<212> TYPE: DNA
<213> ORGANISM: Rattus norvegicus

<400> SEQUENCE: 10
tgatcagccc gaaggagaag                                           20
```

METHODS AND AGENTS FOR MODULATING INFLAMMATION

CROSS-REFERENCE TO RELATED APPLICATIONS

This application is a National Phase Application of PCT International Application No. PCT/US19/39454, International Filing Date Jun. 27, 2019, claiming the benefit of U.S. Provisional Patent Application No. 62/690,732, filed Jun. 27, 2018, which is hereby incorporated by reference.

GOVERNMENT SUPPORT

This invention was made with government support under Grant Numbers AI122282 and NS087611, awarded by the National Institutes of Health. The government has certain rights in the invention.

BACKGROUND OF THE INVENTION

Macrophages are innate immune cells responsible for a broad range of processes such as detecting and killing pathogens, clearing apoptotic cells and subcellular debris, initiating wound-healing programs, and presenting antigens to T cells. To achieve these different functions, macrophages possess the capacity to acquire pro- and anti-inflammatory programs in response to extrinsic signals. Accumulating evidence indicates that alterations in cellular metabolism are critical for supporting these varied roles. For example, activation of Toll-like receptor 4 signaling with the pro-inflammatory stimulus lipopolysaccharide (LPS) results in profound changes to both glycolytic and mitochondrial metabolism. Flux through glycolysis and the pentose phosphate pathway are substantially increased to support energy metabolism, anabolism, and cytoplasmic NADPH production, while oxidative phosphorylation is inhibited, presumably to reprogram mitochondria for the production of pro-inflammatory metabolites and redox signals. Conversely, macrophages differentiated with the anti-inflammatory cytokine interleukin 4 (IL-4) (±IL-13) induce transcriptional programs associated with mitochondrial biogenesis and oxidative mitochondrial metabolism.

Importantly, genetic inhibition of these metabolic pathways attenuates the acquisition of effector responses. This demonstrates a fundamental role for metabolism in macrophage function and informs the hypothesis that pharmacologically targeting these pathways can influence macrophage biology. In particular, the acquisition of anti-inflammatory phenotypes and/or wound healing functions can be inhibited by perturbing the reprogramming of oxidative metabolism. However, it remains unclear precisely which metabolic pathways or signals governed by these larger transcriptional programs are indispensable for (rather than merely associated with) IL-4-induced alternative macrophage activation.

It is well accepted that differentiation of macrophages with IL-4 [referred to herein as M(IL-4) polarization, alternative activation, alternative macrophage activation, anti-inflammatory macrophage activation, and related terms] is associated with enhanced fatty acid oxidation. Long-chain fatty acid (LCFA) oxidation is demonstrably increased in macrophages upon IL-4 stimulation, and PPARγ, a nuclear receptor controlling gene expression for lipid metabolism-related genes, is associated with and essential for alternative macrophage activation. Whether LCFA oxidation is obligatory for M(IL-4) polarization, though, remains controversial. Supportive evidence comes largely from studies using etomoxir, an inhibitor of carnitine palmitoyl transferase-1 (CPT-1). CPT-1 is a mitochondrial outer membrane enzyme that conjugates long chain fatty acyl coenzyme As (CoAs) to carnitine and facilitates uptake into the mitochondrial matrix for oxidation.

Etomoxir is a small molecule developed for metabolic and cardiovascular disease that exhibits nanomolar potency towards CPT-1a and CPT-1b upon enzymatic conversion to the active inhibitor etomoxiryl CoA (IC50=0.01-0.70 μM). Therefore, the specificity of etomoxir at 200 μM, a concentration frequently used to elicit inhibition of alternative macrophage activation, has been questioned. For example, multiple studies have shown that lower concentrations of etomoxir (10 μM and 100 μM) fail to affect IL-4-associated markers. Similar to pharmacologic inhibition of CPT-1, genetic studies have also yielded inconclusive results. Although viral knockdown of Cpt1a reduced expression of IL-4-associated cell surface markers, an integrative systems approach merging metabolomics and transcriptomics indicated Cpt1 expression is more closely associated with pro-inflammatory macrophage polarization rather than an anti-inflammatory program. Moreover, myeloid-specific knockout of Cpt2, the enzyme required to convert fatty acyl carnitines back to fatty acyl CoAs in the mitochondrial matrix, does not impair macrophage differentiation in vitro or in vivo despite significant reductions in LCFA oxidation. When used at 200 μM, etomoxir was equally effective in blocking M(IL-4) polarization in Cpt2−/− bone marrow-derived macrophages (BMDMs) as in wild-type (WT) cells. This aligns with literature suggesting etomoxir may have CPT-1-independent effects on metabolism at high concentrations, including inhibition of mitochondrial complex I.

It is towards a means for modulating alternate macrophage activation for therapeutic benefit in various diseases and conditions that the present invention is directed.

BRIEF SUMMARY OF THE INVENTION

In one embodiment, a method is provided for increasing alternative macrophage activation in a subject by administering an agent that increases intracellular coenzyme A levels. In one embodiment, increasing alternative macrophage activation suppresses or resolves an immune response in the subject. In one embodiment, the immune response occurs in a disease or condition selected from diet-induced obesity, inflammation-related metabolic disorders, metabolic syndrome, sepsis, rheumatoid arthritis, eczemas, allergic or atopic dermatitis, and an inflammatory condition of the eye. In one embodiment, the suppression or resolution of the immune response promotes tissue repair, wound healing, repair of skin damage from burns, sunburn or radiation damage. In one embodiment, increasing alternative macrophage activation suppresses or treats a parasitic infection.

In one embodiment, the agent that increases alternative macrophage activation is coenzyme A or an active analogue thereof, or where the agent increases biosynthesis of coenzyme A. In one embodiment the agent is pantothenic acid. In one embodiment the agent is a pantothenate kinase agonist. In one embodiment, the agent is administered orally, parenterally, topically, intraocularly, intradermally or subcutaneously.

In one embodiment, a pharmaceutical composition is provided comprising an agent that increases intracellular coenzyme A levels for administration to a subject to increase alternative macrophage activation. In one embodiment, the agent is coenzyme A, an active analogue thereof or an agent that increases the biosynthesis of coenzyme A.

In one embodiment, increasing alternative macrophage activation suppresses or resolves an immune response in the subject. In one embodiment, the immune response occurs in disease or condition selected from diet-induced obesity, inflammation-related metabolic disorders, metabolic syndrome, sepsis, rheumatoid arthritis, eczemas, allergic or atopic dermatitis, and an inflammatory condition of the eye. In one embodiment, the suppression or resolution of the immune response promotes tissue repair, wound healing, repair of skin damage from burns, sunburn or radiation damage. In one embodiment, increasing alternative macrophage activation suppresses or treats a parasitic infection.

In one embodiment, a pharmaceutical composition is provided comprising agent that increases intracellular coenzyme A levels for administration to a subject to suppress or resolve an immune response. In one embodiment, the agent is coenzyme A, an active analogue thereof or an agent that increases biosynthesis of coenzyme A. In one embodiment, the immune response occurs in disease or condition selected from diet-induced obesity, inflammation-related metabolic disorders, metabolic syndrome, sepsis, rheumatoid arthritis, eczemas, allergic or atopic dermatitis, and an inflammatory condition of the eye. In one embodiment, the suppression or resolution of the immune response promotes tissue repair, wound healing, repair of skin damage from burns, sunburn or radiation damage. In one embodiment, increasing alternative macrophage activation suppresses or treats a parasitic infection.

In one embodiment, use of an agent is provided that increases intracellular coenzyme A levels for administering to a subject to increase alternative macrophage activation. In one embodiment, the agent is coenzyme A, an active analogue thereof or an agent that increases the biosynthesis of coenzyme A. In one embodiment, increasing alternative macrophage activation suppresses or resolves an immune response in the subject. In one embodiment, the immune response occurs in disease or condition selected from diet-induced obesity, inflammation-related metabolic disorders, metabolic syndrome, sepsis, rheumatoid arthritis, eczemas, allergic or atopic dermatitis, and an inflammatory condition of the eye. In one embodiment, the suppression or resolution of the immune response promotes tissue repair, wound healing, repair of skin damage from burns, sunburn or radiation damage. In one embodiment, increasing alternative macrophage activation suppresses or treats a parasitic infection.

In one embodiment, a method is provided for suppressing or resolving an immune response in a subject by administering to said subject an agent that increases alternative macrophage activation. In one embodiment, the agent increases intracellular coenzyme A levels. In one embodiment, the immune response occurs in disease or condition selected from diet-induced obesity, inflammation-related metabolic disorders, metabolic syndrome, sepsis, rheumatoid arthritis, eczemas, allergic or atopic dermatitis, and an inflammatory condition of the eye. In one embodiment, the suppression or resolution of the immune response promotes tissue repair, wound healing, repair of skin damage from burns, sunburn or radiation damage. In one embodiment, increasing alternative macrophage activation suppresses or treats a parasitic infection. In one embodiment, the agent is coenzyme A, an active analogue thereof, or the agent that increases biosynthesis of coenzyme A. In one embodiment, the agent is pantothenic acid. In one embodiment, the agent is administered orally, parenterally, topically, intraocularly, intradermally or subcutaneously.

In one embodiment, a method is provided for treating diet-induced obesity, inflammation-related metabolic disorders, metabolic syndrome, sepsis, rheumatoid arthritis, eczemas, allergic or atopic dermatitis, an inflammatory condition of the eye, or promoting tissue repair, wound healing, repair of skin damage from burns, sunburn or radiation damage, or suppressing or treating a parasitic infection in a subject comprising administering to the subject an agent that increases alternative macrophage activation. In one embodiment, the agent increases intracellular levels of coenzyme A. In one embodiment, the agent is coenzyme A, an active analogue thereof, or an agent that increases biosynthesis of coenzyme A. In one embodiment, the agent is pantothenic acid. In one embodiment the agent is a pantothenate kinase agonist. In one embodiment, the agent is administered orally, parenterally, topically, intraocularly, intradermally or subcutaneously.

In one embodiment, a method is provided for treating diet-induced obesity, inflammation-related metabolic disorders, metabolic syndrome, sepsis, rheumatoid arthritis, eczemas, allergic or atopic dermatitis, an inflammatory condition of the eye, or promoting tissue repair, wound healing, repair of skin damage from burns, sunburn or radiation damage, or suppressing or treating a parasitic infection in a subject comprising administering to the subject an agent that increases intracellular levels of coenzyme A, an active analogue thereof, or an agent that increases biosynthesis of coenzyme A. In one embodiment the agent is pantothenic acid. In one embodiment the agent is a pantothenate kinase agonist. In one embodiment, the agent is administered orally, parenterally, topically, intraocularly, intradermally or subcutaneously.

In one embodiment, a method is provided for decreasing alternative macrophage activation in a subject by administering an agent that decreases intracellular coenzyme A levels. In one embodiment, decreasing alternate macrophage activation suppresses or treats non-alcoholic steatohepatitis, non-alcoholic fatty liver disease, pulmonary fibrosis, cardiac hypertrophy. In one embodiment, decreasing alternate macrophage activation suppresses or treats fibrosis and fibrotic diseases and disorders. In one embodiment, decreasing alternate macrophage activation suppresses tumorigenesis or cancer growth. In one embodiment, the agent inhibits intracellular coenzyme A bio activity or coenzyme A biosynthesis. In one embodiment, the agent is a pantothenate kinase inhibitor such as but not limited to hopantenate, alpha-methyl-N-phenethyl-pantothenamide, a 2-methylimidazo[1,2-a]pyridine-3-carboxamide, or 2-methylimidazo[1,2-a]pyridine-3-carbohydrazide. In one embodiment, the agent is administered orally, parenterally, topically, intraocularly, intradermally or subcutaneously.

In one embodiment, a pharmaceutical composition is provided comprising an agent that decreases intracellular coenzyme A levels for administration to a subject to decrease alternative macrophage activation. In one embodiment, the agent inhibits intracellular coenzyme A bioactivity or coenzyme A synthesis. In one embodiment, the agent is a pantothenate kinase inhibitor such as but not limited to hopantenate, alpha-methyl-N-phenethyl-pantothenamide, a 2-methylimidazo[1,2-a]pyridine-3-carboxamide, or 2-methylimidazo[1,2-a]pyridine-3-carbohydrazide. In one embodiment, decreasing alternative macrophage activation suppresses or treats non-alcoholic steatohepatitis, non-alcoholic fatty liver disease, pulmonary fibrosis, cardiac hypertrophy, fibrosis and fibrotic diseases and disorders, and suppresses tumorigenesis or cancer growth.

In one embodiment, use is provided of an agent that decreases intracellular coenzyme A levels for administering to a subject to decrease alternative macrophage activation. In one embodiment, the agent inhibits intracellular coenzyme A bioactivity or coenzyme A biosynthesis. In one embodiment, the agent is a pantothenate kinase inhibitor such as but not limited to hopantenate, alpha-methyl-N-phenethyl-pantothenamide, a 2-methylimidazo[1,2-a]pyridine-3-carboxamide, or 2-methylimidazo[1,2-a]pyridine-3-carbohydrazide. In one embodiment, decreasing alternative macrophage activation suppresses or treats non-alcoholic steatohepatitis, non-alcoholic fatty liver disease, pulmonary fibrosis, cardiac hypertrophy, fibrosis and fibrotic diseases and disorders, and suppresses tumorigenesis or cancer growth.

In one embodiment, a method is provided for suppressing or treating non-alcoholic steatohepatitis, non-alcoholic fatty liver disease, pulmonary fibrosis, cardiac hypertrophy, fibrosis and fibrotic diseases and disorders, and suppresses tumorigenesis or cancer growth comprising administering to a subject an agent that decreases alternative macrophage activation. In one embodiment, the agent decreases intracellular levels of coenzyme A. In one embodiment, the agent inhibits intracellular coenzyme A bioactivity or coenzyme A biosynthesis. In one embodiment, the agent is a pantothenate kinase inhibitor such as but not limited to hopantenate, alpha-methyl-N-phenethyl-pantothenamide, a 2-methylimidazo[1,2-a]pyridine-3-carboxamide, or 2-methylimidazo[1,2-a]pyridine-3-carbohydrazide.

In one embodiment, a method is provided for suppressing or treating non-alcoholic steatohepatitis, non-alcoholic fatty liver disease, pulmonary fibrosis, cardiac hypertrophy, fibrosis and fibrotic diseases and disorders, and suppresses tumorigenesis or cancer growth comprising administering to a subject an agent that decreases intracellular levels of coenzyme A. In one embodiment, the agent inhibits intracellular coenzyme A bioactivity or coenzyme A biosynthesis. In one embodiment, the agent is a pantothenate kinase inhibitor such as but not limited to hopantenate, alpha-methyl-N-phenethyl-pantothenamide, a 2-methylimidazo[1,2-a]pyridine-3-carboxamide, or 2-methylimidazo[1,2-a]pyridine-3-carbohydrazide.

In any of the foregoing embodiments, the increase or decrease in intracellular coenzyme A levels or activity occurs in macrophages.

In one embodiment, a method is provided for modulating alternative macrophage activation in a subject by administering an agent that modulates alternative macrophage activation, determining the level of alternative macrophage activation by measuring a biomarker of alternative macrophage activation on macrophages from the subject, and adjusting the dose regimen of the agent to achieve the level of alternative macrophage activation in said patient. In one embodiment, the level of alternative macrophage activation in the subject is determined by measuring a biomarker of alternative macrophage activation on macrophages from the subject before administering of the agent. In another embodiment, the biomarker is selected from CD206, CD71, CD301 and gene expression of Relma, Mgl2, Ym1, Fabp4, and Arg1.

In one embodiment, a method for identifying an agent capable of modulating alternative macrophage activation is provided by generating M2 macrophages, exposing the macrophages to the agent, evaluating an increase or decrease in the extent of alternative macrophage activation in the macrophages, wherein a change in the extent of alternative macrophage activation indicates the agent is capable of modulating the activation.

BRIEF DESCRIPTIONS OF THE DRAWINGS

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

Figure 8A:
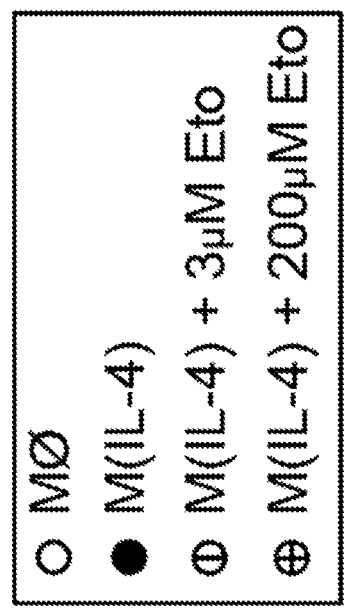
Figure 8A:
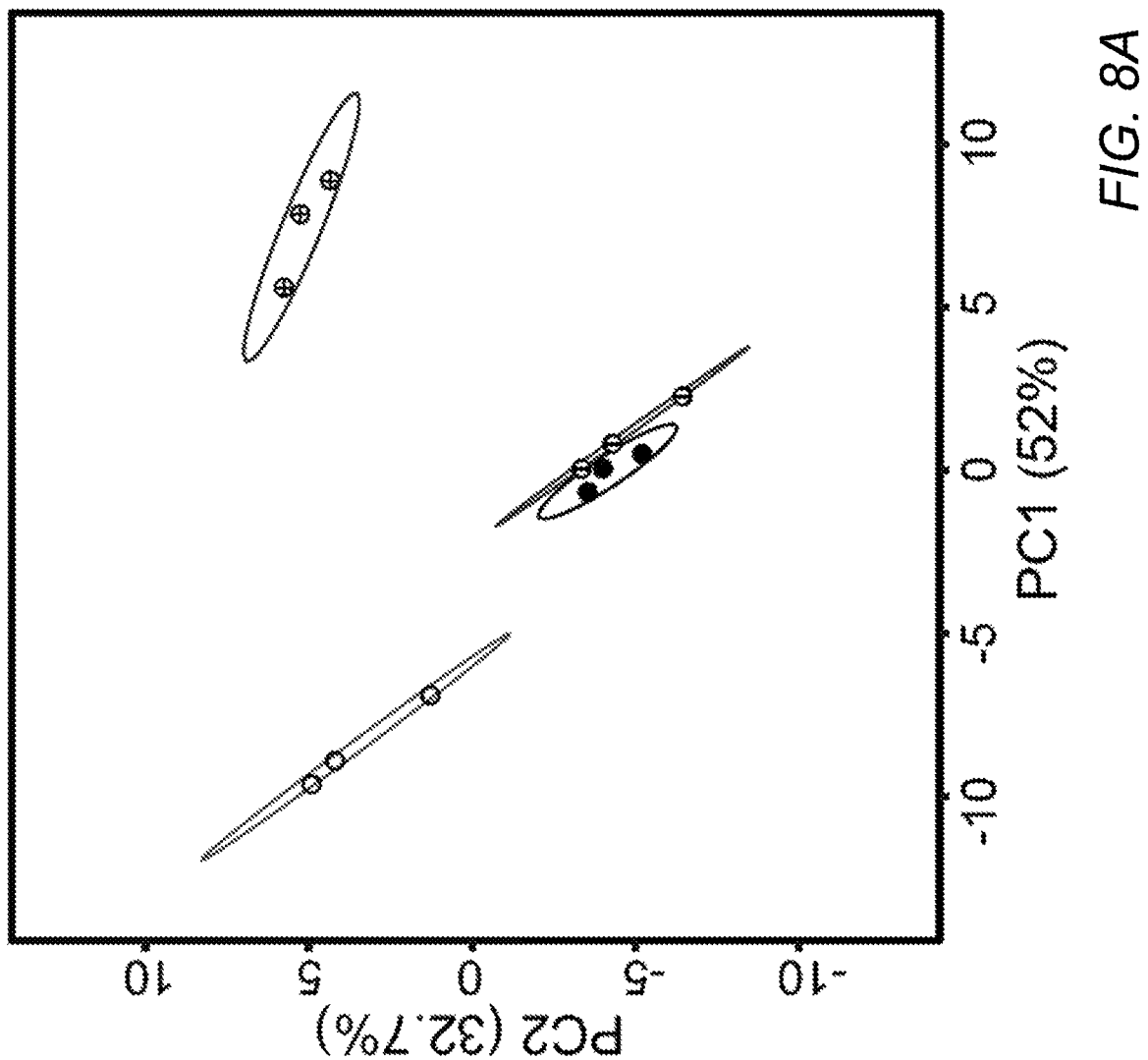
Figure 8C:
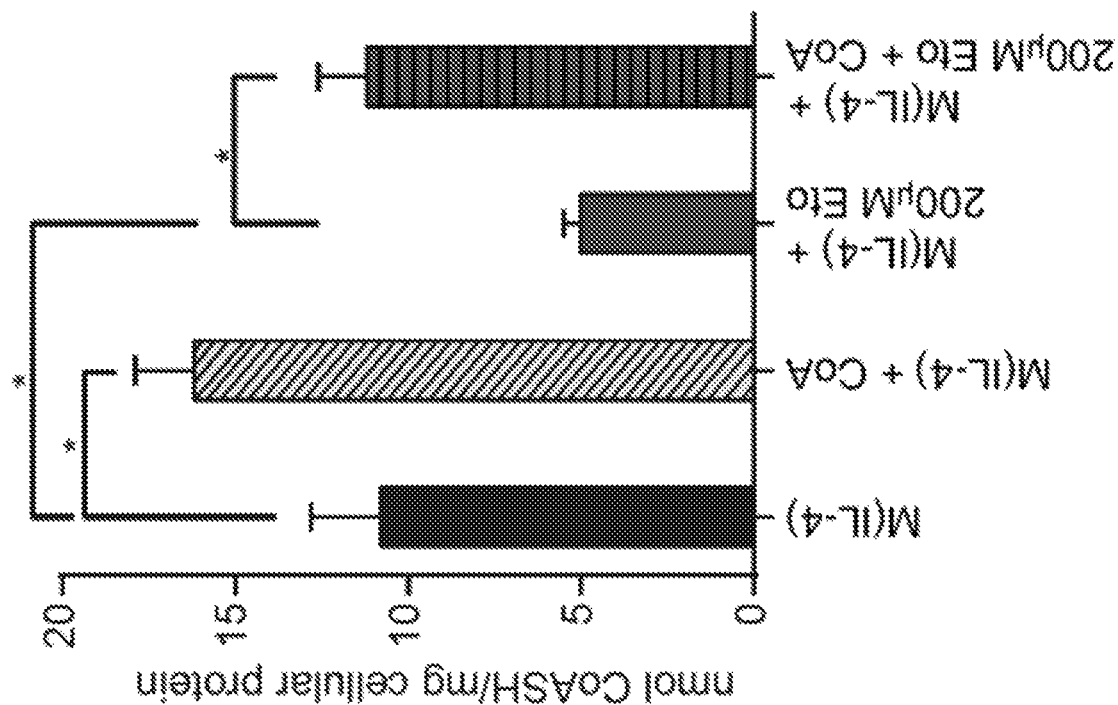
Figure 8B:
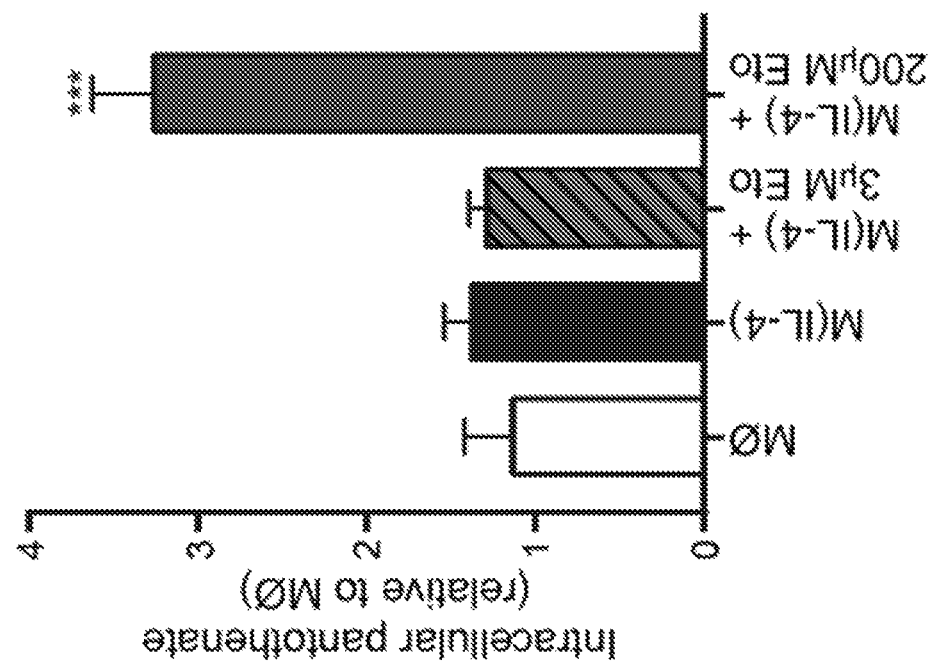
Figure 11A:
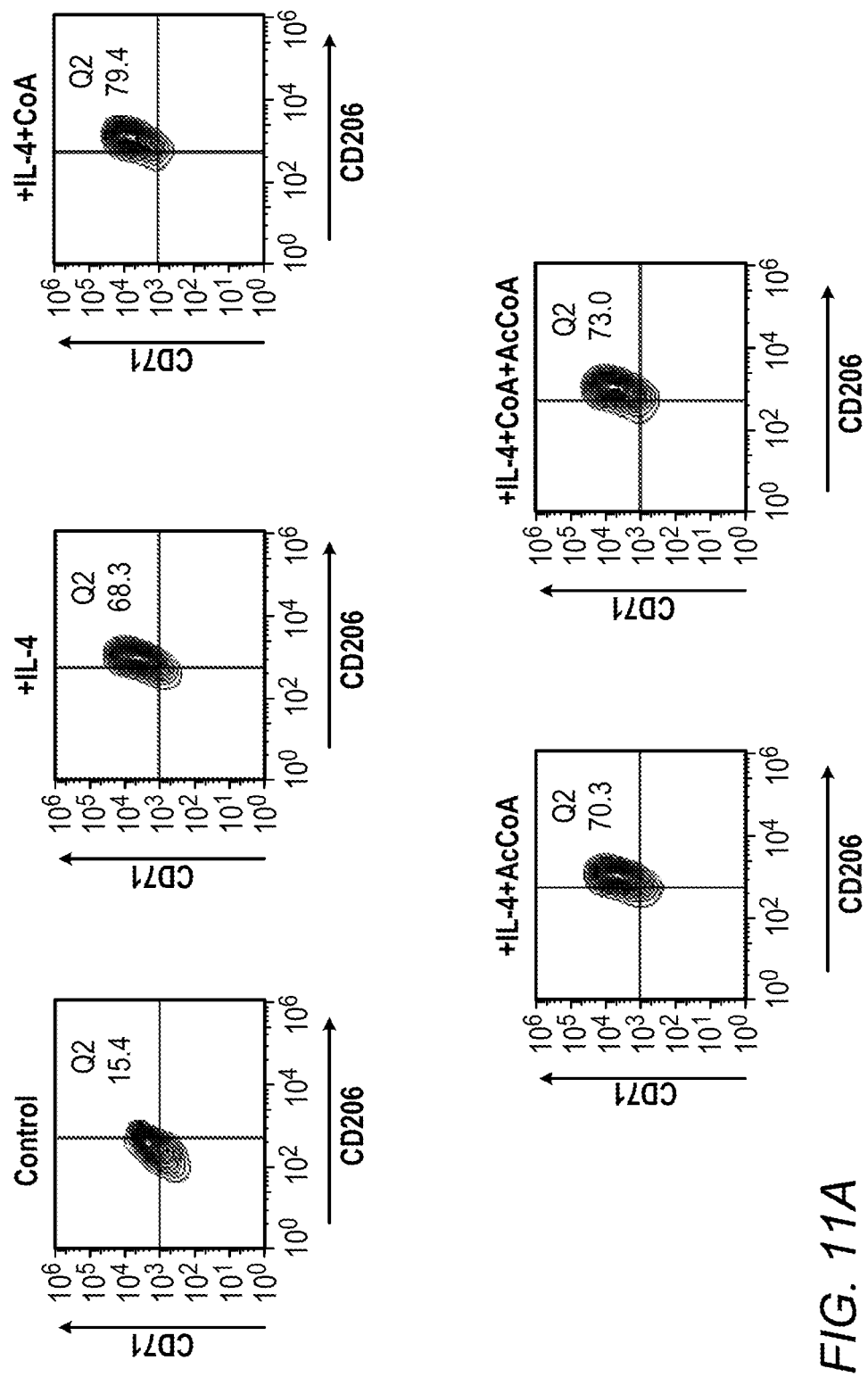
Figure 11B:
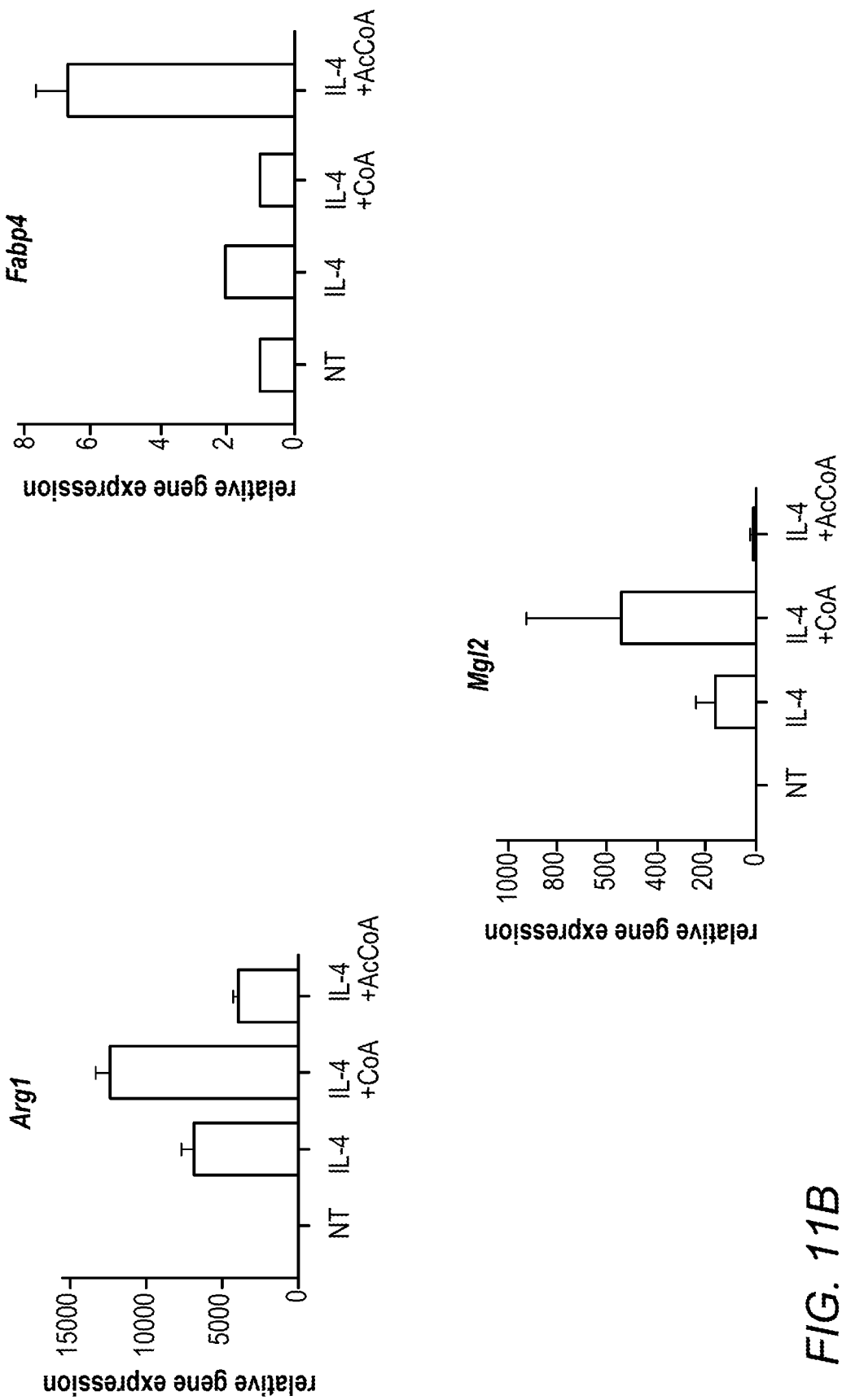
Figure 12:
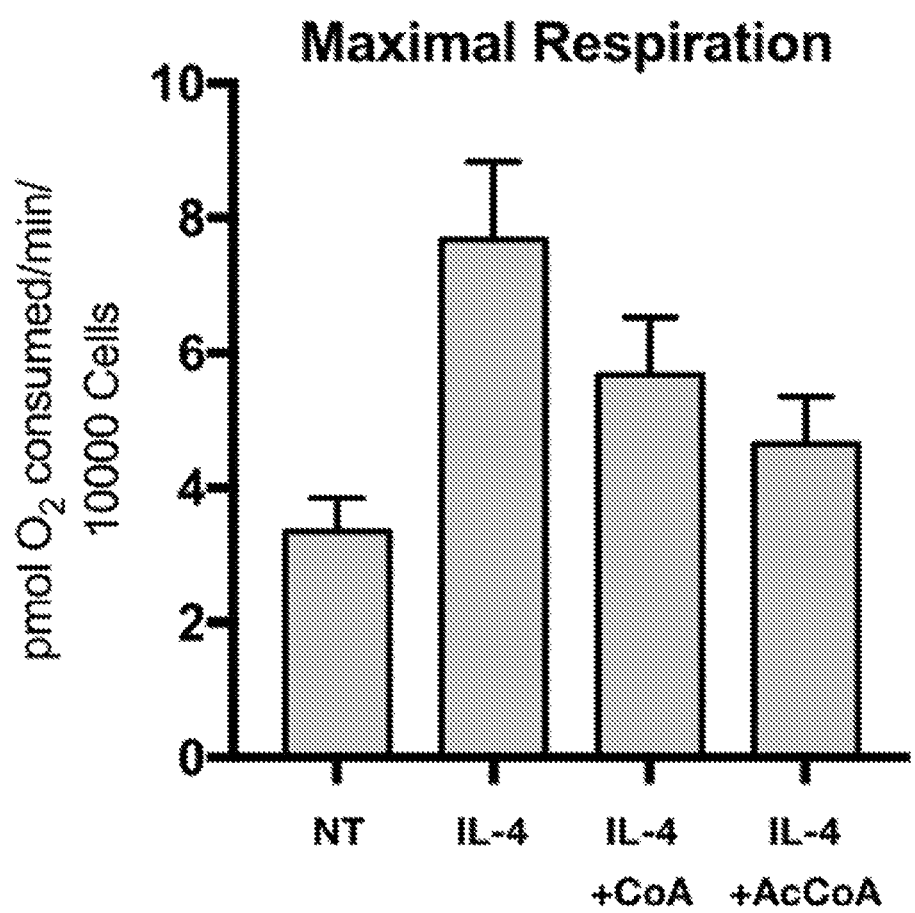

FIG. 3A, FIG. 3B, FIG. 3C, FIG. 3D, FIG. 3E, FIG. 3F, FIG. 3G, FIG. 3H, and FIG. 3I further show that high concentrations of etomoxir block M(IL-4) polarization independently of CPT-1 activity;

FIG. 4A, FIG. 4B, FIG. 4C, FIG. 4D, FIG. 4E, FIG. 4F, FIG. 4G, and FIG. 4H show that excess etomoxir has off-target effects on mitochondrial bioenergetics, but these cannot explain its inhibition of M(IL-4);

FIG. 5A, FIG. 5B, FIG. 5C, FIG. 5D and FIG. 5E further show that excess etomoxir has off-target effects on mitochondrial bioenergetics, but these cannot explain its inhibition of M(IL-4);

FIG. 6A, FIG. 6B, FIG. 6C, FIG. 6D, FIG. 6E, FIG. 6F and FIG. 6G also show that excess etomoxir has off-target effects on mitochondrial bioenergetics, but these cannot explain its inhibition of M(IL-4);

FIG. 7A, FIG. 7B, FIG. 7C, FIG. 7D and FIG. 7E further show that excess etomoxir has off-target effects on mitochondrial bioenergetics, but these cannot explain its inhibition of M(IL-4);

FIG. 8A, FIG. 8B and FIG. 8C show that etomoxir disrupts intracellular CoA homeostasis;

FIG. 9A, FIG. 9B, FIG. 9C and FIG. 9D further show that etomoxir disrupts intracellular CoA homeostasis;

FIG. 10A, FIG. 10B, FIG. 10C, FIG. 10D and FIG. 10E show that Coenzyme A (CoA) rescues inhibition of M(IL-4) polarization by excess etomoxir;

FIG. 11A and FIG. 11B show that coenzyme A does not adjust anti-inflammatory macrophage activation by increasing acetyl-CoA levels; and FIG. 12 shows that coenzyme A does not enhance mitochondrial respiration with IL-4.

DETAILED DESCRIPTION OF THE INVENTION

During studies examining the role of long chain fatty acid (LCFA) oxidation on IL-4-mediated macrophage polarization [also known as M2 polarization, alternative macrophage activation, anti-inflammatory macrophage differentiation, M(IL-4) polarization, and related terms], it was unexpectedly found that depletion of intracellular levels of coenzyme A (CoA) was responsible for M(IL-4) polarization. Moreover, LCFA oxidation was not found to be required for M(IL-4) polarization: the inhibitory activity of etomoxir, a carnitine palmitoyltransferase-1 (CPT1) inhibitor on LCFA oxidation, was disconnected with M(IL-4) polarization and attributed to off-target effects. Thus, modulation of the immune response by manipulating intracellular levels of CoA can be advantageously used in the treatment of numerous diseases and conditions in which altering M(IL-4) polarization is therapeutically beneficial. In one embodiment, increasing M(IL-4) polarization is achieved by increasing intracellular levels of CoA. Increasing M(IL-4) polarization, an anti-inflammatory response, results in the suppression or resolution of the immune response. In another embodiment, decreasing intracellular CoA decreases M(IL-4) polarization, useful in the treatment of diseases and conditions in which excessive M(IL-4) polarization contributes to the pathogenesis of the disease, such as in NASH/NAFLD and fibrosis. These and other aspects of the invention will be described in further detail below.

As will be seen in the examples herein, genetic and pharmacologic models were employed to demonstrate that LCFA oxidation is largely dispensable for IL-4-driven polarization. Unexpectedly, high concentrations of etomoxir retained the ability to disrupt M(IL-4) polarization in the absence of Cpt1a or Cpt2 expression. Although excess etomoxir inhibits the adenine nucleotide translocase (ANT), it was found that oxidative phosphorylation is surprisingly dispensable for M(IL-4). Instead, the block in polarization was traced to depletion of intracellular free CoA, attributed to conversion of the pro-drug etomoxir into active etomoxiryl-CoA. These studies explain the effect(s) of excess etomoxir on immune cells, and reveal an unappreciated role for CoA metabolism in macrophage polarization.

To address these discrepancies, we re-examined the role of LCFA oxidation in macrophage polarization and the inhibitory effects of etomoxir on cellular metabolism. As will be seen in the examples herein, loss of Cpt1a or Cpt2 in myeloid cells has little impact on IL-4-mediated polarization despite significant decreases in LCFA oxidation. Likewise, inhibition of CPT-1 enzymatic activity with a low yet effective concentration of etomoxir (3 µM) did not influence M(IL-4) polarization, suggesting that LCFA oxidation is dispensable for this process. Nevertheless, treatment of macrophages with a higher concentration of etomoxir (200 µM) inhibited polarization even in the absence of Cpt1a. This indicated that the inhibitory effect of excess etomoxir on alternative macrophage activation is an off-target effect. Mechanistic studies revealed that high concentrations of etomoxir inhibit the adenine nucleotide translocase (ANT) and respiratory complex I, suggesting that perturbations in mitochondrial function could be responsible for this effect on macrophages. However, we observed that pharmacologic inhibition of oxidative phosphorylation with a variety of inhibitors had no significant effect on M(IL-4) polarization. Metabolomics studies on IL-4-differentiated macrophages treated with 3 µM or 200 µM etomoxir suggested that the inhibitory effects on macrophage polarization were a function of perturbed intracellular coenzyme A homeostasis. Consistent with this, CoA supplementation was sufficient to overcome the etomoxir-mediated blockade of alternative activation. Moreover, provision of exogenous CoA was able to augment M(IL-4) polarization even in the absence of etomoxir. Taken together, these findings show that LCFA oxidation is largely dispensable for IL-4-driven macrophage polarization, and identify CoA metabolism as an important regulator for macrophage fate.

Although LCFA oxidation and oxidative phosphorylation are dispensable for M(IL-4) polarization, we demonstrate an essential role for homeostatic CoA metabolism. We find that use of etomoxir at high concentrations (200 µM) depletes intracellular CoA and results in the accumulation of the CoA precursor pantothenate. Importantly, not only does medium supplementation with exogenous CoA restore polarization in etomoxir-treated cells, but elevating intracellular CoA levels in control BMDMs is also sufficient to significantly increase the population of CD206+/CD71+ cells. This suggests CoA availability may be a limiting and targetable factor in regulating M(IL-4) polarization.

The sequelae of inflammation wreak a massive and costly burden on society through a wide spectrum of diseases and conditions that both acutely and chronically affect an enormous patient population. Common among these inflammatory diseases and conditions is a therapeutically feasible target: the macrophage, a critical participant in inflammation and having multiple roles. Alternative macrophage activation, an anti-inflammatory pathway, is a therapeutically promising approach for a number of significant diseases and conditions; alternatively, suppressing its anti-inflammatory role has benefit for other but equally significant diseases and conditions. The invention is directed to exploiting these pathways for therapeutic benefit.

In one embodiment, a method is provided for increasing alternative macrophage activation in a subject by administering an agent that increases intracellular CoA levels. Increasing alternative macrophage activation, in one embodiment, is an anti-inflammatory pathway that counteracts proinflammatory and cellular immune effector mechanisms, and can suppress or resolve an immune response, an excessive immune response, or an inflammatory disease or condition in a subject. In one embodiment, the disease or condition is a metabolic disorder such as diet-induced obesity, metabolic syndrome, and the like. In one embodiment the disease or condition is would healing, such as from injury, surgery or disease such as diabetic and decubitus ulcers. In one embodiment the disease or condition is an autoimmune disease or allergic response, such as but not limited to rheumatoid arthritis, eczema, psoriasis, allergic dermatitis, and atopic dermatitis. In one embodiment the disease or condition is burns, radiation burns and sunburn. In one embodiment the disease or condition is an inflammatory disease of the eye such as uveitis. The foregoing conditions and diseases are merely exemplary of the harnessing of alternative macrophage activation for therapeutic benefit.

In certain embodiments herein, changing intracellular CoA levels occurs in the macrophage. In the embodiments herein, macrophages may be specifically targeted for delivery of an agent or means for changing intracellular CoA levels, or the tissues or organ containing macrophages to be affected by the invention herein targeted for changing CoA levels. In other embodiments, the agent or means for changing intracellular CoA levels is directed systemically with the desired benefit upon the macrophage.

Coenzyme A (CoA, CoASH or HSCoA) is a coenzyme containing pantothenic acid, adenosine 3-phosphate 5-pyrophosphate, and cysteamine, and is involved in the transfer of acyl groups, notably in transacetylations. Its chemical name is [(2R,3S,4R,5R)-5-(6-aminopurin-9-yl)-4-hydroxy-3-phosphonooxy-oxolan-2-yl]methyl [hydroxy-[(3R)-3-hydroxy-2,2-dimethyl-4-oxo-4-[[3-oxo-3-(2-sulfanylethylamino) propyl]amino]butoxy]phosphoryl] hydrogen phosphate, and has a molecular weight of about 768 da. In one embodiment, CoA is administered to the subject in need thereof, at a dose, dosing schedule and a route that increases intracellular CoA levels in the cells, tissues or organs involved in the disease process, such that alternative macrophage activation occurs in or at the desired site. In certain diseases and conditions, the desired effect may be systemic or localized to a particular tissue or organ, and CoA can be administered by a route necessary to affect the desired target location. In some disease a systemic effect is desired such that CoA can be administered parenterally. Routes of delivery include, but are not limited to, orally, rectally, parenterally, intracisternally, intravaginally, intraperitoneally, subcutaneously, intradermally, intraocularly, topically (as by powders, ointments, or drops, to the skin, eye, or other site), buccally, as an oral or nasal spray, for example.

In one embodiment, an active analogue of CoA can be used to carry out the invention, such as but not limited to a CoA ester such as an acyl or fatty acid acyl ester, such as but not limited acetyl-CoA, propionyl-CoA, butyryl-CoA, myristoyl-CoA, crotonyl-CoA, acetoacetyl-CoA, benzoyl-CoA, hydroxymethylglutaryl-CoA, pimeloyl-CoA, succinyl-CoA, malonyl-CoA and palmitoyl-CoA. CoA esters of other short-chain as well as complex lipids are embodied herein. Active analogue refers to a compound with the same or similar biological activity as CoA.

In one embodiment, intracellular levels of CoA are increased by administering to the subject an agent that increases levels of CoA, such as but not limited to a biosynthetic precursor of CoA such as pantothenic acid. Pantothenic acid, also known as vitamin B5, is 3-[(2,4-dihydroxy-3,3-dimethylbutanoyl)amino]propanoic acid and has a molecular weight of about 291 da. It is also referred to as pantothenate. Routes, dose levels, and dosing schedule are as required for alternative macrophage activation in the desired bodily site for the treatment of the desired disease or disorder, following the guidance described here for CoA. In one embodiment, coenzyme A levels may be elevated by administering one or more biosynthetic precursors to coenzyme A including pantothenic acid (vitamin B5), cysteine and adenine nucleotide, or administering one or more biosynthetic precursors of the aforementioned precursors of coenzyme A. In one embodiment, any combination of the aforementioned compounds, precursors, and biosynthetic precursors of coenzyme A precursors comprise the agent. In another embodiment, non-biosynthetic compounds that are metabolized to precursors comprise the agent, such as but not limited to N-acetylcysteine that is metabolized in vivo to cysteine; and pantothenate derivatives and prodrugs.

In another embodiment, the agent is one or more pantothenate kinase agonists, such as but not limited to those described in Sharma. L. K., Leonardi, R., Lin, W., Boyd, V. A., Goktug, A., Shelat, A. A., Chen, T., Jackowski, A. and Rock, C. O. A High-Throughput Screen Reveals New Small-Molecule Activators and Inhibitors of Pantothenate Kinases. J. Med. Chem. 2015, 58, 1563-1568, incorporated herein in its entirety. In another embodiment said one or more pantothenate kinase agonists may be administered with pantothenate or any other agent described herein. In another embodiment, agonists or upregulators of other enzymes in the biosynthesis of coenzyme A or its precursors are included among agents.

In another embodiment, other means for increasing intracellular CoA levels are provided such as through means for regulating intracellular CoA levels, CoA homeostasis or CoA availability within the cell.

In one embodiment, activity of increased alternative macrophage activation can be determined by measuring biomarker levels on macrophages from the tissue or organs in which an effect is desired. Macrophages can be obtained by biopsy and biomarkers measured, such as but not limited to CD206, CD71, CD301 or by assessing gene expression of Relma, Mgl2, Ym1, Fabp4, and Arg1. In one embodiment, the level of expression of biomarkers can be used to adjust the dose level of the agent such that the desired intracellular CoA levels and attendant increase in alternative macrophage activation is achieved or maintained. In one embodiment, the course of therapy to increase alternative macrophage activation then return it to prior levels can be monitored by such biomarker analysis.

Further descriptions of pharmaceutical compositions and other embodiments for dosage forms, dose levels, and delivery of agents that increase intracellular CoA levels are provided further below.

In another embodiment, a pharmaceutical composition is provided comprising an agent that increases intracellular CoA levels, for increasing alternative macrophage activation, for the purposes described in the various embodiments herein. The agent is any of the compounds and methods described herein for increasing alternative macrophage activation. The pharmaceutical composition may comprise an amount of such agent to achieve the desired purpose, which in combination with a dosing regimen and route of administration, achieves the desired purpose. In one embodiment, any of the dose forms, dose levels, and routes of administration described herein are utilized.

Another embodiment is directed to the use of an agent that increases intracellular CoA levels for administration to a subject to increase alternative macrophage activation, for the purposes described herein. The agent is any of the compounds and methods described herein for increasing alternative macrophage activation. The pharmaceutical composition may comprise an amount of such agent to achieve the desired purpose, which in combination with a dosing regimen and route of administration, achieves the desired purpose. In one embodiment, any of the dose forms, dose levels, and routes of administration described herein are utilized.

The studies described herein also demonstrate the ability to decrease alternative macrophage activation by decreasing intracellular levels of coenzyme A. In another embodiment, a method is provided for decreasing alternative macrophage activation by lowering intracellular levels of CoA, for therapeutic benefit. As for the various embodiments described above for increasing intracellular CoA levels, the similar general principles apply for targeting the desired macrophages, tissues, organs or for systemic administration.

In one embodiment, lowering intracellular CoA levels reduces alternative macrophage activation, which is beneficial in the treatment of certain diseases and conditions in which excess alternative macrophage activation contributes to disease pathogenesis, such as but not limited to non-alcoholic fatty liver disease, non-alcoholic steatohepatitis, pulmonary fibrosis and other fibrotic diseases, and cardiac hypertrophy. Other fibrotic diseases include but are not limited to fibrotic liver disease; hepatic ischemia-reperfusion injury; cerebral infarction: ischemic heart disease; renal disease; lung (pulmonary) fibrosis; liver fibrosis associated with hepatitis C, hepatitis B, delta hepatitis, chronic alcoholism, non-alcoholic steatohepatitis, stones in the bile duct, cholangiopathies selected from primary biliary cirrhosis and sclerosing cholangitis, autoimmune hepatitis, and inherited metabolic disorders selected from Wilson's disease, hemochromatosis, and alpha-1-antitrypsin deficiency: damaged and/or ischemic organs, transplants or grafts; ischemia/reperfusion injury; stroke; cerebrovascular disease; myocardial ischemia; atherosclerosis; renal failure; renal fibrosis; idiopathic pulmonary fibrosis; wounds; ischemia/reperfusion injury in the brain, heart, liver and kidney; myocardial perfusion as a consequence of chronic cardiac ischemia or myocardial infarction; vascular occlusion; liver fibrosis or cirrhosis; radiocontrast nephropathy: fibrosis secondary to renal obstruction; renal trauma and transplantation; renal failure secondary to chronic diabetes and/or hypertension; and/or diabetes mellitus.

In another embodiment, decreasing intracellular CoA levels can be used to treat cancer. In one embodiment, the population of tumor-associated macrophages or myeloid-derived suppressor cells is reduced by reducing intracellular CoA levels. In one embodiment, a cancer that is treatable by reducing tumor growth-enhancing cells or tumor-protective cells is a myelodysplastic or myeloproliferative tumor. In one embodiment, the tumor growth-enhancing or tumor-protective cells are innate immune cells, such as but not limited to macrophages. In one embodiment decreasing intracellular CoA levels reduces or inhibits the immunosuppressive function of tumor-associated macrophages (TAMs) and/or myeloid-derived suppressor cells (MDSCs). In one embodiment, these cells suppress T cell activity, keeping them at bay and allowing tumors to grow. In one embodiment, blocking the function of TAMs or MDSCs improve the body's immune response to fight the tumor. In one embodiment the cancer is pancreatic cancer, breast cancer, ovarian cancer, glioma, lymphoma, leukemia, myelodysplastic syndrome, colon cancer, stomach cancer, lung cancer and prostate cancer, by way of non-limiting examples. In one embodiment, the coenzyme A level reducing agent is administered along with a standard of care therapy, such as chemotherapy.

In one embodiment, intracellular CoA levels are reduced by administering to the bodily site or subject an agent that inhibits CoA biosynthesis or inhibits coenzyme A bioactivity. In one embodiment the agent inhibits pantothenate kinase. In one embodiment the agent is alpha-methyl-N-phenethyl-pantothenamide, a 2-methylimidazo[1,2-a]pyridine-3-carboxamide, or 2-methylimidazo[1,2-a]pyridine-3-carbohydrazide. In another embodiment, the agent is pantoyl-gamma-aminobutyrate (hopantenate). In another embodiment, the agent is one or more pantothenate kinase inhibitors such as but not limited to those described in Sharma, L. K., Leonardi, R., Lin, W., Boyd, V. A., Goktug, A., Shelat, A. A., Chen, T., Jackowski, A. and Rock, C. O. A High-Throughput Screen Reveals New Small-Molecule Activators and Inhibitors of Pantothenate Kinases. J. Med. Chem. 2015, 58, 1563-1568, incorporated herein in its entirety. In another embodiment said one or more pantothenate kinase inhibitors may be administered with any other agent described herein. In another embodiment, inhibitors or downregulators of other enzymes in the biosynthesis of coenzyme A or its precursors are included among agents.

In another embodiment, the agent is a compound that binds or sequesters coenzyme A and depletes intracellular levels.

In one embodiment, activity of decreased alternative macrophage activation can be determined by measuring biomarker levels on macrophages from the tissue or organs in which an effect is desired. Macrophages can be obtained by biopsy and biomarkers measured, such as but not limited to CD206, CD71, CD301 or by assessing gene expression of Relma, Mgl2, Ym1, Fabp4, and Arg1. In one embodiment, the level of expression of biomarkers can be used to adjust the dose level of the agent such that the desired decreased intracellular CoA levels and attendant decrease in alternative macrophage activation is achieved or maintained. In one embodiment, the course of therapy to decrease alternative macrophage activation then return it to prior levels can be monitored by such biomarker analysis.

Further descriptions of pharmaceutical compositions and other embodiments for delivery of agents that decrease intracellular CoA levels are provided further below.

In another embodiment, a pharmaceutical composition is provided comprising an agent that decreases intracellular CoA levels, for decreasing alternative macrophage activation, for the purposes described herein in the various embodiments herein. The agent is any of the compounds and methods described herein for decreasing alternative macrophage activation. The pharmaceutical composition may comprise an amount of such agent to achieve the desired purpose, which in combination with a dosing regimen and route of administration, achieves the desired purpose. In one embodiment, any of the dose forms, dose levels, and routes of administration described herein are utilized.

Another embodiment is directed to the use of a compound that decreases intracellular CoA levels for administration to a subject to decrease alternative macrophage activation, for the purposes described herein in the various embodiments herein. The agent is any of the compounds and methods described herein for decreasing alternative macrophage activation. The pharmaceutical composition may comprise an amount of such agent to achieve the desired purpose, which in combination with a dosing regimen and route of administration, achieves the desired purpose. In one embodiment, any of the dose forms, dose levels, and routes of administration described herein are utilized.

As noted above, for any of the treatment embodiments of the invention, assessment of biomarker levels of alternative macrophage activation can be used to guide the course of treatment, including but not limited to dose level, dosing frequency and duration of dosing, as well as route of administration. In one embodiment, a method for modulating alternative macrophage activation in a subject by the steps of administering an agent that modulates alternative macrophage activation, determining the level of alternative macrophage activation by measuring a biomarker of alternative macrophage activation on macrophages from the subject; and adjusting the dose regimen of the agent to achieve the level of alternative macrophage activation in said patient. In another embodiment, the baseline level of alternative macrophage activation is determined prior to the start of therapy. The biomarker or combination of biomarkers or levels of gene expression may be any one or more of those described herein.

In one embodiment, a method for identifying an agent capable of modulating alternative macrophage activation is provided by generating M2 macrophages, exposing the macrophages to the agent, evaluating an increase or decrease in the extent of alternative macrophage activation in the macrophages, wherein a change in the extent of alternative macrophage activation indicates the agent is capable of modulating the activation. In one embodiment the agent increases alternative macrophage activation. In one embodiment the agent decreases alternative macrophage activation. In one embodiment, the M2 macrophages are generated by exposing macrophages to IL-4. In one embodiment the extent of alternative macrophage activation is assessed by the level of expression of biomarkers or level gene expression indicative of alternative macrophage activation, such as but not limited to expression of CD206, CD71, CD301 or gene expression of Relma, Mgl2, Ym1, Fabp4, and Arg1.

In any of the foregoing embodiments, the agent may be one or more agents, compounds, or other materials or means for achieving the purpose of increasing or decreasing intracellular coenzyme A levels or bioactivity. Each of the agents may be administered in the same or different formulations, by the same or different dose levels, by the same or different routes of administration, the same or different dosing frequency or the same or different duration of dosing, to achieve the desired purpose. By way of non-limiting example, for increasing intracellular coenzyme A levels, the biosynthetic precursors pantothenic acid (vitamin B5), cysteine and adenine nucleotide may comprise the agent and be administered together or individually or in any combination, to achieve the elevation of intracellular coenzyme A levels. In another embodiment, the agent may comprise one or more biosynthetic precursors of the aforementioned precursors of coenzyme A. In one embodiment, a pantothenate kinase agonist is included in the agent. In another non-limiting embodiment, the agent or means to decrease intracellular coenzyme A may comprise one or more inhibitors of pantothenate kinase, each administered by the dose level, rote of administration, frequency and duration to lower intracellular coenzyme A levels. In another embodiment, pantothenic acid and a pantothenate kinase agonist may be administered.

Accordingly, in another aspect of the present invention, pharmaceutical compositions are provided, which comprise any one or more of the compounds described herein (or a prodrug, pharmaceutically acceptable salt or other pharmaceutically acceptable derivative thereof), and optionally comprise a pharmaceutically acceptable carrier. In certain embodiments, these compositions optionally further comprise one or more additional therapeutic agents. Alternatively, a compound of this invention may be administered to a patient in need thereof in combination with the administration of one or more other therapeutic agents. For example, additional therapeutic agents for conjoint administration or inclusion in a pharmaceutical composition with a compound of this invention may be an approved agent to treat the same or related indication, such as a standard-of-care treatments for cancer, for example, a chemotherapeutic agent. It will also be appreciated that certain of the compounds of present invention can exist in free form for treatment, or where appropriate, as a pharmaceutically acceptable derivative thereof. According to the present invention, a pharmaceutically acceptable derivative includes, but is not limited to, pharmaceutically acceptable salts, esters, salts of such esters, or a pro-drug or other adduct or derivative of a compound of this invention which upon administration to a patient in need is capable of providing, directly or indirectly, a compound as otherwise described herein, or a metabolite or residue thereof.

As used herein, the term "pharmaceutically acceptable salt" refers to those salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts of amines, carboxylic acids, and other types of compounds, are well known in the art. For example, S. M. Berge, et al. describe pharmaceutically acceptable salts in detail in J. Pharmaceutical Sciences, 66: 1-19 (1977), incorporated herein by reference. The salts can be prepared in situ during the final isolation and purification of the compounds of the invention, or separately by reacting a free base or free acid function with a suitable reagent, as described generally below. For example, a free base function can be reacted with a suitable acid. Furthermore, where the compounds of the invention carry an acidic moiety, suitable pharmaceutically acceptable salts thereof may, include metal salts such as alkali metal salts, e.g. sodium or potassium salts; and alkaline earth metal salts, e.g. calcium or magnesium salts. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, lower alkyl sulfonate and aryl sulfonate.

Additionally, as used herein, the term "pharmaceutically acceptable ester" refers to esters that hydrolyze in vivo and include those that break down readily in the human body to leave the parent compound or a salt thereof. Suitable ester groups include, for example, those derived from pharmaceutically acceptable aliphatic carboxylic acids, particularly alkanoic, alkenoic, cycloalkanoic and alkanedioic acids, in which each alkyl or alkenyl moiety advantageously has not more than 6 carbon atoms. Examples of particular esters include formates, acetates, propionates, butyrates, acrylates and ethylsuccinates.

Furthermore, the term "pharmaceutically acceptable prodrugs" as used herein refers to those prodrugs of the compounds of the present invention which are, within the scope of sound medical judgment, suitable for use in contact with the issues of humans and lower animals with undue toxicity, irritation, allergic response, and the like, commensurate with a reasonable benefit/risk ratio, and effective for their intended use, as well as the zwitterionic forms, where possible, of the compounds of the invention. The term "prodrug" refers to compounds that are rapidly transformed in vivo to yield the parent compound of the above formula, for example by hydrolysis in blood, or N-demethylation of a compound of the invention where R1 is methyl. A thorough discussion is provided in T. Higuchi and V. Stella, Pro-drugs as Novel Delivery Systems, Vol. 14 of the A.C.S. Symposium Series, and in Edward B. Roche, ed., Bioreversible Carriers in Drug Design, American Pharmaceutical Association and Pergamon Press, 1987, both of which are incorporated herein by reference. By way of other examples, carbamate and amide prodrugs of compounds of formulae (I)-(IV) are embodied herein, such as those discussed in Rautio et al., 2008, Nature Rev Drug Discov 7:255-70; Jordan et al., 2003, Bioorg Med Chem 10:2625-33 and Hay et al., 2003, J Med Chem 46:5533-45, by way of non-limiting examples.

As described above, the pharmaceutical compositions of the present invention additionally comprise a pharmaceutically acceptable carrier, which, as used herein, includes any and all solvents, diluents, or other liquid vehicle, dispersion or suspension aids, surface active agents, isotonic agents, thickening or emulsifying agents, preservatives, solid binders, lubricants and the like, as suited to the particular dosage form desired. Remington's Pharmaceutical Sciences, Sixteenth Edition, E. W. Martin (Mack Publishing Co., Easton, Pa., 1980) discloses various carriers used in formulating pharmaceutical compositions and known techniques for the preparation thereof. Except insofar as any conventional carrier medium is incompatible with the compounds of the invention, such as by producing any undesirable biological effect or otherwise interacting in a deleterious manner with any other component(s) of the pharmaceutical composition, its use is contemplated to be within the scope of this invention. Some examples of materials which can serve as pharmaceutically acceptable carriers include, but are not limited to, sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatine; talc; excipients such as cocoa butter and suppository waxes; oils such as peanut oil, cottonseed oil; safflower oil, sesame oil; olive oil; corn oil and soybean oil; glycols; such as propylene glycol; esters such as ethyl oleate and ethyl laurate; agar; buffering agents such as magnesium hydroxide and aluminum hydroxide; alginic acid; pyrogen free water; isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator.

Liquid dosage forms for oral administration include, but are not limited to, pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut (peanut), corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a drug, it is often desirable to slow the absorption of the drug from subcutaneous or intramuscular injection. This may be accomplished by the use of a liquid suspension or crystalline or amorphous material with poor water solubility. The rate of absorption of the drug then depends upon its rate of dissolution that, in turn, may depend upon crystal size and crystalline form. Alternatively, delayed absorption of a parenterally administered drug form is accomplished by dissolving or suspending the drug in an oil vehicle. Injectable depot forms are made by forming microencapsule matrices of the drug in biodegradable polymers such as polylactide-polyglycolide. Depending upon the ratio of drug to polymer and the nature of the particular polymer employed, the rate of drug release can be controlled. Examples of other biodegradable polymers include (poly(orthoesters) and poly(anhydrides). Depot injectable formulations are also prepared by entrapping the drug in liposomes or microemulsions which are compatible with body tissues.

Compositions for rectal or vaginal administration are preferably suppositories which can be prepared by mixing the compounds of this invention with suitable non-irritating excipients or carriers such as cocoa butter, polyethylene glycol or a suppository wax which are solid at ambient temperature but liquid at body temperature and therefore melt in the rectum or vaginal cavity and release the active compound.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes. Solid compositions of a similar type may also be employed as fillers in soft and hard-filled gelatin capsules using such excipients as lactose or milk sugar as well as high molecular weight polyethylene glycols and the like.

The active compounds can also be in micro-encapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active compound may be admixed with at least one inert diluent such as sucrose, lactose and starch. Such dosage forms may also comprise, as in normal practice, additional substances other than inert diluents, e.g., tableting lubricants and other tableting aids such as magnesium stearate and microcrystalline cellulose. In the case of capsules, tablets and pills, the dosage forms may also comprise buffering agents. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes.

In other embodiments solid dosage forms are provided. In certain embodiments, such solid dosage forms provide a higher than about a 20% oral bioavailability. As will be shown in the examples below, compounds of the invention can be co-precipitated with one or more agents such as mannitol, a combination of mannitol and lactobionic acid, a combination of mannitol and gluconic acid, a combination of mannitol and methanesulfonic acid, a combination of microcrystalline cellulose and oleic acid or a combination of pregelatinized starch and oleic acid. The foregoing examples of one or more agents to aid in preparing formulations of inventive compound are merely illustrative and non-limiting. Non-limiting examples of inventive compounds in such solid dosage forms include The present invention encompasses pharmaceutically acceptable topical formulations of inventive compounds. The term "pharmaceutically acceptable topical formulation", as used herein, means any formulation which is pharmaceutically acceptable for intradermal administration of a compound of the invention by application of the formulation to the epidermis. In certain embodiments of the invention, the topical formulation comprises a carrier system. Pharmaceutically effective carriers include, but are not limited to, solvents (e.g., alcohols, poly alcohols, water), creams, lotions, ointments, oils, plasters, liposomes, powders, emulsions, microemulsions, and buffered solutions (e.g., hypotonic or buffered saline) or any other carrier known in the art for topically administering pharmaceuticals. A more complete listing of art-known carriers is provided by reference texts that are standard in the art, for example, Remington's Pharmaceutical Sciences, 16th Edition, 1980 and 17th Edition, 1985, both published by Mack Publishing Company, Easton, Pa., the disclosures of which are incorporated herein by reference in their entireties. In certain other embodiments, the topical formulations of the invention may comprise excipients. Any pharmaceutically acceptable excipient known in the art may be used to prepare the inventive pharmaceutically acceptable topical formulations. Examples of excipients that can be included in the topical formulations of the invention include, but are not limited to, preservatives, antioxidants, moisturizers, emollients, buffering agents, solubilizing agents, other penetration agents, skin protectants, surfactants, and propellants, and/or additional therapeutic agents used in combination to the inventive compound. Suitable preservatives include, but are not limited to, alcohols, quaternary amines, organic acids, parabens, and phenols. Suitable antioxidants include, but are not limited to, ascorbic acid and its esters, sodium bisulfite, butylated hydroxytoluene, butylated hydroxyanisole, tocopherols, and chelating agents like EDTA and citric acid. Suitable moisturizers include, but are not limited to, glycerine, sorbitol, polyethylene glycols, urea, and propylene glycol. Suitable buffering agents for use with the invention include, but are not limited to, citric, hydrochloric, and lactic acid buffers. Suitable solubilizing agents include, but are not limited to, quaternary ammonium chlorides, cyclodextrins, benzyl benzoate, lecithin, and polysorbates. Suitable skin protectants that can be used in the topical formulations of the invention include, but are not limited to, vitamin E oil, allantoin, dimethicone, glycerin, petrolatum, and zinc oxide.

In certain embodiments, the pharmaceutically acceptable topical formulations of the invention comprise at least a compound of the invention and a penetration enhancing agent. The choice of topical formulation will depend or several factors, including the condition to be treated, the physicochemical characteristics of the inventive compound and other excipients present, their stability in the formulation, available manufacturing equipment, and costs constraints. As used herein the term "penetration enhancing agent" means an agent capable of transporting a pharmacologically active compound through the stratum corneum and into the epidermis or dermis, preferably, with little or no systemic absorption. A wide variety of compounds have been evaluated as to their effectiveness in enhancing the rate of penetration of drugs through the skin. See, for example, Percutaneous Penetration Enhancers, Maibach H. I. and Smith H. E. (eds.), CRC Press, Inc., Boca Raton, Fla. (1995), which surveys the use and testing of various skin penetration enhancers, and Buyuktimkin et al., Chemical Means of Transdermal Drug Permeation Enhancement in Transdermal and Topical Drug Delivery Systems, Gosh T. K., Pfister W. R., Yum S. I. (Eds.), Interpharm Press Inc., Buffalo Grove, Ill. (1997). In certain exemplary embodiments, penetration agents for use with the invention include, but are not limited to, triglycerides (e.g., soybean oil), aloe compositions (e.g., aloe-vera gel), ethyl alcohol, isopropyl alcohol, octolyphenylpolyethylene glycol, oleic acid, polyethylene glycol 400, propylene glycol, N-decylmethylsulfoxide, fatty acid esters (e.g., isopropyl myristate, methyl laurate, glycerol monooleate, and propylene glycol monooleate) and N-methyl pyrrolidone.

In certain embodiments, the compositions may be in the form of ointments, pastes, creams, lotions, gels, powders, solutions, sprays, inhalants or patches. In certain exemplary embodiments, formulations of the compositions according to the invention are creams, which may further contain saturated or unsaturated fatty acids such as stearic acid, palmitic acid, oleic acid, palmito-oleic acid, cetyl or oleyl alcohols, stearic acid being particularly preferred. Creams of the invention may also contain a non-ionic surfactant, for example, polyoxy-40-stearate. In certain embodiments, the active component is admixed under sterile conditions with a pharmaceutically acceptable carrier and any needed preservatives or buffers as may be required. Ophthalmic formulation, eardrops, and eye drops are also contemplated as being within the scope of this invention. Formulations for intraocular administration are also included. Additionally, the present invention contemplates the use of transdermal patches, which have the added advantage of providing controlled delivery of a compound to the body. Such dosage forms are made by dissolving or dispensing the compound in the proper medium. As discussed above, penetration enhancing agents can also be used to increase the flux of the compound across the skin. The rate can be controlled by either providing a rate controlling membrane or by dispersing the compound in a polymer matrix or gel.

It will also be appreciated that the compounds and pharmaceutical compositions of the present invention can be formulated and employed in combination therapies, that is, the compounds and pharmaceutical compositions can be formulated with or administered concurrently with, prior to, or subsequent to, one or more other desired therapeutics or medical procedures. The particular combination of therapies (therapeutics or procedures) to employ in a combination regimen will take into account compatibility of the desired therapeutics and/or procedures and the desired therapeutic effect to be achieved. It will also be appreciated that the therapies employed may achieve a desired effect for the same disorder (for example, an inventive compound may be administered concurrently with another anti-inflammatory agent), or they may achieve different effects (e.g., control of any adverse effects). In non-limiting examples, one or more compounds of the invention may be formulated with at least one cytokine, growth factor or other biological, such as an interferon, e.g., alpha interferon, or with at least another small molecule compound. Non-limiting examples of pharmaceutical agents that may be combined therapeutically with compounds of the invention include: antivirals and antifibrotics such as interferon alpha, combination of interferon alpha and ribavirin, Lamivudine, Adefovir dipivoxil and interferon gamma; anticoagulants such as heparin and warfarin; antiplatelets e.g., aspirin, ticlopidine and clopidogrel; other growth factors involved in regeneration, e.g., VEGF and FGF and mimetics of these growth factors; antiapoptotic agents; and motility and morphogenic agents.

Furthermore, in other embodiments, the subject in need of a treatment described herein may be a human or another mammalian animal, such as but not limited to a rodent, a mouse, a rat, a rabbit, a monkey, a dog, a cat, a sheep, cattle, a primate, or a pig.

Furthermore, after formulation with an appropriate pharmaceutically acceptable carrier in a desired dosage, the agent or pharmaceutical compositions of this invention can be administered to humans and other animals orally, rectally, parenterally, intracisternally, intravaginally, intraperitoneally, subcutaneously, intradermally, intra-ocularly, topically (as by powders, ointments, or drops), buccally, as an oral or nasal spray, or the like, depending on the severity of the disease or disorder being treated. In certain embodiments, the compounds of the invention may be administered at dosage levels of about 0.001 mg/kg to about 50 mg/kg, preferably from about 0.1 mg/kg to about 10 mg/kg for parenteral administration, or preferably from about 1 mg/kg to about 50 mg/kg, more preferably from about 10 mg/kg to about 50 mg/kg for oral administration, of subject body weight per day, one or more times a day, to obtain the desired therapeutic effect. It will also be appreciated that dosages smaller than 0.001 mg/kg or greater than 50 mg/kg (for example 50-100 mg/kg) can be administered to a subject. In certain embodiments, compounds are administered orally or parenterally. The particular dose level, dosing regimen and duration of dosing will depend upon the bioavailability of the agent, the disease, and other factors.

In certain embodiments, the pharmaceutical compositions of the present invention further comprise one or more additional therapeutically active ingredients (e.g., anti-inflammatory and/or palliative). For purposes of the invention, the term "Palliative" refers to treatment that is focused on the relief of symptoms of a disease and/or side effects of a therapeutic regimen, but is not curative. For example, palliative treatment encompasses painkillers, antinausea medications and anti-sickness drugs.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Various embodiments and aspects of the present invention as delineated hereinabove and as claimed in the claims section below find experimental support in the following examples.

EXAMPLES

Materials and Methods

All animal protocols were approved by either the UCSD Institutional Animal Care and Use Committee or the UCLA Animal Research Committee.

Mouse Bone Marrow-Derived (BMDM) and Peritoneal Macrophages

WT Bone marrow cells from WT control, Cpt1−/−, and Cpt2−/− were isolated from femurs of male mice. Cells were treated with RBC lysis buffer to remove red blood cells for five minutes, centrifuged at 386 g for 5 minutes, and resuspended in BMDM culture medium. Culture medium consisted of high-glucose DMEM (Gibco 11965) supplemented with 10% heat-inactivated fetal bovine serum (FBS), 2 mM L-glutamine, 100 units/mL, 100 µg/mL penicillin/streptomycin, 500 µM sodium pyruvate, and 5% v/v conditioned medium containing macrophage colony stimulating factor (M-CSF) produced by CMG cells to induce differentiation to BMDMs (Takeshita, S. Kaji, K., and Kudo, A. (2000) Identification and characterization of the new osteoclast progenitor with macrophage phenotypes being able to differentiate into mature osteoclasts. J Bone Miner Res, 15:1477-88). BMDMs were maintained at 37° C. in a humidified 5% CO2 incubator. BMDMs were differentiated for 6 days prior to harvesting and re-plating for experiments, and medium was changed at Day 4 of differentiation.

Cpt−/− CD11c-Cre Cpt1a−/− BMDMs were generated from crossing Cpt1a flox/flox mice [generously provided by Dr. Peter Carmeliet (Schoors, S., Bruning, U., Missiaen, R., Queiroz, K. C., Borgers, G., Elia, I., Zecchin, A., Cantelmo, A. R., Christen, S., Goveia, J., et al. (2015) Fatty acid carbon is essential for dNTP synthesis in endothelial cells. Nature. 520, 192-197)] with Itgax-cre (CD11c-cre) mice (Caton, M. L., Smith-Raska, M. R., and Reizis, B. (2007) Notch-RBP-J signaling controls the homeostasis of CD8-dendritic cells in the spleen. J Exp Med. 204, 1653-64) and maintained on a C57BL/6 genetic background. LysM-Cre Cpt1a−/− macrophages were generated from Cpt1a flox/flox mice with LysM-Cre mice and maintained on a C57BL/6 genetic background (Clausen, B. E., Burkhardt, C., Reith, W., Renkawitz, R., and Förster, I. (1999) Conditional gene targeting in macrophages and granulocytes using LysMcre mice. Transgenic Res. 8, 265-77). Mice were bred under specific pathogen-free conditions at the animal facility of the Helmholtz Centre for Infection Research (HZI, Braunschweig, Germany) or at TWINCORE (Hannover, Germany). WT control and CPT1a−/− BMDMs were isolated and differentiated as described above. Cpt2−/− BMDMs were generated as previously described (Gonzalez-Hurtado, E., Lee, J., Choi, J., Selen Alpergin, E. S., Collins, S. L., Horton, M. R., and Wolfgang, M. J. (2017) Loss of macrophage fatty acid oxidation does not potentiate systemic metabolic dysfunction. Am. J. Physiol. Endocrinol. Metab. 312, E381-E393; Nomura, M., Liu, J., Rovira, I. I., Gonzalez-Hurtado, E., Lee, J., Wolfgang, M. J., and Finkel, T. (2016) Fatty acid oxidation in macrophage polarization. Nat. Immunol. 17, 216-7).

Peritoneal macrophages Male mice were euthanized with CO2 and abdominal skin was retracted to expose the intact peritoneal wall. 5 mL of ice-cold PBS with 2 mM EDTA and 2% FCS (Biochrom) were injected into the peritoneal cavity using a syringe with a 20-G needle. The fluid was then aspirated from the peritoneal cavity using the same syringe and collected in a 15 mL tube, and the procedure was repeated twice to obtain a final volume of 10 mL. The cell suspension was centrifuged for 7 min at 400 g at 4° C., and pellets were incubated with anti-CD16/CD32 (homegrown) for 5 min on ice to prevent non-specific antibody binding. A staining cocktail containing the following antibodies was then added: anti-F4/80 eF660, anti CD11b-FITC, anti-CD19 eF450, anti NK1.1 eF450, anti CD3 eF450. After 20 min of incubation on ice, cells were washed and stained with DAPI for dead cell exclusion. Cells were sorted at the MHH cell sorting facility using a MoFlo XDP (Beckman-Coulter) with a 100 μm nozzle. Peritoneal macrophages were gated as DAPI-Lin (CD3, CD19, NK1.1)-, F4/80+, CD11b+.

Rat Primary Cell Cultures

Rat cortical neurons (Kushnareva, Y. E., Wiley, S. E., Ward, M. W., Andreyev, A. Y., and Murphy, A. N. (2005) Excitotoxic injury to mitochondria isolated from cultured neurons. J Biol. Chem. 280, 28894-902) and cortical astrocytes (Kim, H. J. and Magrané, J. (2011) Isolation and culture of neurons and astrocytes from the mouse brain cortex. Methods Mol Biol. 793, 63-75) were prepared according to established methods. Primary cultures of cortical neurons were prepared from embryonic day 18 (E18) Sprague Dawley rats without determination of sex. The cerebral cortices were collected and triturated gently (3-4 times) in ice-cold Hibernate E (Gibco) medium with 1× B27 supplement (Invitrogen), 100 Um' penicillin, and 100 μg/ml streptomycin. After the tissue settled, the Hibernate E medium was aspirated and the tissue was triturated for approximately 2 min in trypsin [0.1% (w/v); Sigma-Aldrich] in Ca2+/Mg2+-free phosphate-buffered saline solution (PBS) supplemented with glucose (5 mM). After these 2 min, trypsin was inactivated by addition of soybean trypsin inhibitor (0.1 mg/mL; Sigma-Aldrich). The mixture was transferred into Hibernate E medium containing 20 U/mL DNAse (Promega) in 0.2× reaction buffer (Promega) and the cells were centrifuged at 200 g for 1.5 min. The supernatant was quickly aspirated and the cells were resuspended in 10 mL Neurobasal (E) medium (Invitrogen) plus glutamate (0.4 m/mL), 0.5 mM L-glutaMAX, penicillin (100 U/mL), streptomycin (100 μg/mL), 1× B27 supplement, and 5 mM sodium pyruvate. Once in suspension, the cells were diluted into 30-45 mL of the same medium without pyruvate (plating medium) and the number of viable cells was determined by trypan blue exclusion using a Countess Automated Cell Counter (Thermo Fisher). Cells were plated on poly-D-lysine coated Agilent Seahorse XF96 plates at a concentration of 3×104 cells in a volume of 100 μL per well. Cells were maintained at 37° C. in a 5% CO2 incubator. After 4 days in vitro, the initial plating medium was diluted with an equal volume of maintenance medium of the same composition lacking glutamate and supplemented with 2 mM GlutaMAX (Thermo Fisher). Half the medium was replaced every 3-4 days. All experiments were performed with cultures that were 13-15 days in vitro.

For primary cortical astrocytes, cortices were collected from E18 Sprague Dawley rat embryos without determination of sex. Cortical pieces were then pushed through a Corning 100 μm cell strainer into a sterile 50 mL centrifuge tube using a sterile glass rod, and the strainer was washed with 8 mL of glial culture medium [DMEM supplemented with 10% FBS, 2 mM GlutaMAX, penicillin (100 U/mL), and streptomycin (100 m/mL)]. This suspension was then filtered through a Corning 70 μm cell strainer. After centrifugation at 800 g, the supernatant was aspirated, and the cells were resuspended with glia culture media, counted, and seeded in T-75 culture flasks at 3×105 cells/cm2. Medium was replaced the following day, and after 7-9 days the cultures were washed, the solid caps were tightened, and then removed by hand-shaking the flasks followed by five washes of the monolayers. Cells were then trypsinized, counted, and plated in glial culture medium in Agilent Seahorse XF96 plates and kept at 37° C. in a 5% CO2 incubator for 24-48 hr prior to experiments.

Neonatal rat ventricular myocytes (NRVMs) were isolated according to established methods (Rubio, M., Avitabile, D., Fischer, K., Emmanuel, G., Gude, N., Miyamoto, S., Mishra, S., Schaefer, E. M., Brown, J. H., and Sussman, M. A. (2009) Cardioprotective stimuli mediate phosphoinositide 3-kinase and phosphoinositide dependent kinase 1 nuclear accumulation in cardiomyocytes. J Mol Cell Cardiol. 47, 96-103). Briefly, NRVMs were isolated from Sprague-Dawley rat hearts (2-3 days old; mixed gender) by several rounds of digestion with collagenase type I (Worthington) and pancreatine (Sigma). Cell suspensions were pre-plated for 2 hours on 10 cm2 dishes in DMEM supplemented with 15% (v/v) FBS, 2 mM GlutaMAX, 100 Um' penicillin, and 100 μg/ml streptomycin to reduce fibroblast contamination. Non-adherent cells were harvested, centrifuged (400 g for 3 min), and plated in gelatin-coated Seahorse XF96 plates in DMEM with 15% (v/v) FBS, 2 mM GlutaMAX, 100 U/ml penicillin, and 100 μg/ml streptomycin. After 24 hr., serum-containing medium was replaced with DMEM lacking FBS but supplemented with GlutaMAX, penicillin, and streptomycin and kept 24-48 hrs. before experiments were conducted. Cells were maintained at 37° C. in a 5% CO2 incubator.

Cultured Cell Lines

All cultured cells were obtained from American Type Culture Collection (ATCC) and cultured as suggested by the supplier. Cell lines were maintained in the medium listed parenthetically: HepG2 [MEM (Gibco 11095)], A549 [DMEM/F12 (Gibco 11330)], and HCT116 [DMEM (Gibco 11965)]. Each formulation of medium was supplemented with 10% (v/v) fetal bovine serum (FBS), 2 mM GlutaMAX, 100 U/mL penicillin, and 100 μg/mL streptomycin. Cells were maintained at 37° C. in a humidified 5% CO2 incubator.

Mitochondrial Isolation

Mouse liver mitochondria were isolated according to standard techniques (Rogers, G. W., Brand, M. D., Petrosyan, S., Ashok, D., Elorza, A. A., Ferrick, D. A., and Murphy, A. N. (2011) High throughput microplate respiratory measurements using minimal quantities of isolated mitochondria. PLoS One. 6, e21746). The liver from a male mouse was minced and rinsed several times in MSHE [70 mM sucrose, 210 mM mannitol, 5 mM HEPES (pH 7.2), and 1 mM EGTA with 0.5% (w/v) fatty acid-free BSA] to remove blood. Tissue was disrupted using a drill-driven Teflon-on-glass Dounce homogenizer (between 2-4 strokes). The homogenate was centrifuged at 800 g for 10 min and the supernatant was filtered through cheesecloth and centrifuged at 8000 g for 10 min. The light layer from the pellet was removed and the remaining pellet was resuspended, centrifuged again, and resuspended in a minimal volume of MSHE. Respirometry All respirometry studies were conducted in either a Seahorse XF96 or XFe96 Analyzer. All experiments were conducted at 37° C., and at pH 7.4 (intact cells) or 7.2 (permeabilized cells and isolated mitochondria). Calculation of respiratory parameters was made according to standard protocols (Divakaruni, A. S., Paradyse, A., Ferrick, D. A., Murphy, A. N., and Jastroch, M. (2014a) Analysis and interpretation of microplate-based oxygen consumption and pH data. Meth. Enzym 547, 509-54), and all rates were corrected for non-mitochondrial respiration/background signal by subtracting the oxygen consumption rate insensitive to rotenone plus antimycin A.

Intact Cells

Palmitate oxidation in intact cells (FIG. 1A, FIG. 1B) was assessed by measuring palmitate-driven respiration that was sensitive to low concentrations of etomoxir (Rogers, G. W., Nadanaciva, S., Swiss, R., Divakaruni, A. S., and Will, Y. (2014) Assessment of fatty acid beta oxidation in cells and isolated mitochondria. Curr. Protoc. Toxicol. 60, 25.3, 1-19). Cells were plated at either $3 \times 10^4$ cells/well (HepG2) or $1.5 \times 10^4$ cells/well (A549) for 48 hr. prior to the assay. 24 hr after plating, standard maintenance medium was replaced with a substrate-limited medium to deplete endogenous nutrient stores and prime cells for fatty acid oxidation. This substrate-limited medium was DMEM (Gibco A14430) supplemented with 0.5 mM glucose, 1% (v/v) FBS, 0.5 mM carnitine, 1 mM GlutaMAX, 100 U/mL penicillin, and 100 µg/mL streptomycin. On the day of the assay, the substrate-limited medium was replaced with assay medium composed of unbuffered DMEM (Sigma #D5030) supplemented with 0.2% (v/v) BSA-conjugated palmitate ([FFA≥50 nM]; Seahorse XF Palmitate-BSA FAO Substrate, Agilent Technologies), 2.5 mM glucose, 0.5 mM carnitine, and 2 mM HEPES. Respiration was measured under basal conditions as well as after injection of 2 µM oligomycin, two sequential additions of 1 µM FCCP, followed by 0.2 µM rotenone with 1 µM antimycin A. Etomoxir was added to the assay medium 30 min. prior to measurements of basal respiratory rates.

Respiration in intact BMDMs was measured in medium containing 8 mM glucose, 2 mM glutamine, 2 mM pyruvate, and 5 mM HEPES. Cells were plated at $5.0 \times 10^4$ cells/well and assayed after 48 hr. When measuring the response to IL-4, cells were treated with 20 ng/mL of IL-4 24 hr. after initial plating, and respiration was measured the following day (~48 hr after initial seeding). Respiration was measured in response to oligomycin (1 µM), FCCP (1.2 µM), and rotenone (0.2 µM) with antimycin A (1 µM).

When diagnosing an off-target effect of etomoxir (FIG. 5A, FIG. 5B, FIG. 5C), all cells apart from primary neurons were offered 8 mM glucose, 2 mM glutamine, and 2 mM pyruvate in unbuffered DMEM supplemented with 5 mM HEPES. Cells were plated at the following densities: A549 ($1.2 \times 10^4$ cells/well for 48 hr), HCT116 ($1.5 \times 10^4$ cells/well for 48 hr.), cortical neurons ($3.0 \times 10^4$ cells/well and assayed at day in vitro 13-15), cortical astrocytes (plated at $2.0 \times 10^4$ cells/well for 24 or 48 hr.), BMDM (plated at $5.0 \times 10^4$ cells/well for 48 hr), and NRVM (plated at $5.0 \times 10^4$ cells/well for 48 hr.). Primary neurons were assayed in artificial cerebrospinal fluid [aCSF; 120 mM NaCl, 3.5 mM KCl, 1.3 mM CaCl2, 0.4 mM KH2PO4, 1 mM MgCl2, 5 mM HEPES (pH 7.4)] and offered 10 mM glucose and 1 mM pyruvate as respiratory substrates. Respiration in all intact cells was measured in the basal state as well as in response to 2 µM oligomycin, FCCP (either 400 nM, 800 nM or 1.2 µM as appropriate and previously optimized), and 0.2 µM rotenone with 1 µM antimycin A. Etomoxir (at concentrations indicated in the text), UK5099 (3 µM), or BPTES (3 µM) were added to the assay medium 30 min prior to measurements.

Permeabilized Cells

The plasma membrane of cells was selectively permeabilized with recombinant, mutant perfringolysin O [rPFO; commercially XF Plasma Membrane Permeabilizer (XF PMP, Agilent Technologies, Divakaruni, A. S., Wiley, S. E., Rogers, G. W., Andreyev, A. Y., Petrosyan, S., Loviscach, M., Wall, E. A., Yadava, N., Heuck, A. P., Ferrick, D. A., et al. (2013) Thiazolidinediones are acute, specific inhibitors of the mitochondrial pyruvate carrier. Proc. Natl. Acad. Sci. USA 110, 5422-7]. Experiments were conducted essentially as previously described except medium lacked BSA to align with intact cell experiments and avoid binding of etomoxir by BSA (Divakaruni, A. S., Rogers, G. W., and Murphy, A. N. (2014). Measuring mitochondrial function in permeabilized cells using the Seahorse XF Analyzer of a Clark-type oxygen electrode. Curr. Prot. Tox. 60, 25.2, 1-16). Immediately prior to assay, cell media was replaced with MAS buffer (70 mM sucrose, 220 mM mannitol, 10 mM KH2PO4, 5 mM MgCl2, 2 mM Hepes, and 1 mM EGTA; pH 7.2) containing 3 nM rPFO, respiratory substrates, and 4 mM ADP. The ADP-stimulated respiration rate (referred to interchangeably as 'phosphorylating' or 'State 3' respiration) was measured, and rates were subsequently measured in response to 2 µM oligomycin, sequential additions of 400 nM FCCP, and 0.2 µM rotenone with 1 µM antimycin A. Substrate concentrations were as follows: Glu, 5 mM glutamate with 5 mM malate; Pyr, 10 mM pyruvate with 1 mM malate; PCoA, 40 µM palmitoyl CoA with 1 mM malate and 0.5 mM carnitine; Pcarn, 40 µM palmitoylcarnitine with 1 mM malate; Gln 5 mM glutamine (no malate was necessary for glutamine oxidation in permeabilized A549 cells); Succ, 10 mM succinate with 2 µM rotenone.

Figure 6A:
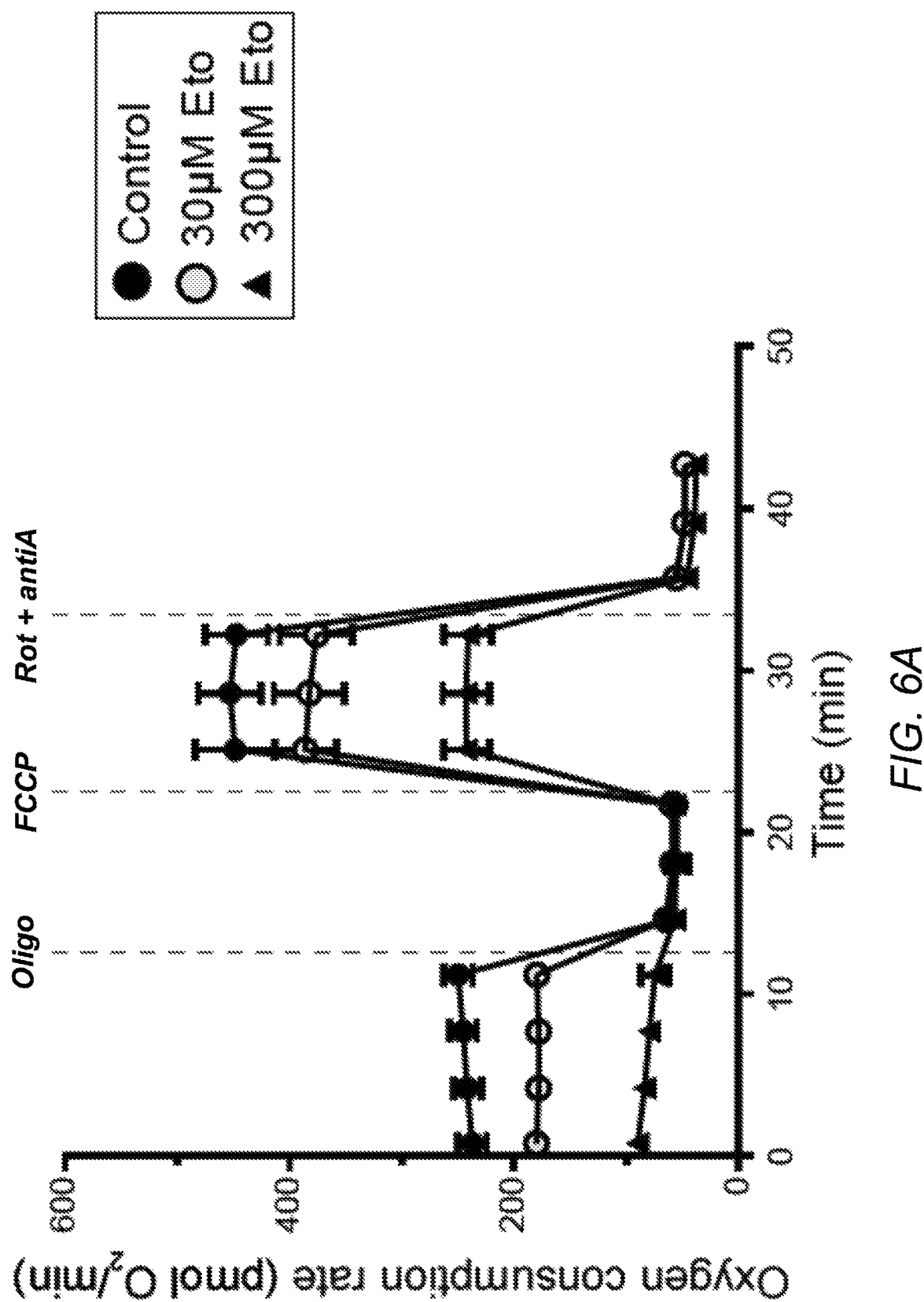
Figure 6B:
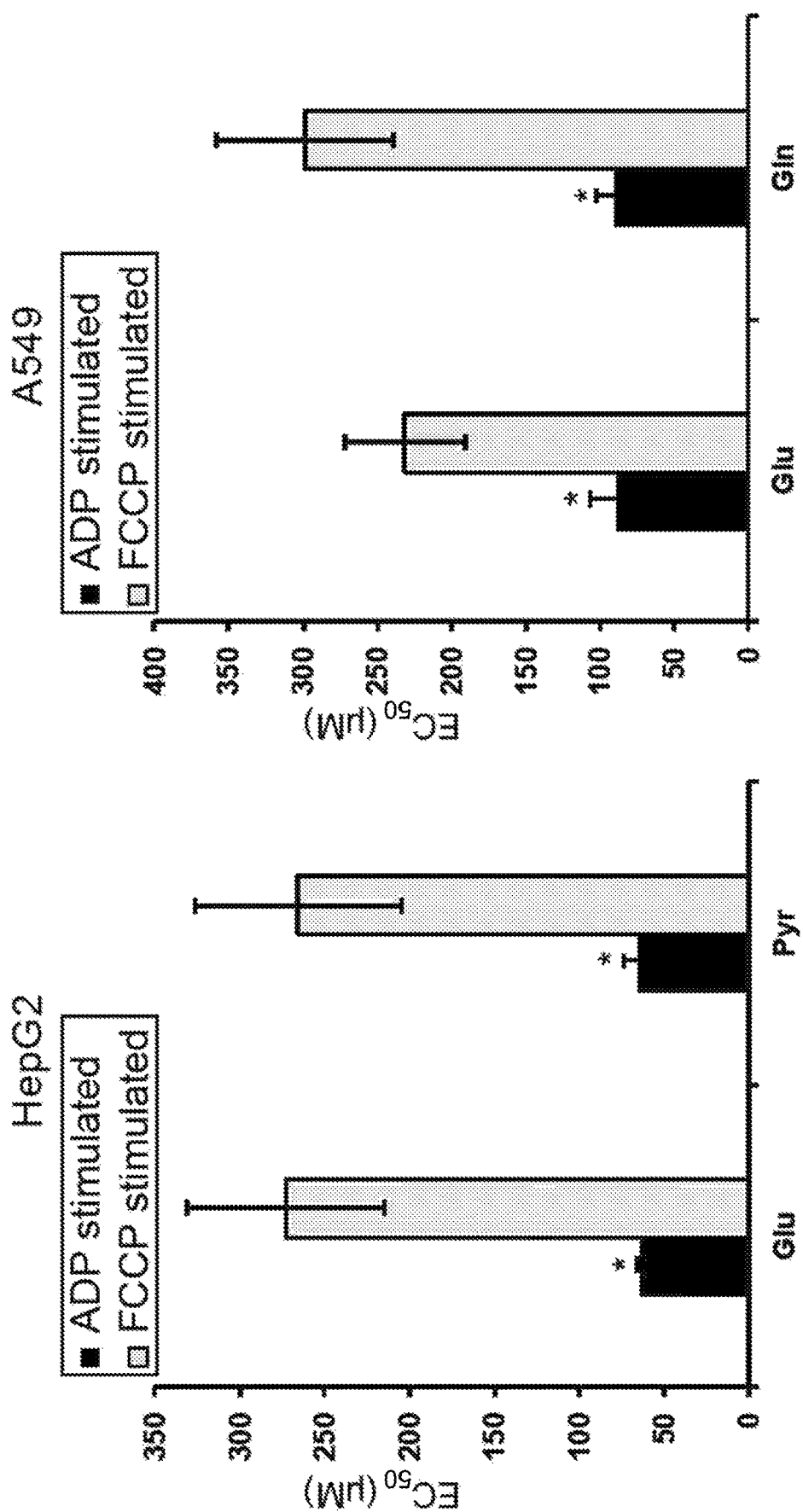
Figure 6C:
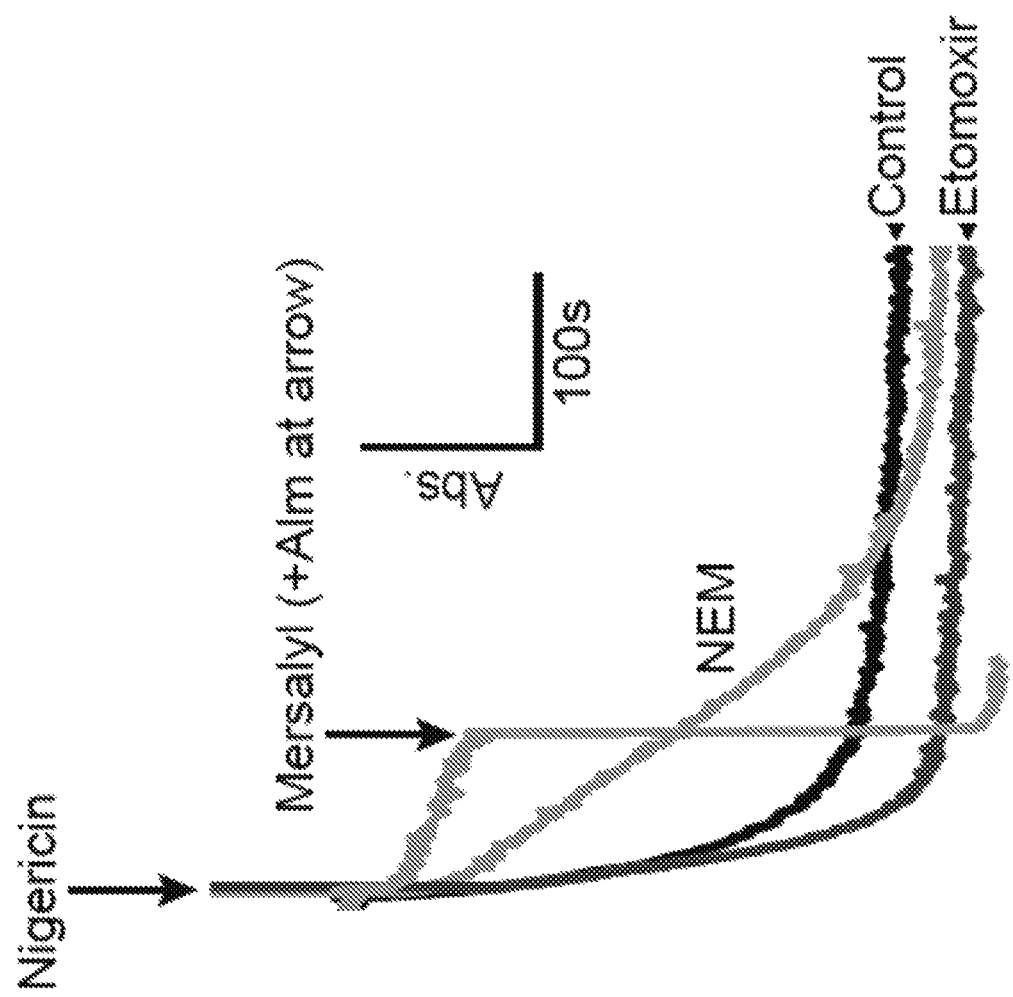

When assessing the effects of etomoxir on specific oxidative pathways in permeabilized cells (FIG. 1F), cells were pre-treated for 30 min in intact cell assay medium prior to permeabilization to allow formation of etomoxiryl-CoA, the active inhibitor of CPT-1. Etomoxiryl-CoA is an irreversible inhibitor of CPT-1, so the inhibition of the enzyme persists through medium changes and cell permeabilization. To measure the off-target effect of etomoxir in isolated mitochondria and permeabilized cells (FIG. 4B; FIG. 6A, FIG. 6B), etomoxir was added directly to the MAS medium 15 min prior to initial measurements.

When permeabilized cells were treated with alamethicin to form pores of 3-6 kDa in the mitochondrial inner membrane ("double-permeabilized" cells) and complex I-mediated respiration was directly assessed (FIG. 6F), 10 µg/mL alamethicin was added at 37° C. 15 minutes prior to measurements (Divakaruni, A. S., Andreyev, A. Y., Rogers, G. W., and Murphy, A. N. (2017a) In situ measurements of mitochondrial matrix enzyme activities using plasma and mitochondrial membrane permeabilization agents. Anal. Biochem. 17, 30385-8). Double-permeabilized cells were offered 10 µM cytochrome c in the experimental medium and either 10 mM NADH or 10 mM succinate with 2 µM rotenone to drive respiration.

Isolated Mitochondria

Phosphorylating respiration was measured in isolated liver mitochondria (1.5 µg/well) as previously described (Rogers, G. W., Brand, M. D., Petrosyan, S., Ashok, D., Elorza, A. A., Ferrick, D. A., and Murphy, A. N. (2011) High throughput microplate respiratory measurements using minimal quantities of isolated mitochondria. PLoS One. 6, e21746), and offered 10 mM pyruvate, 1 mM malate, and 4 mM ADP. Uncoupler stimulated respiration was measured after addition of oligomycin (3 ng/mg mitochondrial protein) and FCCP (4 µM). All rates were corrected for background by subtracting the oxygen consumption rate insensitive to 0.5 µM rotenone and 1 µM antimycin A. Etomoxir was acutely added to the experimental medium 15 minutes prior to taking initial measurements.

ATP Hydrolysis

ATP hydrolysis in isolated mitochondria (McQuaker, S. J., Quinlan, C. L., Caldwell, S. T., Brand, M. D., and Hartley, R. C. (2013). A prototypical small molecule modulator uncouples mitochondria in response to endogenous hydrogen peroxide production. Chembiochem. 14, 993-1000; Divakaruni, A. S., Andreyev, A. Y., Rogers, G. W., and Murphy, A. N. (2017a) In situ measurements of mitochondrial matrix enzyme activities using plasma and mitochondrial membrane permeabilization agents. Anal. Biochem. 17, 30385-8) was performed in MAS buffer, and stimulated by respiratory chain inhibition (1 µM rotenone and 2 µM antimycin A) followed by addition of excess ATP (25 mM) and uncoupler (1 µM FCCP). Hydrolysis was inhibited by injection of either oligomycin (3 ng/mg mitochondrial protein) or carboxyatractylo side (7.5 ng/mg mitochondrial protein). Rates of extracellular acidification (ECAR, in mpH/min) were converted to proton production rates (PPR, in pmol H+/min) by determining the buffer capacity with sequential injections of HCl and H2SO4 (Mookerjee, S. A., Goncalves, R. L., Gerencser, A. A., Nicholls, D. G., and Brand, M. D. (2015). The contributions of respiration and glycolysis to extracellular acid production. Biochim et Biophys Acta. 1847, 171-81). 10 µg/mL alamethicin was used to permeabilize the mitochondrial inner membrane (1 µg/mg mitochondrial protein).

Western Analysis

Cells were lysed in Pierce RIPA buffer (Thermo Scientific) supplemented with complete EASYpack Mini Protease Inhibitor Cocktail and PhosSTOP Phosphatase Inhibitor (Roche). Cell lysates were resolved by SDS-PAGE and transferred to PVDF membranes (Merck Millipore). Membranes were incubated with anti-CPT1A (clone 8F6AE9, Abcam) and anti-β-Actin (clone AC-15, Sigma-Aldrich).

9,10-3H-Palmitate Oxidation

BMDMs at day 6 of differentiation were seeded at 3×105 cells/well in 12 well plates in BMDM media. The next day, cells were treated in DMEM containing 25 mM glucose supplemented with 5% FBS, 2 mM L-Glutamax, 100 units/mL, 100 µg/mL penicillin/streptomycin, 1 mM of sodium pyruvate, 1 mM carnitine, and 5% v/v conditioned media containing macrophage colony stimulating factor (M-CSF) under one of 5 conditions: control, 20 ng/mL of IL-4±3 µM or 200 µM of etomoxir, or 200 nM rotenone, or 200 nM antimycin A for 24 hr. Fatty acid oxidation was measured 24 hours later as previously described (Rognstad, R. (1991) Estimation of peroxisomal and mitochondrial fatty acid oxidation in rat hepatocytes using tritiated substrates. Biochem J 279:147-150, 1991; Cha, B. S., Ciaraldi, T. P., Park, K. S., Carter, L., Mudaliar, S. R., and Henry R R. (2005) Impaired fatty acid metabolism in type 2 diabetic skeletal muscle cells is reversed by PPARgamma agonists. Am J Physiol Endocrinol Metab. 289, E151-9) following a fluid change to DMEM with components as described above except 10 mM glucose and 0.2 µCi (final concentration of 5 µM) BSA-conjugated [9,10-3H]palmitic acid. No additional IL-4 was added at the time of this fluid change, but etomoxir, rotenone and antimycin A were added, and the plates were placed in a 95% O2-5% CO2 incubator at 37° C. for 3 hr. After incubation, a 100 µL aliquot of the culture medium was passed over an ion-exchange resin, and the column was washed twice with 0.75 ml of water. Free fatty acids were retained by the resin, whereas the tritium hydrolyzed from radiolabeled palmitate catabolism was released as labeled water, which passes freely through the resin, and is subsequently counted for radioactivity. All data are corrected for protein content in each well. There were 3 technical replicates for each condition, and 4 biological replicates arising from 4 separate animals.

Intracellular Free Coenzyme A Levels

On Day 6 of differentiation, BMDMs were seeded at 1.2×106 cells/well in 6-well plates. 24 hr later, BMDMs were mock-treated or co-treated with 20 ng/mL IL-4±200 µM etomoxir±500 µM CoA in DMEM supplemented with 5% FBS, 2 mM L-glutamine, 100 units/mL, 100 m/mL penicillin/streptomycin, 500 µM of sodium pyruvate and 5% v/v conditioned media containing macrophage colony stimulating factor (M-CSF) for 20 hr. Prior to sample collections, cells were washed with 600 µL of 0.9% (w/v) NaCl twice. Three wells per replicate per treatment were combined in 2 mL centrifuge tubes and centrifuged at 500 g for 5 mins at 4° C. The supernatant was removed, and the cell pellet was re-suspended in 75 µL of ice-cold 0.7% (v/v) perchloric acid for 5 min. Samples were then centrifuged at 10,000 g for 7 mins at 4° C. and the resulting supernatant was adjusted to pH 7 with 2M NaOH and 500 mM K2HPO4. The coenzyme A concentration was determined with Coenzyme A Assay Kit following manufacturer's instructions (Sigma MAK034) using 40 µL of sample supernatant. Coenzyme A levels were normalized to total cellular protein (BCA method).

Arginase Activity

On Day 6 of differentiation, BMDMs were seeded at 1×106 cells/well in 6-well plates. 24 hr later, BMDMs were mock-treated or co-treated with 20 ng/mL IL-4±200 µM etomoxir in DMEM supplemented with 5% FBS, 2 mM L-glutamine, 100 units/mL, 100 µg/mL penicillin/streptomycin, 500 µM of sodium pyruvate and 5% v/v conditioned media containing macrophage colony stimulating factor (M-CSF) for 24 hr. Prior to sample collections, cells were washed with 600 µL of ice-cold PBS twice and scraped into 1.5 mL centrifuge tubes. Cell lysate was prepared according to Arginase Activity Assay Kit (Sigma MAK112) instructions and the 20 µL of lysate was used to measure arginase activity. Arginase activity was adjusted to total cell number.

Lactate Assay

Under conditions matching intact cell respirometry for BMDMs, the extracellular medium was harvested and lactate was analyzed as previously described (Mookerjee, S. A., Goncalves, R. L., Gerencser, A. A., Nicholls, D. G., and Brand, M. D. (2015). The contributions of respiration and glycolysis to extracellular acid production. Biochim et Biophys Acta. 1847, 171-81; Divakaruni, A. S., Wallace, M., Buren, C., Martyniuk, K., Andreyev, A. Y., Li, E., Fields, J. A., Cordes, T., Reynolds, I. J., Bloodgood, B. L., et al., (2017b) Inhibition of the mitochondrial pyruvate carrier protects from excitotoxic neuronal death. J. Cell Biol. 216, 1091-1105). Briefly, the harvested medium was mixed 1:1 with a solution of 40 Um' LDH (Sigma-Aldrich L3916), 1 M Tris, pH 9.8, 20 mM EDTA, 400 mM hydrazine (Sigma-Aldrich 309400), and 4 mM NAD+. The reaction velocity was measured after 2 min (340/460 nm excitation/emission). Values were calibrated against known lactate concentrations (L7022; Sigma-Aldrich).

Cell Counts and Normalization

For BMDM respirometry experiments normalized to cell number, cells were fixed immediately upon completion of the assay with 4% formaldehyde for 20 min at room temperature and kept refrigerated between 1 and 21 days until assessment. The day prior to cell counting, cells were stained with Hoescht 33342 (Thermo Fisher) at 10 ng/mL overnight at 4° C. Cell counts were obtained using the Operetta High Content Imaging System (Perkin Elmer).

Phosphate Transporter Assay

Phosphate transport was measured by monitoring swelling of de-energized mitochondria in isotonic potassium phosphate medium based upon principles described by Coty, W. A. and Pedersen, P. L. (1975) Phosphate transport in rat liver mitochondria. Kinetics, inhibitor sensitivity, energy requirements, and labeled components. Mol Cell Biochem. 9, 109-24. As the phosphate carrier acts as electroneutral symporter with protons, the process is self-restricting due to generation of an opposing pH gradient. The restriction is relieved, and the full rate of phosphate transport revealed with addition of the chemical potassium/proton antiporter, nigericin. In the presence of nigericin, the proton fluxes cycle resulting in electro- and pH-neutral transport of potassium phosphate down its concentration gradient into the mitochondrial matrix, resulting in osmotic accumulation of water. Under these conditions, transport is limited by the activity of phosphate carrier, and can be recorded as mitochondrial swelling (a decrease in light scattering).

The measurements were performed in an LS-50B spectrofluorometer (Perkin-Elmer) at 540 nm. Assay medium contained 125 mM potassium phosphate, pH 7.2, 0.5 mM EGTA, and 2 µM rotenone. Mouse liver mitochondria (0.5 mg/ml) were treated with 250 µM etomoxir, 100 µM N-ethylmaleimide (NEM) (Klingenberg, M., Durand, R., and Guerin, B. (1974) Analysis of the reactivity of SH-reagents with the mitochondrial phosphate carrier. Eur J Biochem, 42, 135-150) or 10 µM mersalyl (Paradies, G. and Ruggiero, F. M. (1991) Effect of aging on the activity of the phosphate carrier and on the lipid composition in rat liver mitochondria. Arch Biochem Biophys. 284, 332-337) and the reaction was started with 5 µM nigericin. Typical traces from 3 experiments are shown. To establish the maximally swollen state of mitochondria, 80 µg/ml alamethicin was used.

Mitochondrial Effector Treatments for qPCR and Flow Cytometry

For all gene expression and flow cytometry experiments described below, day 6 BMDM were plated at 3×10$^5$ cell/well in 12-well plates. The next day, cells were treated with appropriate compounds (and duration as indicated in figures and below) in DMEM supplemented with 5% FBS, 2 mM L-glutamine, 100 units/mL, 100 µg/mL penicillin/streptomycin, 500 µM of sodium pyruvate and 5% v/v conditioned media containing macrophage colony stimulating factor (M-CSF).

For flow cytometry experiments involving etomoxir (FIG. 1G, FIG. 2A, FIG. 2D, FIG. 3A, FIG. 3B, FIG. 3G, FIG. 3H): BMDMs were mock-treated (media replacement only) or treated with 20 ng/mL of IL-4±3 µM or 200 µM of etomoxir for 48 hr. When measuring expression of M(IL-4)-associated genes in response to etomoxir (FIG. 1H, FIG. 2B), BMDMs were mock-treated or treated with 20 ng/mL of IL4±etomoxir as indicated for 24 hr.

Figure 4A:
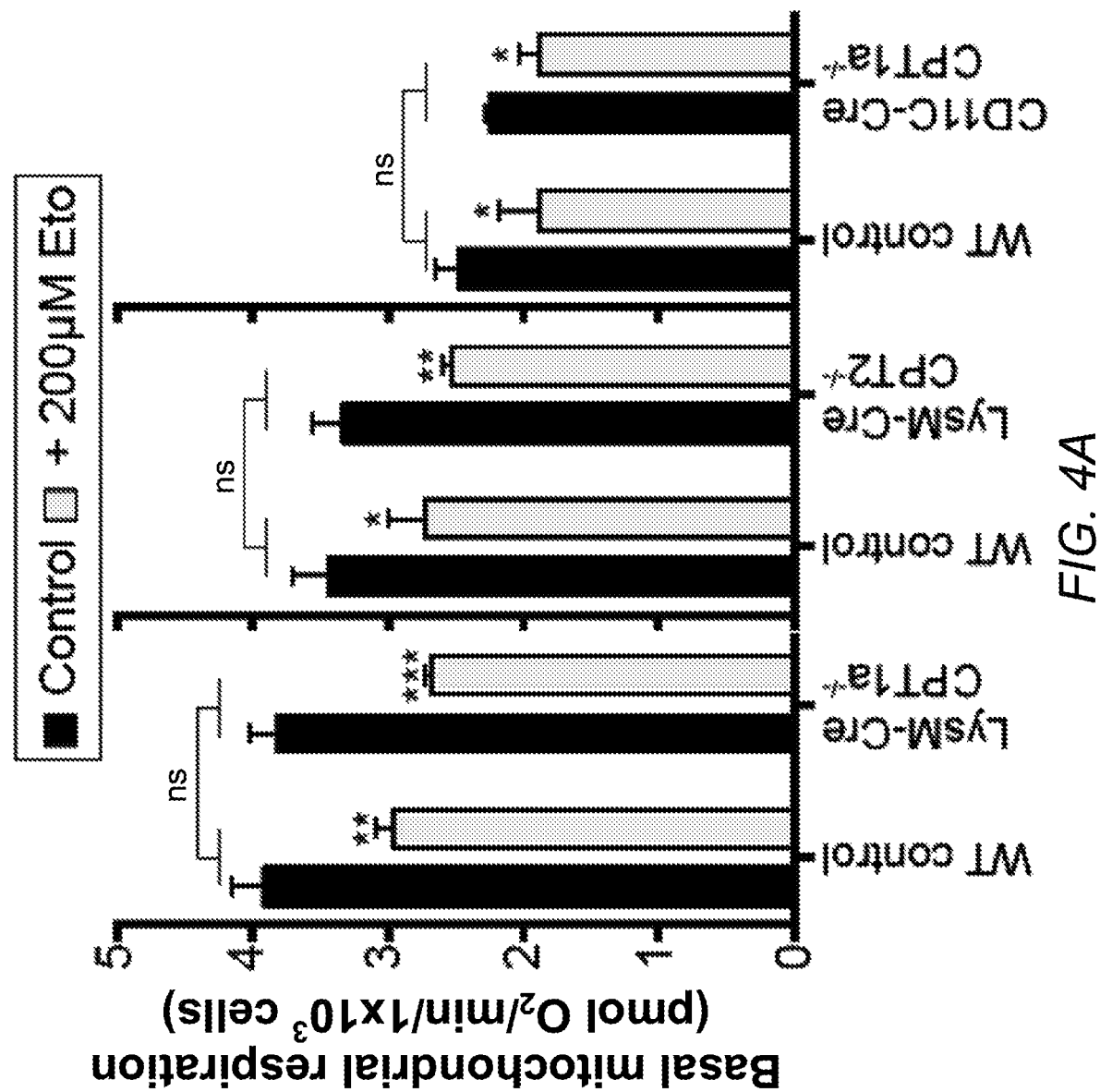
Figure 4B:
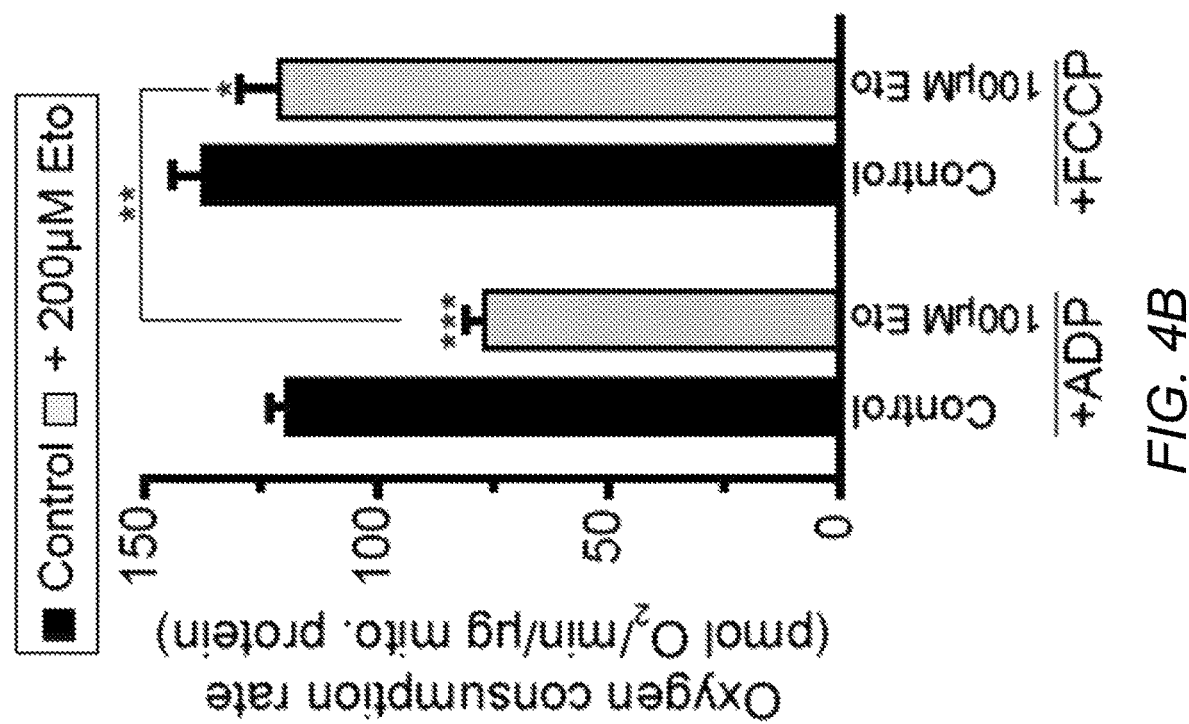
Figure 4C:
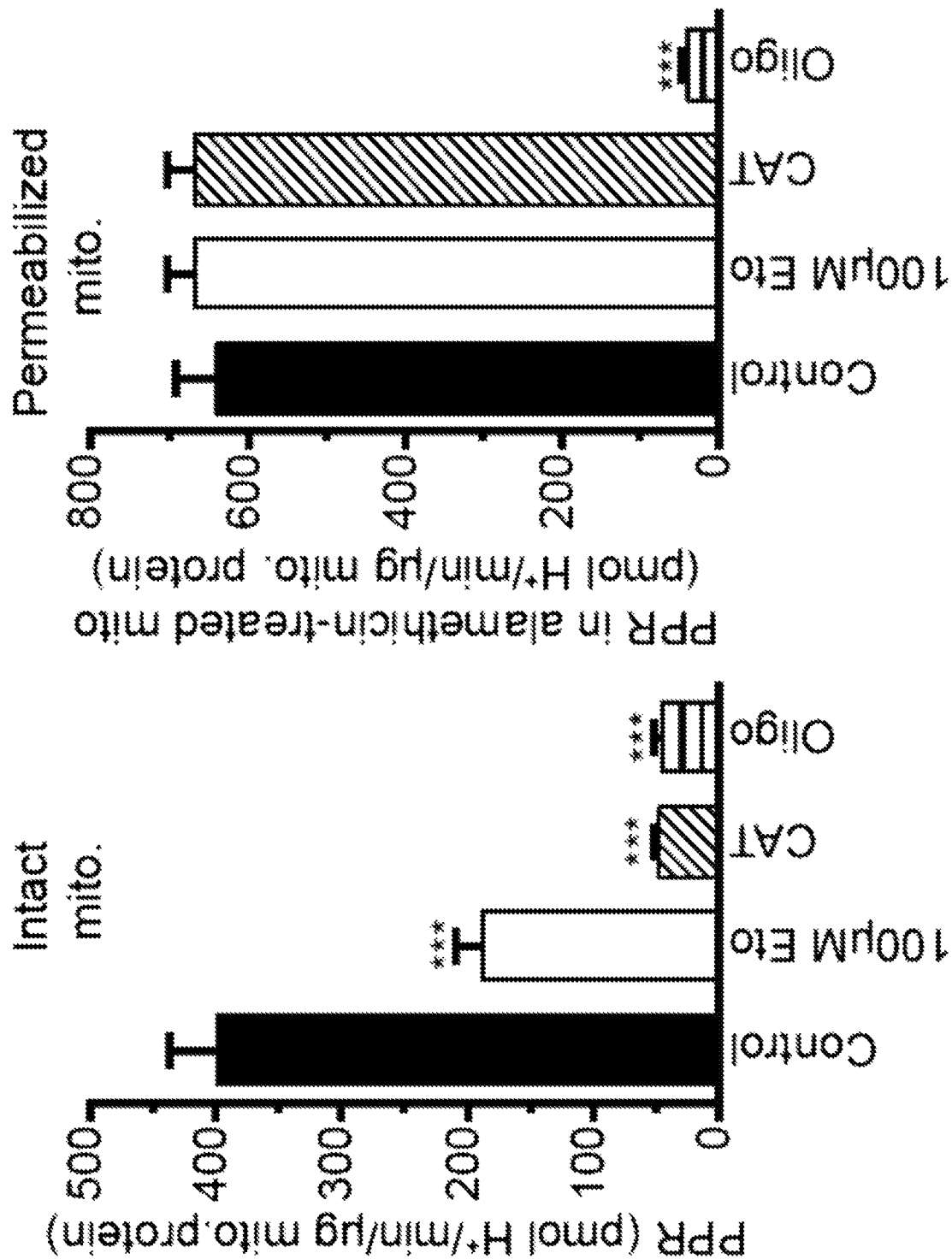
Figure 4D:
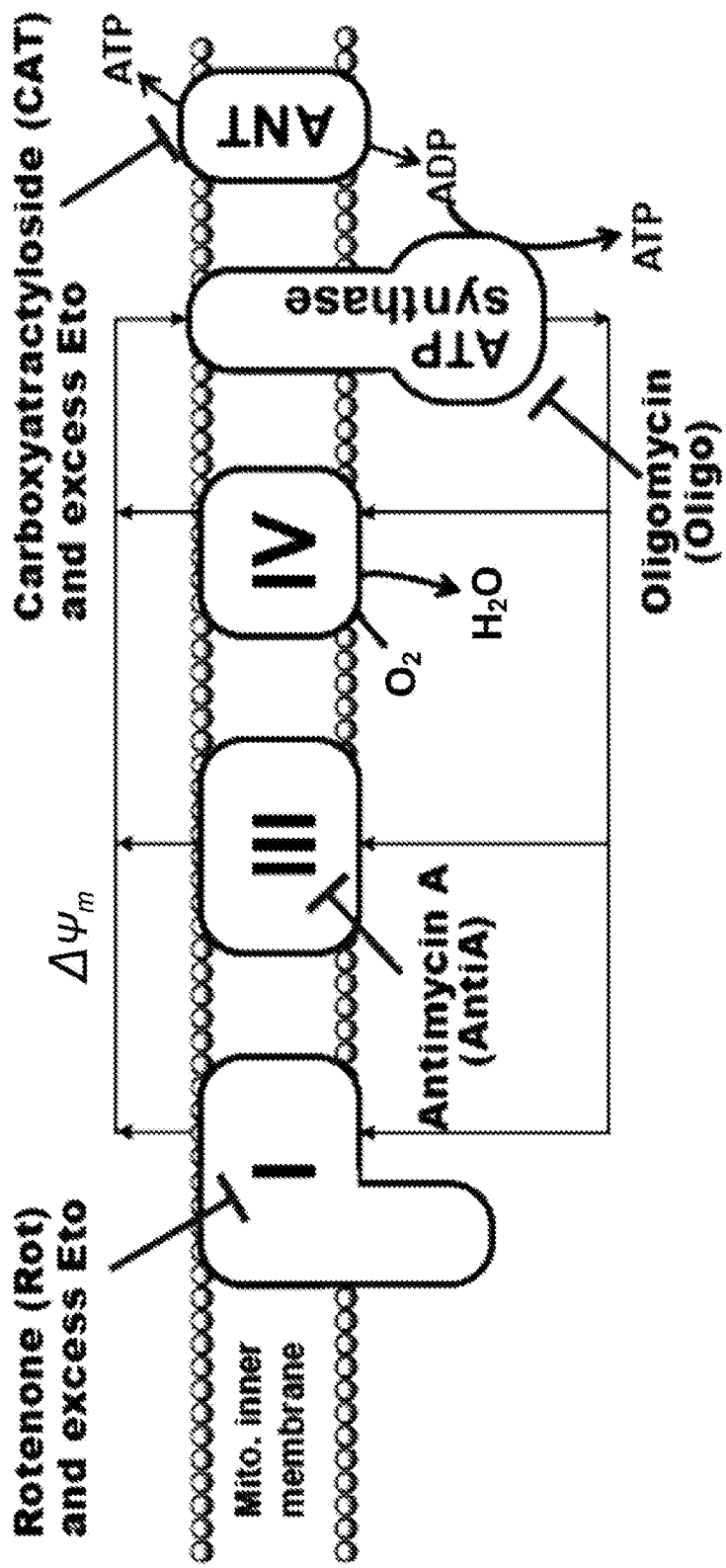
Figure 4E:
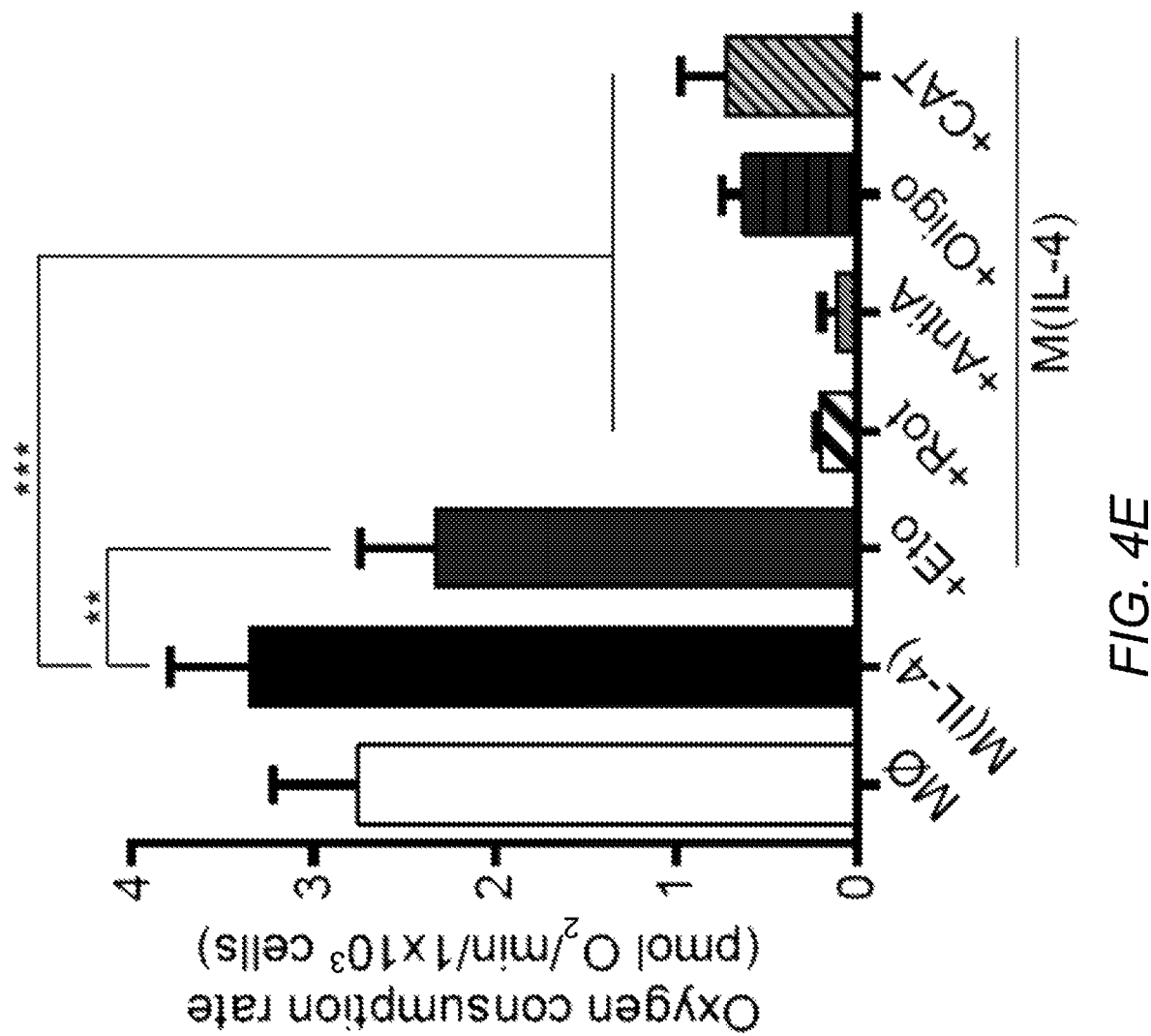
Figure 4F:
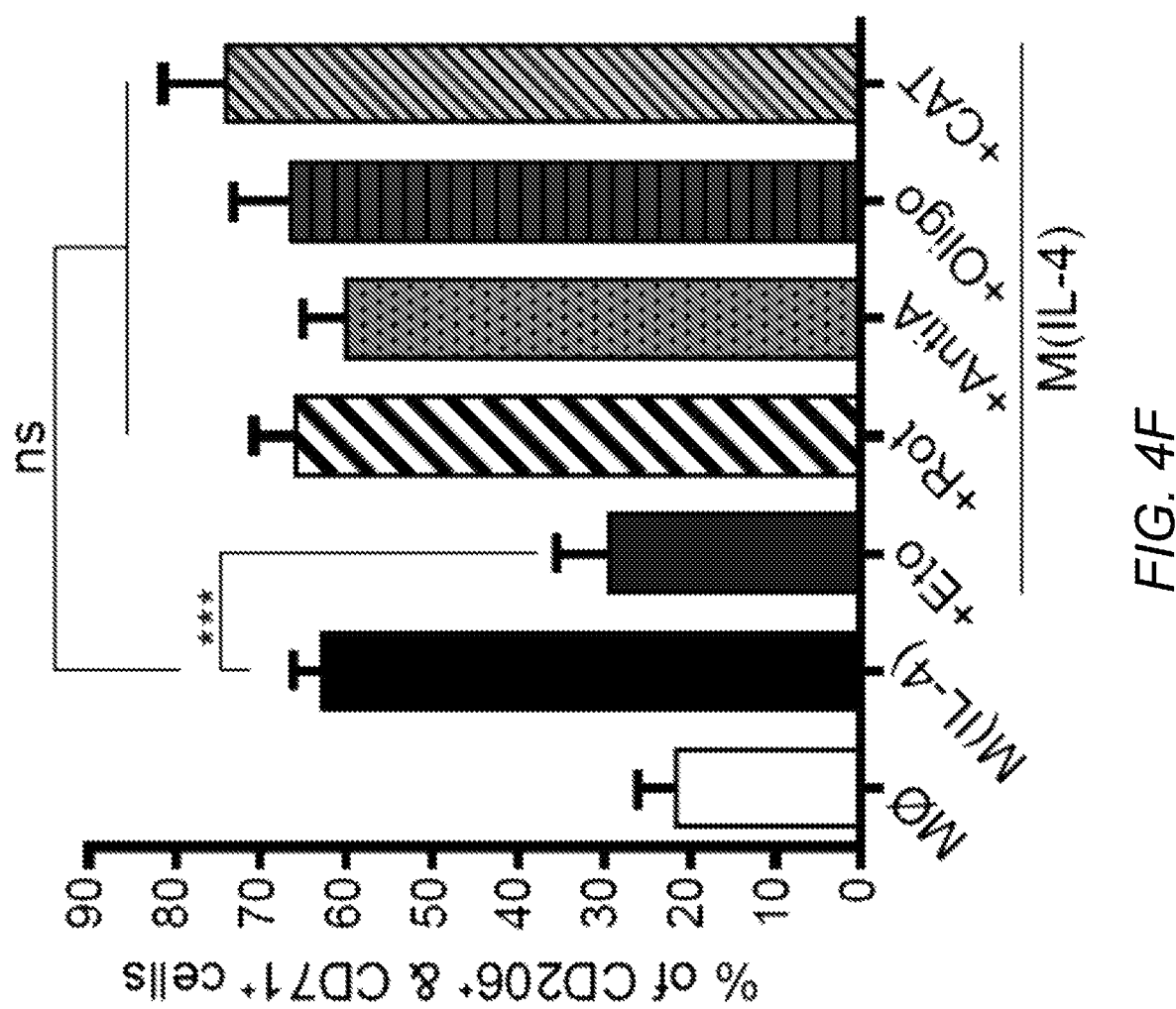
Figure 6G:
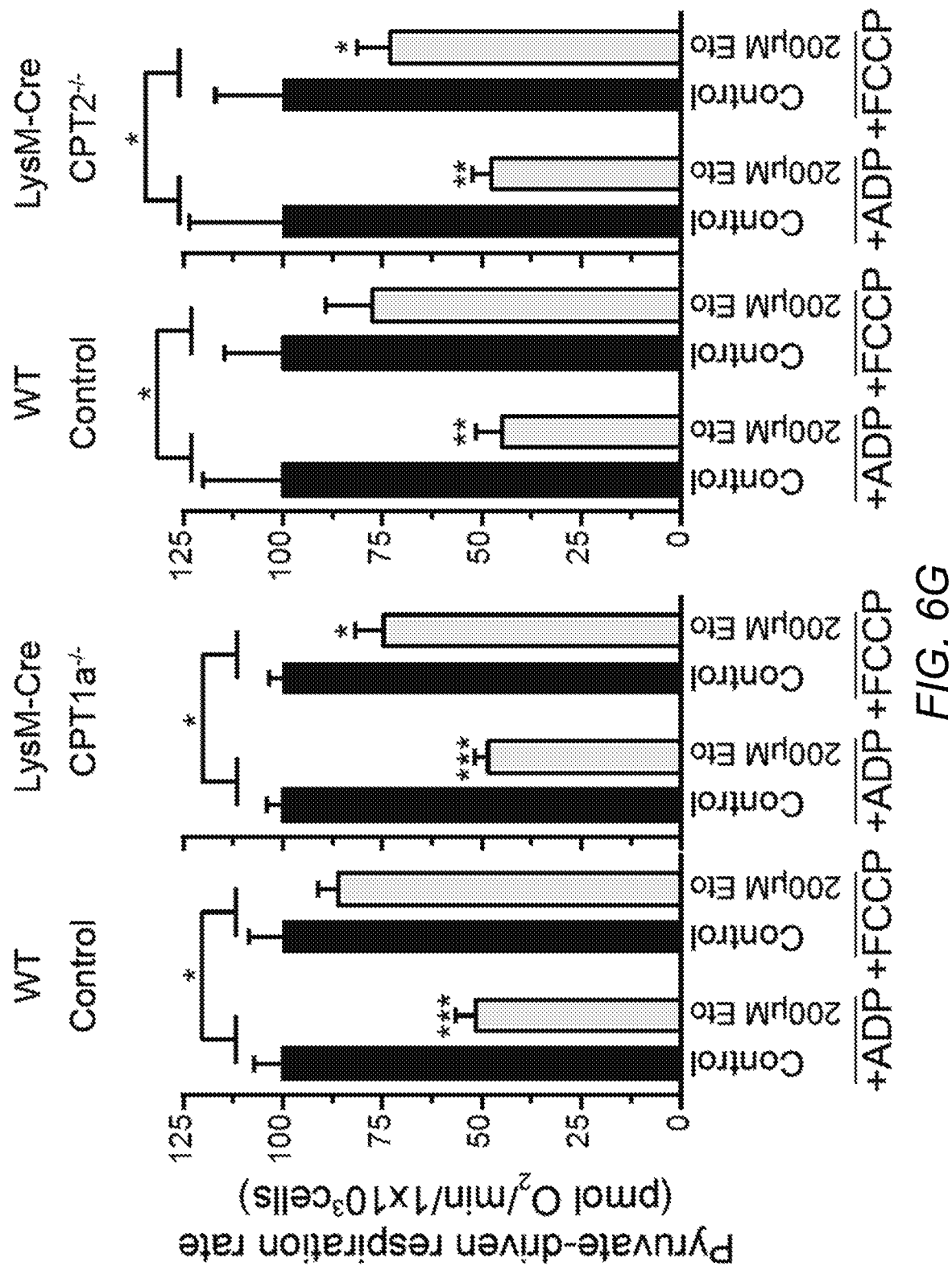
Figure 6G:
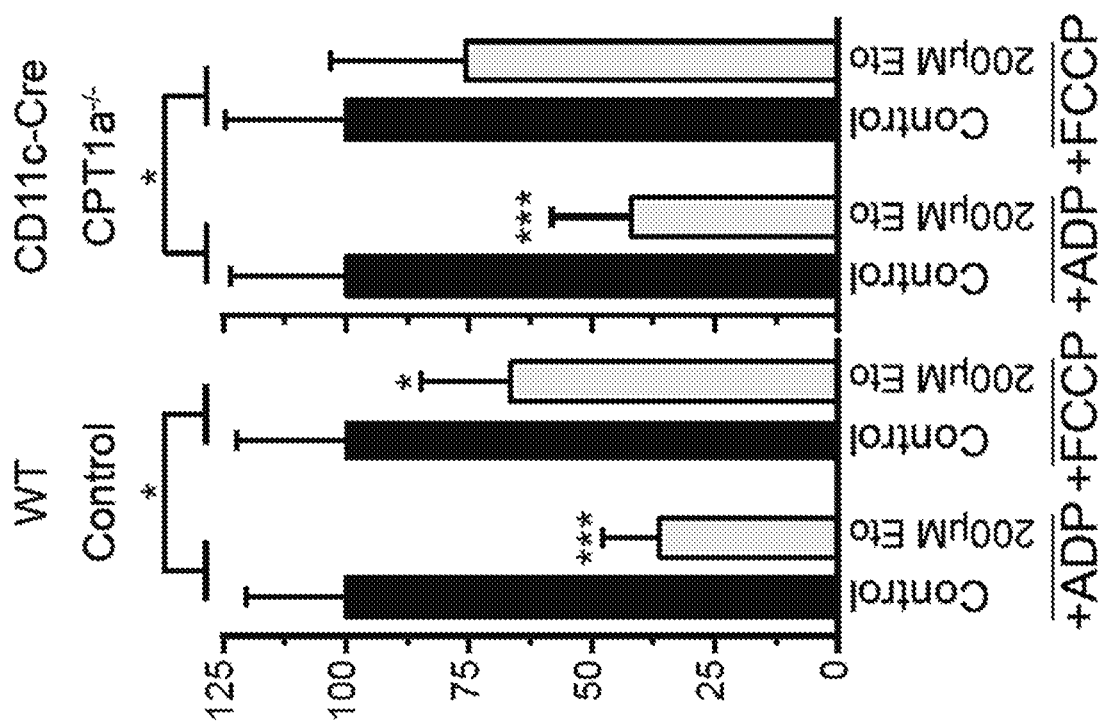
Figures 7A, 7B:
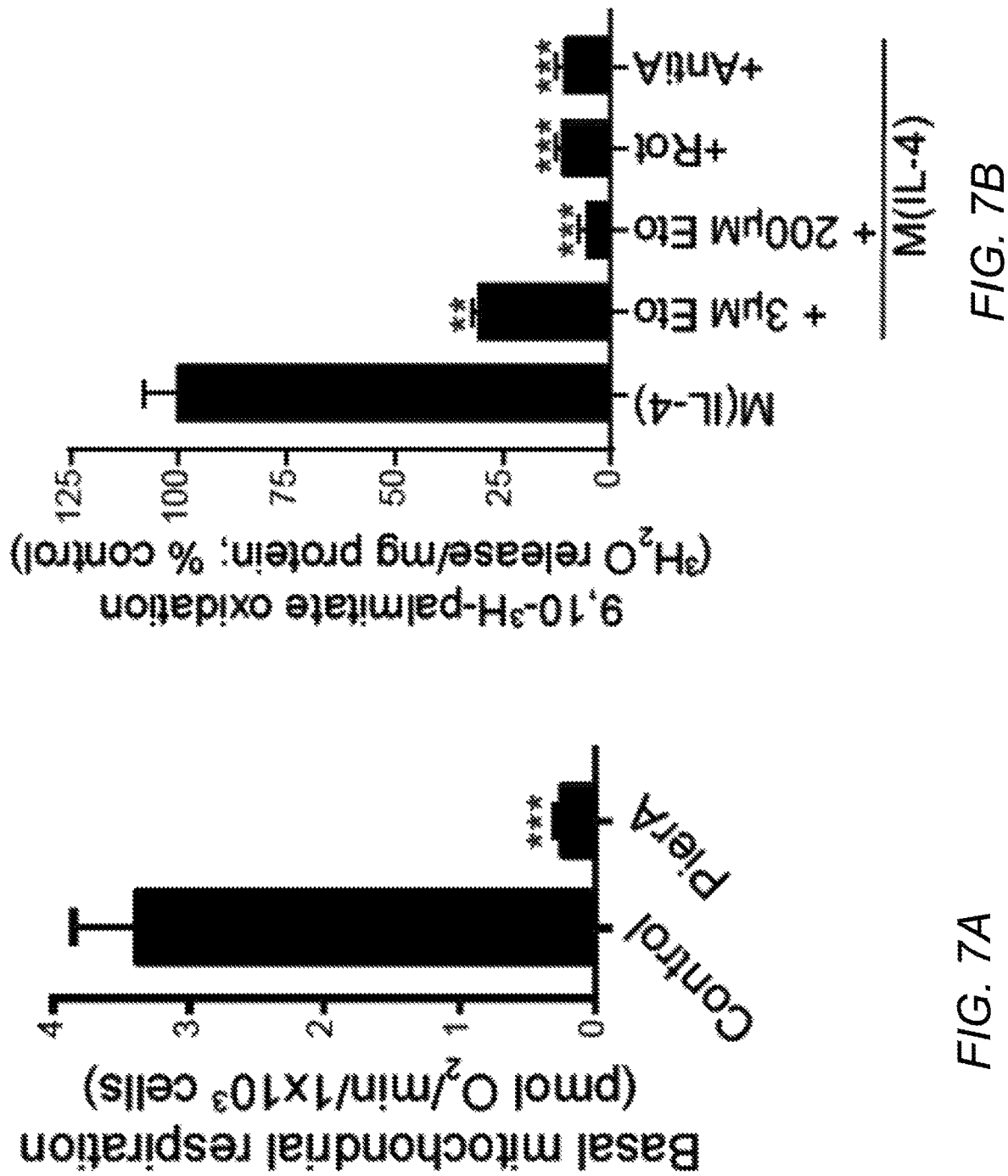
Figure 7C:
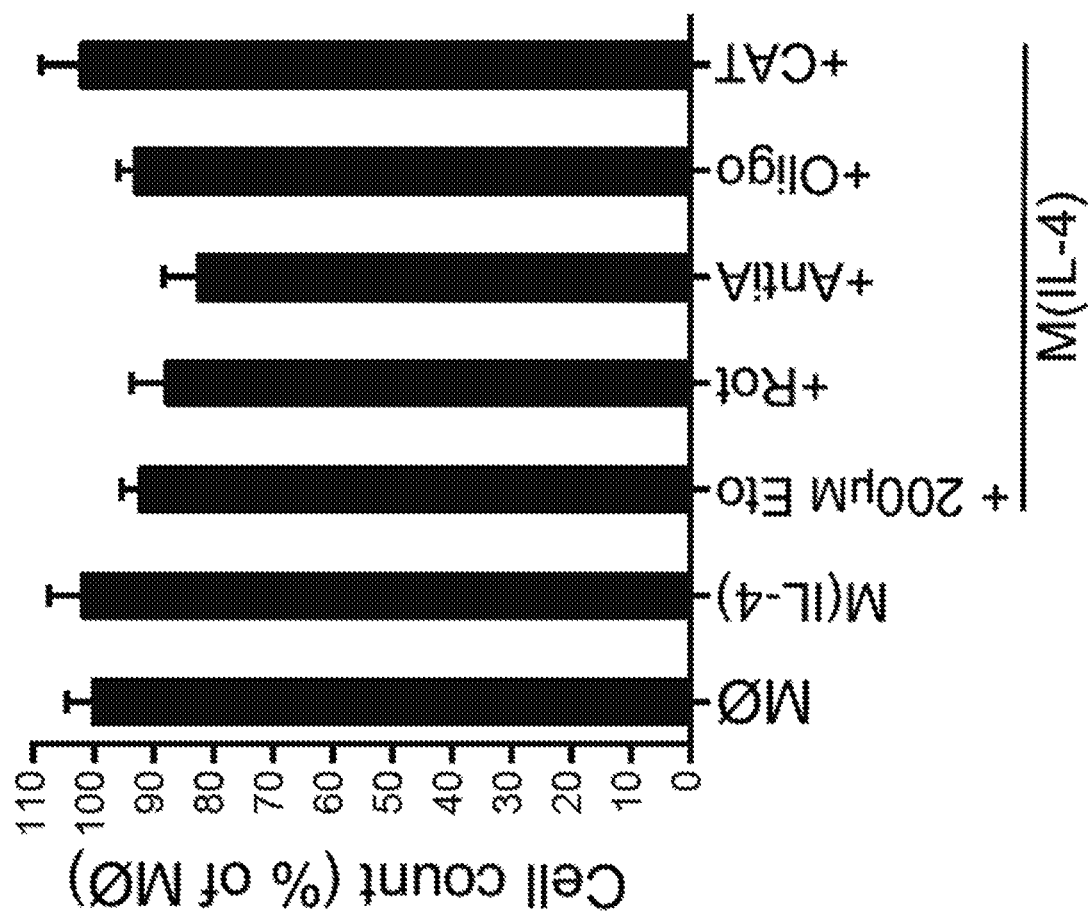
Figure 7D:
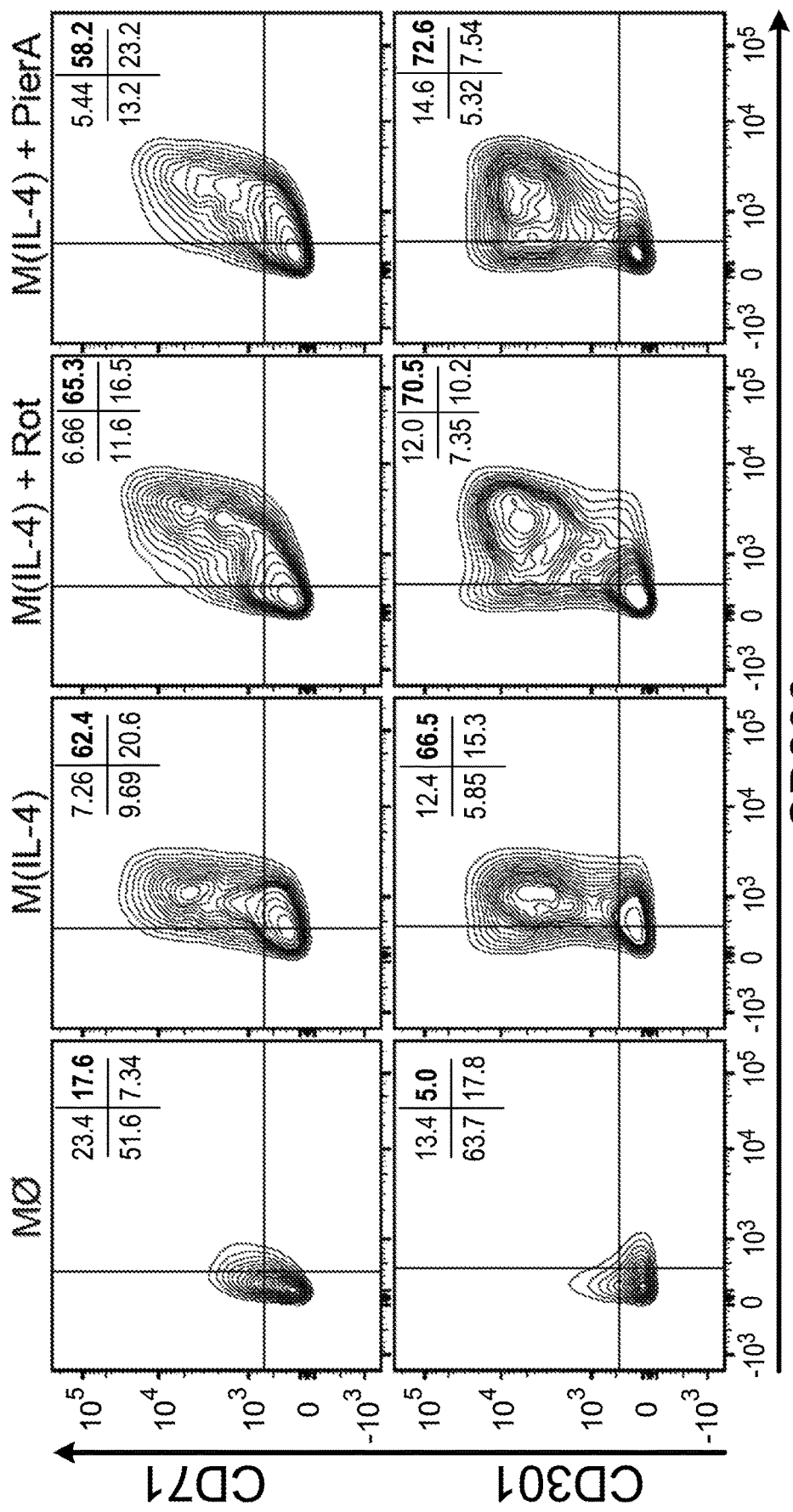

For experiments involving respiratory chain inhibitors: BMDMs were mock-treated (media replacement only) or treated with 20 ng/mL of IL4±1.2 µM oligomycin (Oligo), 200 nM rotenone (Rot), 200 nM antimycin A (AntiA), 100 nM piericidin A (PierA), or 5 µM carboxyatractylate (CAT) for either 24 (FIG. 4G, FIG. 4H, FIG. 6G) or 48 hr (FIG. 4F, FIG. 7D). All inhibitors were given as co-treatments simultaneously with IL-4.

For experiments involving CoA supplementation (FIG. 10A, FIG. 10B, FIG. 10C, FIG. 10D, FIG. 10E, FIG. 9C, FIG. 9D): BMDMs were mock-treated (media replacement only) or treated with 20 ng/mL of IL4±etomoxir (concentration indicated in figures)±CoA (concentration indicated in figures) for 48 hr. Etomoxir and CoA were given as co-treatments simultaneously with IL-4.

RNA Isolation and qPCR Analysis for BMDM

RNA was isolated with TRIzol, then cDNA was synthesized with high-capacity cDNA reverse transcription kit. KAPA SYBR FAST qPCR Master Mix kit and a LightCycler 480 were used for quantitative RT-PCR. Fold change related to the control group was calculated using 244CP method with 36b4 as the reference gene.

FACS Analysis of BMDM Polarization:

Prior to FACS analysis, BMDMs were detached using 350 µL of Accutase, followed by two washes with FACS buffer (PBS+1% (v/v) BSA+0.05% (w/v) sodium azide). Anti-mouse CD16/32 antibody was used at a dilution of 1:500, while all other antibodies were used at a dilution of 1:250. All flow cytometry data were captured using BD FACSVerse flow cytometer and analyzed using the FlowJo X 10.0.7r2 software. In all, 2×10$^4$ live events were acquired for each sample (gated on DAPIneg). For analysis, CD206+/CD71+ and CD206+/CD301+ populations were gated based on Fluorescence Minus One (FMO) controls.

Mass Spectrometry-Based Metabolomics Analysis

The experiments were performed as described in Xiao, G., Chan, L. N., Klemm, L., Braas, D., Chen, Z., Geng, H., Zhang, Q. C., Aghajanirefah, A., Cosgun, K. N., Sadras, T., et al. (2018) Cell-specific diversion of glucose carbon utilization reveals a unique vulnerability in B cell malignancies. Cell. 173, 470-484. Briefly, cells were seeded in 6-well dishes at 1×10$^6$ cells/well. Cells were treated with IL-4 with and without etomoxir co-treatments (3 µM or 200 µM) similarly to other experiments. To extract intracellular metabolites, cells were briefly rinsed with cold 150 mM ammonium acetate (pH 7.3), followed by addition of 1 ml cold 80% MeOH on dry ice. Cells were detached with cell scrapers and suspensions transferred into centrifuge tubes. After rigorous mixing, the suspension was pelleted by centrifugation (1.3×10$^4$ rpm, 4° C.). The supernatant was transferred into a glass vial, metabolites were dried down under vacuum, and resuspended in 50% (v/v) acetonitrile including heavy isotope-labeled amino acids as internal standards (Chen, W. W., Freinkman, E. and Sabatini, D. M. (2017) Rapid immunopurification of mitochondria for metabolite profiling and absolute quantification of matrix metabolites. Nat. Protoc. 12, 2215-2231).

For the mass spectrometry-based analysis of the sample, 5 µL were injected onto a Luna NH2 (150 mm×2 mm, Phenomenex) column. The samples were analyzed with an UltiMate 3000RSLC (Thermo Scientific) coupled to a Q Exactive mass spectrometer (Thermo Scientific). The Q Exactive was run with polarity switching (+3.50 kV/−3.50 kV) in full scan mode with an m/z range of 65-975. Separation was achieved using A) 5 mM NH4AcO (pH 9.9) and B) ACN. The gradient started with 15% A) going to 90% A) over 18 min, followed by an isocratic step for 9 min and reversal to the initial 15% A) for 7 min. Metabolites were quantified with El Maven (v0.2.4) using accurate mass measurements (≤3 ppm) and retention times of pure standards. Data analysis was performed using the statistical language R. For the PCA and clustering analyses, only metabolites with an ANOVA p-value≤0.05 were incorporated. For visualization using heatmaps, metabolites were scaled across samples but not across metabolites. To assess what metabolites contributed the most to a given metabolic phenotype, we calculated the correlation between the loading vector for a given metabolite and the score vector of a given sample for PCs 1 and 2.

Quantification and Statistical Analysis

All statistical parameters, including the number of replicates (n), can be found in the figure legends. Statistical analyses were performed using Graph Pad Prism 6 software. Data are presented as the mean±SEM. Individual pairwise comparisons were performed using two-tailed Student's t-test. For experiments involving two or more factors, data were analyzed by one-way, repeated measures ANOVA followed by Dunnett post-hoc multiple comparisons tests. Data were assumed to follow a normal distribution (no tests were performed). Values denoted as follows were considered significant: *, $p<0.05$; , $p<0.01$; *, $p<0.001$; ****, $p<0.0001$.

Figure 1B:
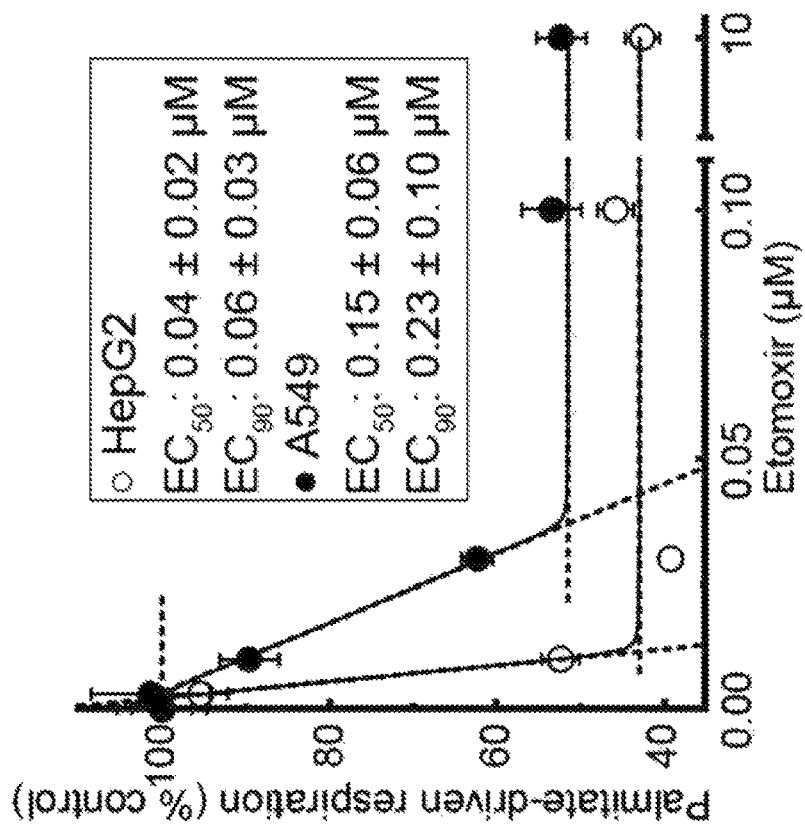
FIG. 1A, FIG. 1B, FIG. 1C, FIG. 1D, FIG. 1E, FIG. 1F, FIG. 1G and FIG. 1H show that etomoxir concentrations that specifically inhibit CPT-1 do not inhibit M(IL-4) polarization.
Figure 1A:
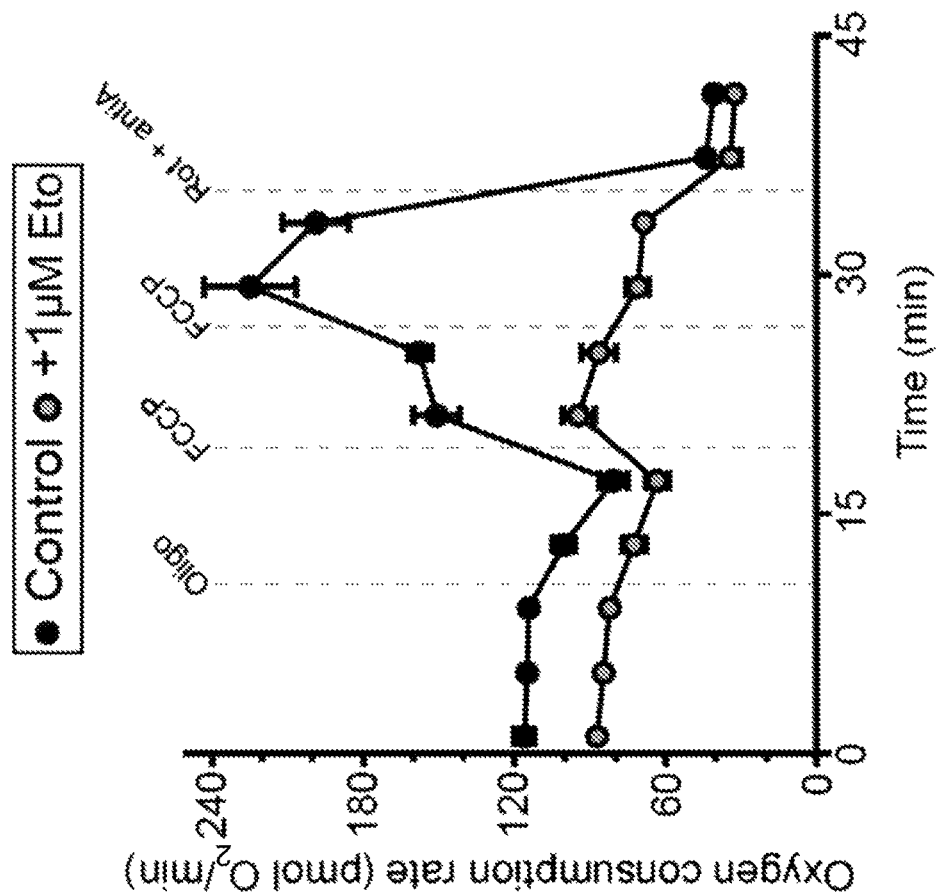
Figure 1D:
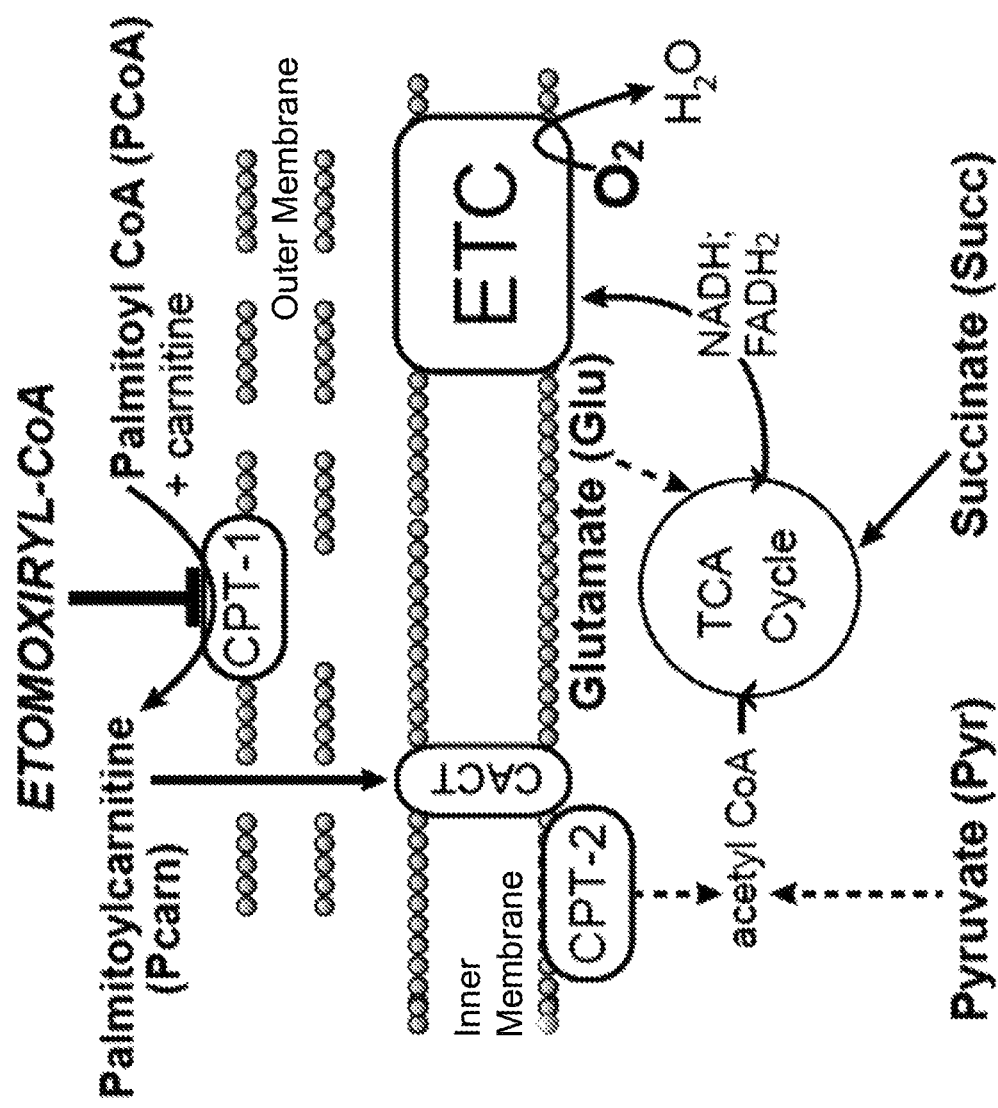
Figure 1C:
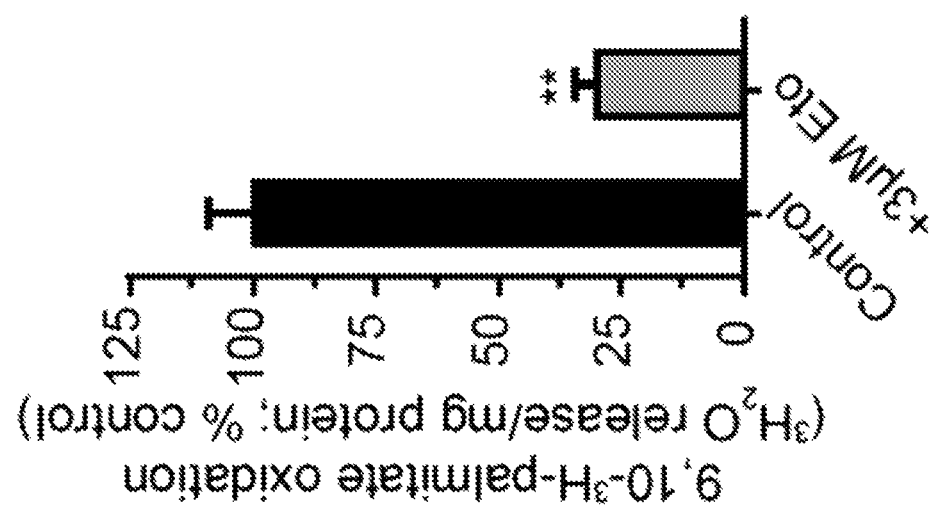

Example 1. Low Concentrations of Etomoxir Effectively Inhibit CPT-1 but do not Affect M(IL-4) Polarization Prior to localizing potential off-target effects of etomoxir, we first confirmed an appropriate on-target concentration at CPT-1 in a variety of cell types. We measured oxygen consumption rates in cultured cells offered albumin-buffered palmitate as a respiratory substrate. HepG2 cells could sustain robust rates of FCCP-stimulated respiration that were largely sensitive to 1 µM etomoxir (FIG. 1A). Under these conditions, concentration-response curves showed etomoxir had a sub-micromolar half-maximal inhibitory concentration (EC50) for uncoupler-stimulated respiration in both HepG2 and A549 cells (FIG. 1B). To corroborate this finding with an orthogonal measurement of LCFA oxidation in BMDMs, we observed that 3 µM etomoxir can effectively suppress 3H2O release from tritiated palmitate (FIG. 1C). The results confirm etomoxir is a potent, saturable inhibitor of LCFA oxidation in whole cells. Importantly, these data align with enzymology, cell-based assays, and tissue studies showing the inhibitor works with nanomolar or low micromolar efficacy depending upon the biological model.

Figure 1E:
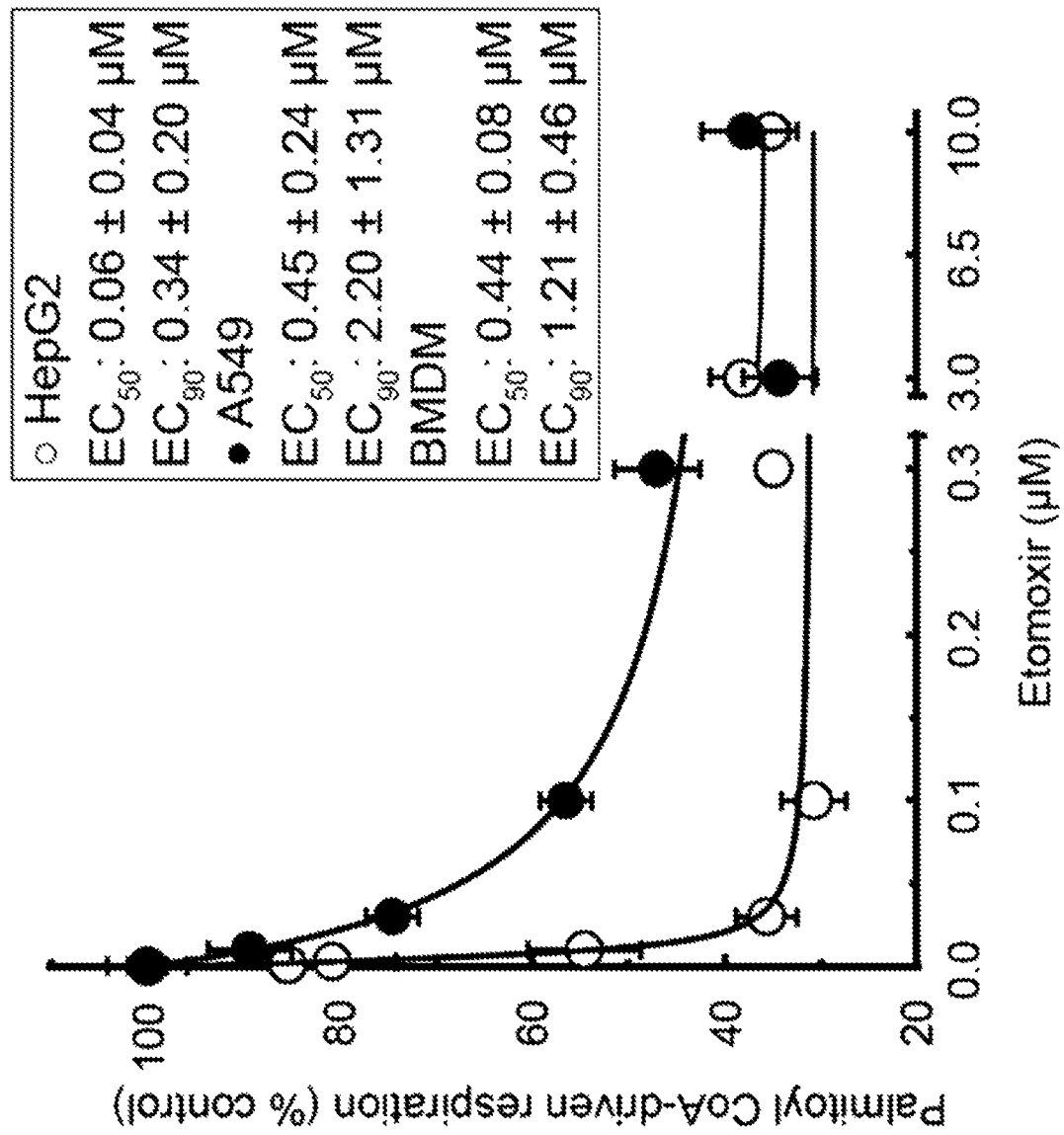

Although experiments in intact cells address the potency of etomoxir, they do not demonstrate specificity. We therefore used substrate-specific respirometry in permeabilized cells to determine a concentration of etomoxir that produced a saturable, specific inhibitory effect at CPT-1. Permeabilized cells were offered palmitoyl-CoA with carnitine to directly interrogate respiration mediated by CPT-1 (FIG. 1D). The CoA thioester of etomoxir is the active, irreversible inhibitor of CPT-1, so cells were pretreated with etomoxir to allow formation of etomoxiryl-CoA prior to plasma membrane permeabilization. In permeabilized HepG2s, A549s, and BMDMs, etomoxir inhibited FCCP-stimulated, palmitoyl CoA-driven respiration with nanomolar EC50 values, and had a saturable effect at less than 3 µM (FIG. 1E).

Figure 1F:
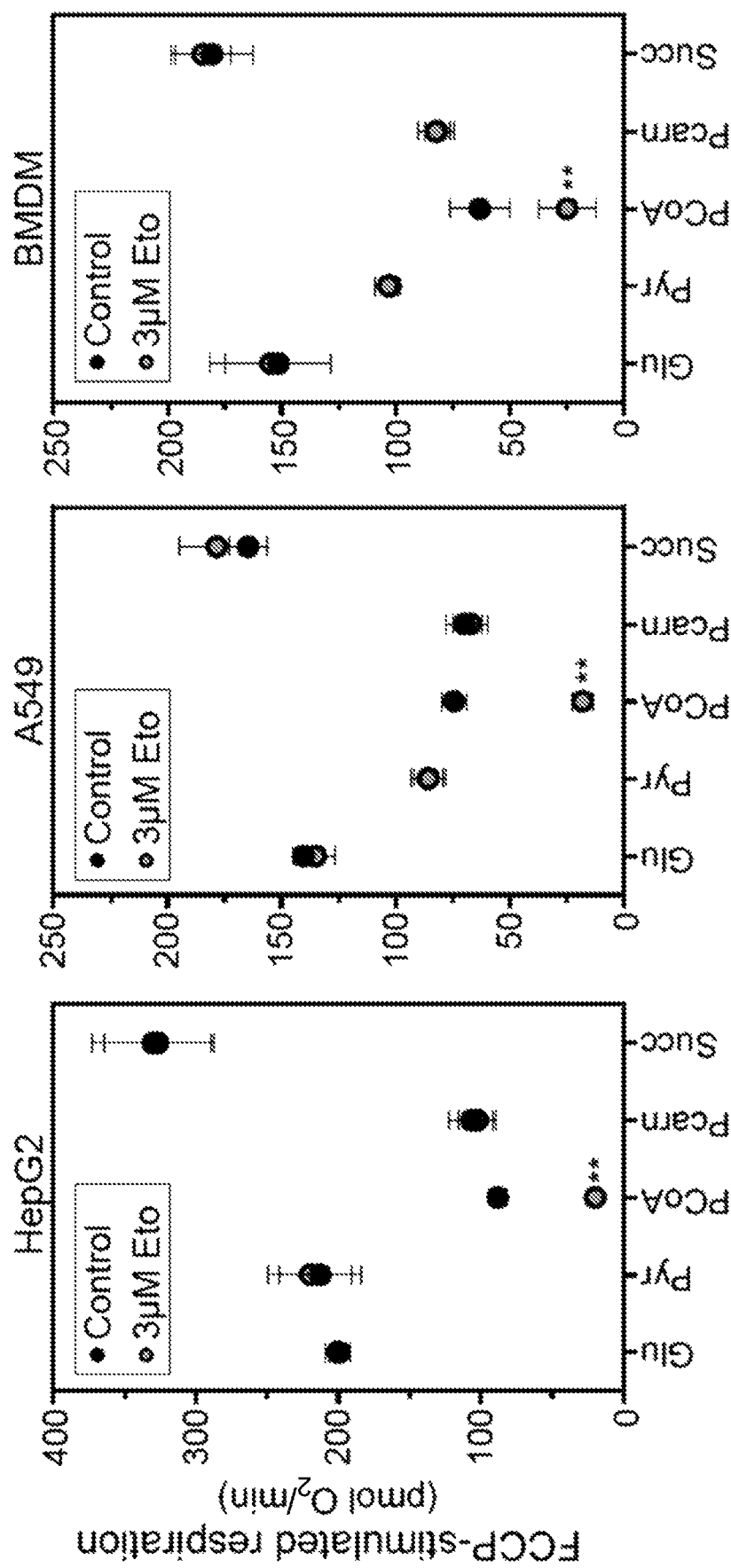
Figure 1G:
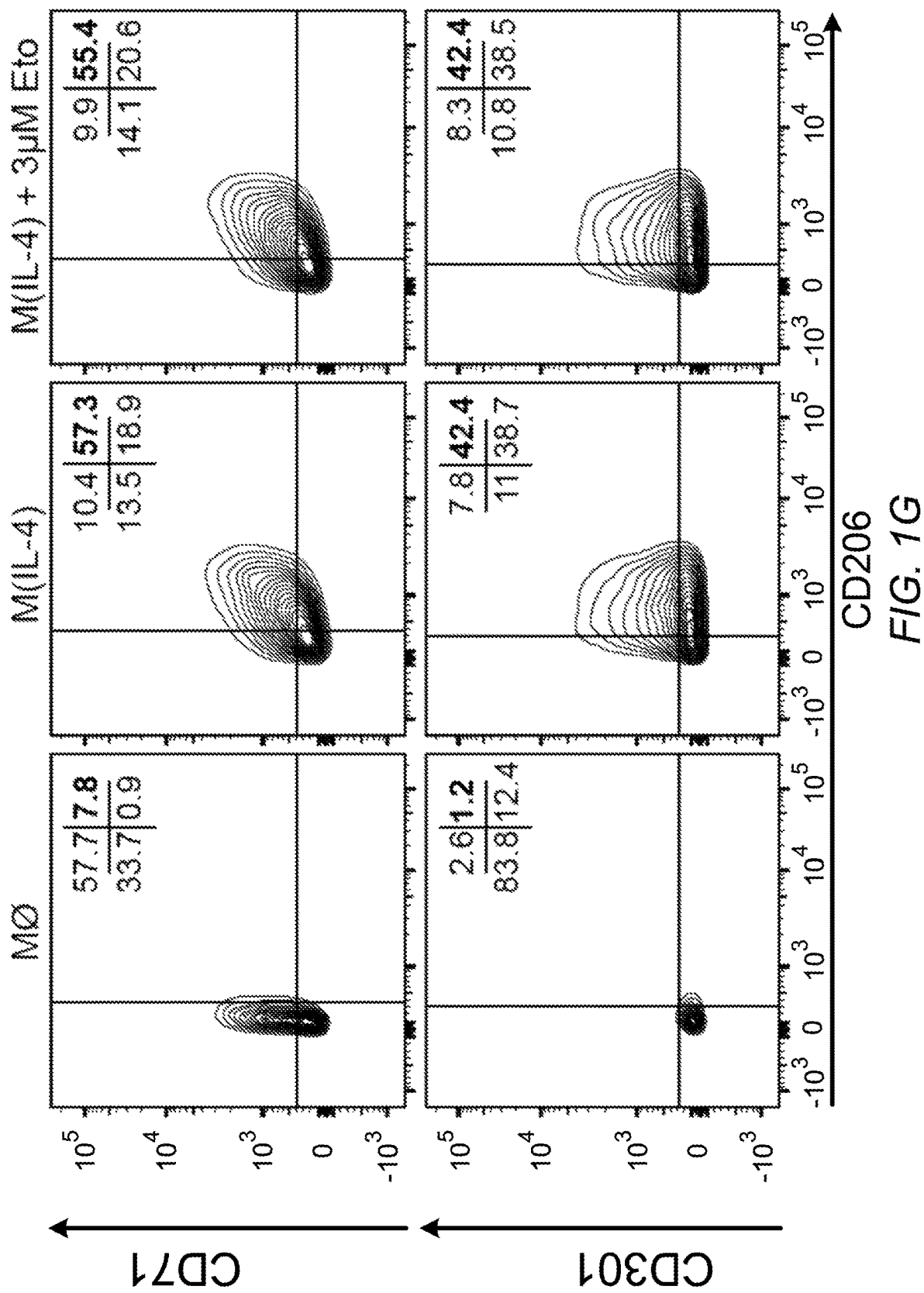

To verify this was a specific effect at CPT-1 rather than another downstream enzyme, permeabilized cells were offered other respiratory substrates in the presence of 3 µM etomoxir. Etomoxir had a significant effect on palmitoyl CoA oxidation, but no effect on respiration driven by substrates which do not require CPT-1: glutamate/malate, pyruvate/malate, palmitoylcarnitine/malate, and succinate/rotenone (FIG. 1F). Residual respiratory rates in the presence of saturating etomoxir may be driven by endogenous substrates and/or exogenously added malate. Nonetheless, these substrate specificity experiments demonstrate that 3 µM etomoxir is a specific, saturable inhibitor of CPT-1 in BMDMs.

Figure 1H:
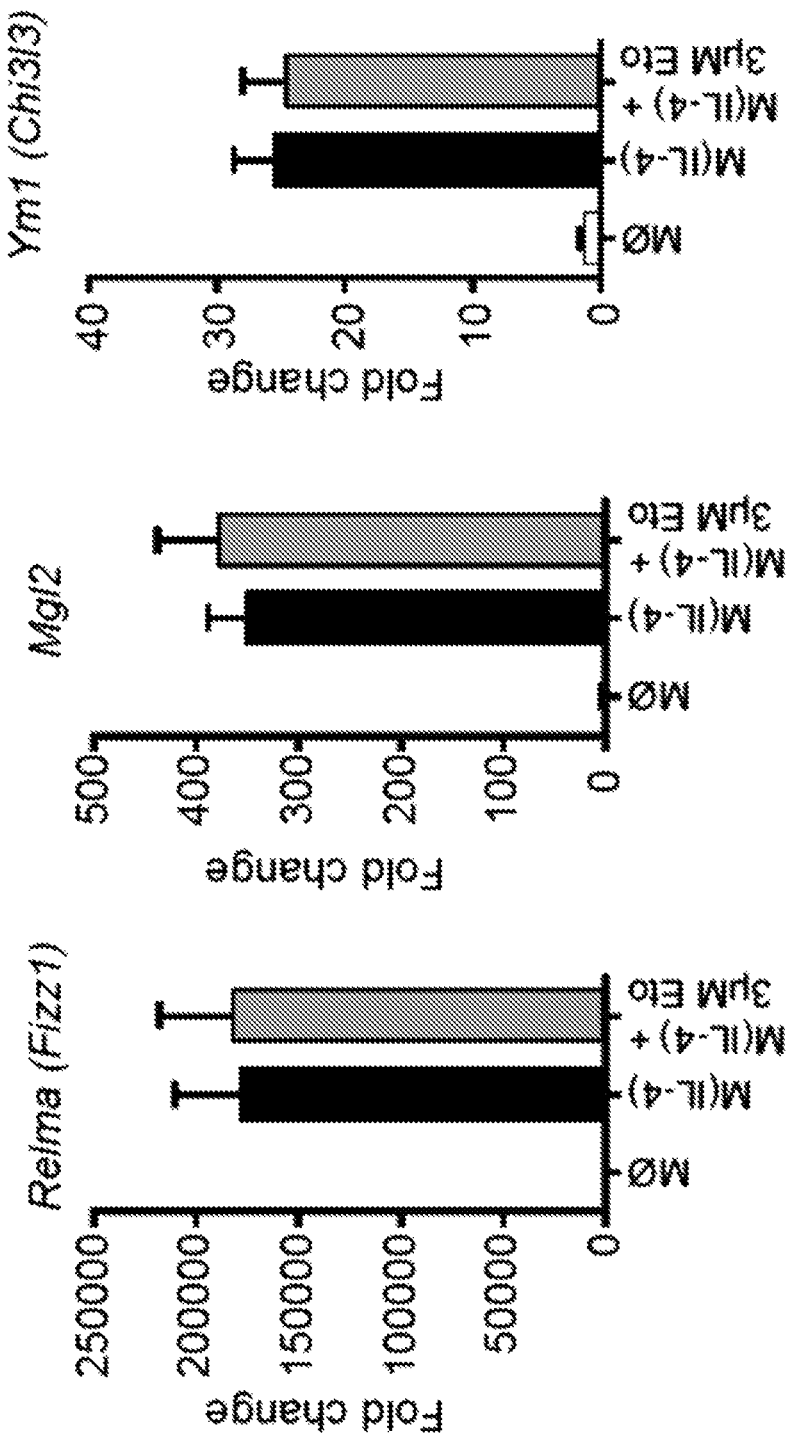
Figure 1H:
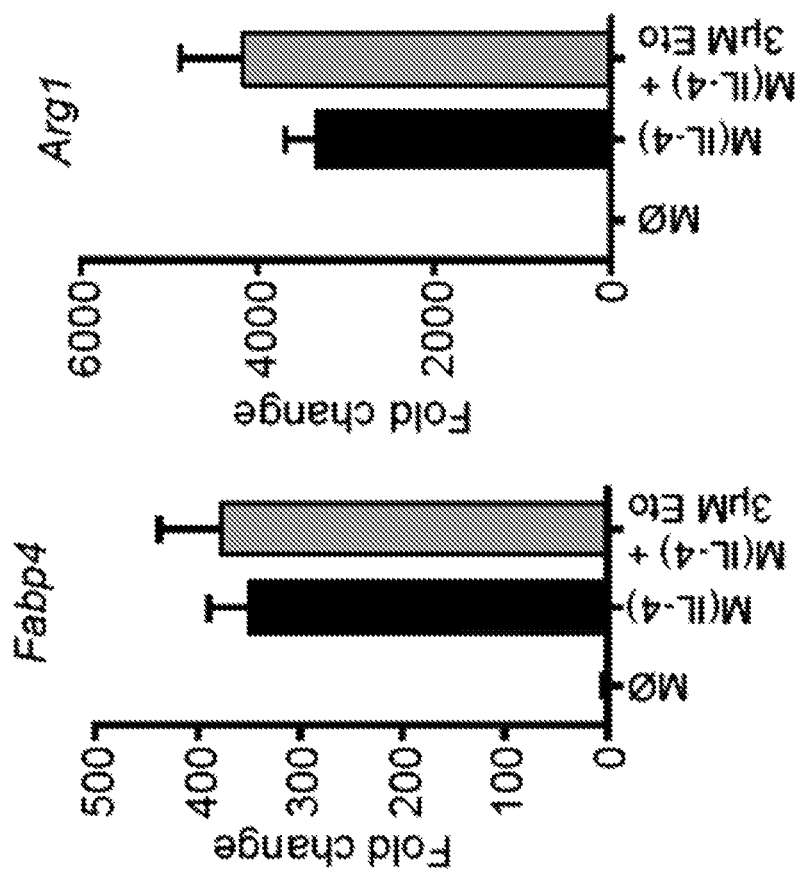

Having established the efficacy of low concentrations of etomoxir in blocking CPT-1, we then examined whether 3 µM etomoxir impacts IL-4-mediated polarization of macrophages. FACS analysis revealed that 3 µM etomoxir had no effect on the expression levels of IL-4-induced CD206, CD71, or CD301 (FIG. 1G), markers of alternative macrophage activation. Moreover, no change was observed in the gene expression of Relma, Mgl2, Ym1, Fabp4, and Arg1, key markers of M(IL-4) polarization (FIG. 1H). Taken together, the data indicate pharmacologic inhibition of CPT-1 by etomoxir inhibits LCFA oxidation but does not block IL-4-induced macrophage polarization. They also support similar observations showing the IL-4 response is unaffected by etomoxir concentrations ranging from 10 µM to 100 µM.

Detailed description of FIG. 1. Etomoxir concentrations that specifically inhibit CPT-1 do not inhibit M(IL-4) polarization. (FIG. 1A) Respirometry trace with intact HepG2 cells±1 µM etomoxir (Eto) offered albumin-buffered palmitate as substrate. (n=6 technical replicates). (FIG. 1B) Concentration-response curve of FCCP-stimulated respiration in intact HepG2 and A549 cells [as in (FIG. 1A)] in response to increasing concentrations of etomoxir. (n=6 technical replicates). Inset: Aggregate values for EC50 (concentration required for 50% inhibition) and EC90 (90% inhibition) from n≥4 independent biological replicates. (FIG. 1C) Fatty acid oxidation as measured by 3H2O release from 9,10-3H-palmitate±3 µM etomoxir (Eto). (n=4 independent biological replicates). (FIG. 1D) Schematic depicting respiratory substrates used for permeabilized cell respirometry. CPT, carnitine palmitoyl transferase; CACT, carnitine acyl carnitine transferase; ETC, electron transport chain. (FIG. 1E) Sample concentration-response curve of FCCP-stimulated oxygen consumption in permeabilized HepG2 and A549 cells (BMDMs omitted for clarity) in response to increasing concentrations of etomoxir (n=6 technical replicates). Cells were offered palmitoyl CoA with carnitine and malate as substrates. Inset: Aggregate values for EC50 and EC90 in all cell types tested. (n≥4 independent biological replicates). (FIG. 1F) Effect of etomoxir on various respiratory substrates in permeabilized cells. Glu, glutamate/malate; Pyr, pyruvate/malate; PCoA, palmitoyl CoA/carnitine/malate; Pcarn, palmitoylcarnitine/malate; Succ, succinate/rotenone. (n=3 independent biological replicates). (FIG. 1G) Flow cytometric analysis of the IL-4-associated cell surface markers CD206, CD301, and CD71 in BMDMs 24 hr after the indicated treatment. Cells were co-treated with IL-4 (20 ng/mL) and etomoxir (3 µM). Numbers in the top-right quadrant indicate cells positive for both markers measured. The data shown are from one experiment and representative of a total of six independent biological replicates. (H) qPCR analysis of the IL-4-associated genes Relma, Mgl2, Ym1, Fabp4, and Arg1 after 24 hr of IL-4±3 µM etomoxir co-treatment. (n=4 independent biological replicates). The following primers were used for the analysis:

Relma(Fizz1) primer:
Fwd:
TCGTGGAGAATAAGGTCAAGG, (SEQ ID NO: 1)

Rev:
AGGAGGCCCATCTGTTCATA; (SEQ ID NO: 2)

Mgl2 primer:
Fwd:
AGGCACCCTAAGAGCCATTT, (SEQ ID NO: 3)

Rev:
CCCTCTTCTCCAGTGTGCTC; (SEQ ID NO: 4)

Ym1(Chi3l3) primer:
Fwd:
TAAGACTGGAATTGGTGCCC, (SEQ ID NO: 5)

Rev:
TAAGACTGGAATTGGTGCCC; (SEQ ID NO: 6)

Fabp4 primer:
Fwd:
GGATGGAAAGTCGACCACAA, (SEQ ID NO: 7)

Rev:
TGGAAGTCACGCCTTTCATA; (SEQ ID NO: 8)

36b4 primer:
Fwd:
CTGTGCCAGCTCAGAACACTG, (SEQ ID NO: 9)

Rev:
TGATCAGCCCGAAGGAGAAG. (SEQ ID NO: 10)

Figure 2A:
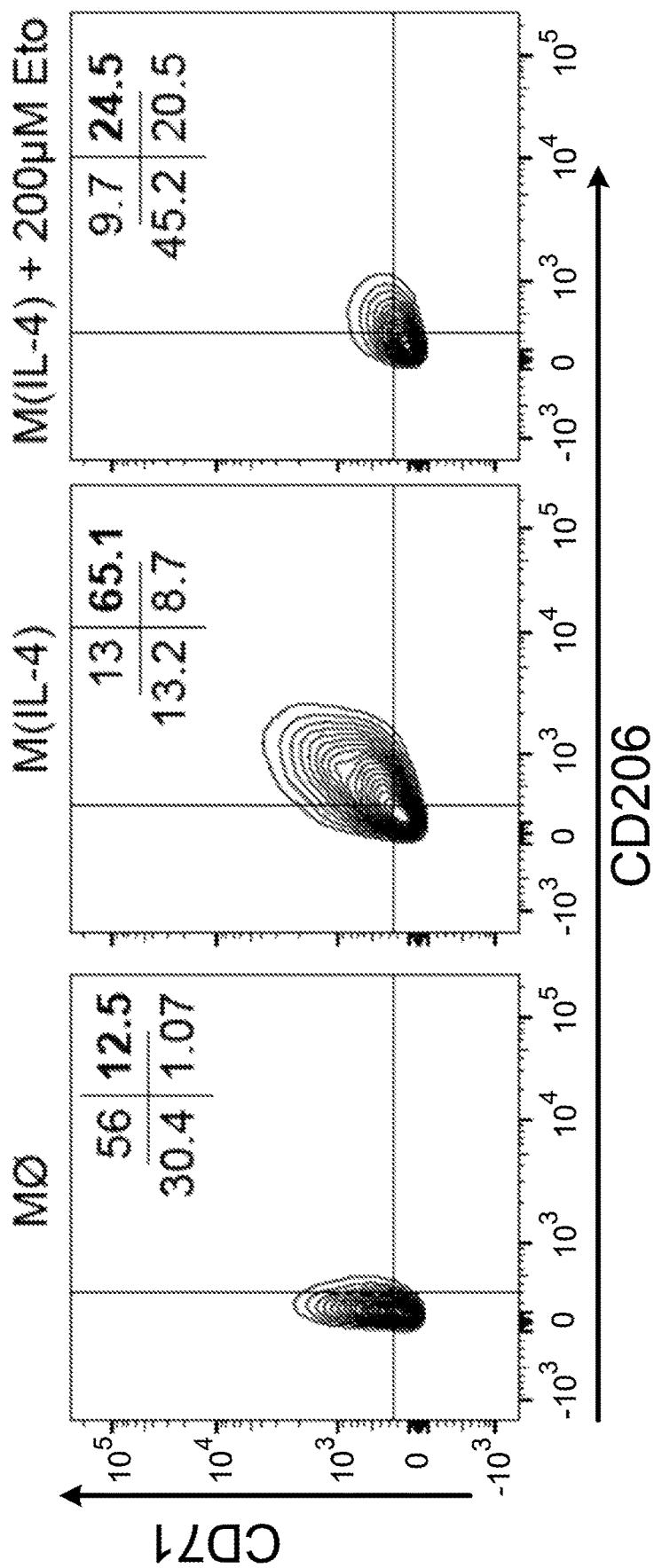
FIG. 2A, FIG. 2B, FIG. 2C and FIG. 2D show that high concentrations of etomoxir block M(IL-4) polarization independently of CPT-1 activity.
Figure 2B:
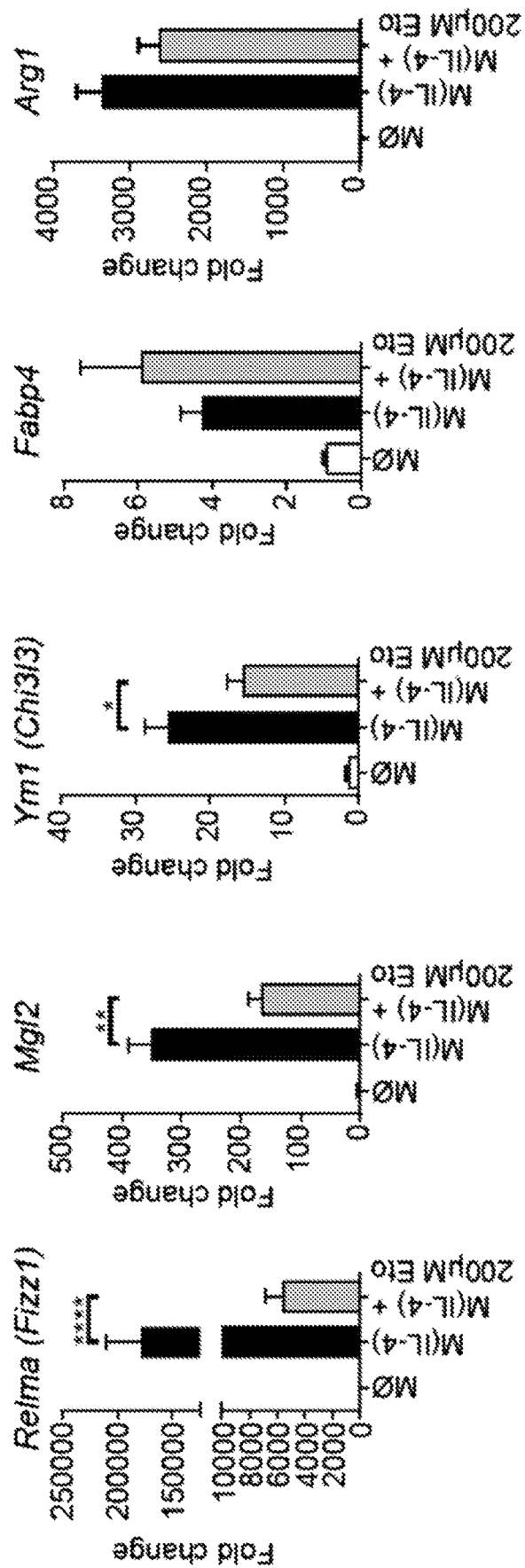

Example 2. High Concentrations of Etomoxir Inhibit M(IL-4) Polarization Independently of CPT-1 Activity Having established that concentrations of etomoxir that maximally inhibit CPT-1 do not block IL-4-mediated responses in BMDMs, we then hypothesized that promiscuous effects of the drug were responsible for its well-established inhibition of alternative macrophage activation. As previously reported, 200 µM etomoxir strongly reduced the population of CD206+/CD71+ cells in response to IL-4-driven polarization (FIG. 2A). However, significant changes in macrophage polarization were only observed at concentrations >100 µM (FIG. 3A), orders of magnitude greater than the EC50 for CPT-1 inhibition and suggestive of a mechanism discrete from LCFA oxidation. 200 µM etomoxir also had little effect on the population of CD301+ cells (FIG. 3B), suggesting that etomoxir affects only a subset of the IL-4 responses. Additional evidence supporting a mosaic-like effect of etomoxir on M(IL-4) polarization is given by gene expression patterns: 200 µM etomoxir blocked the induction of Relma, Mgl2, and Ym1 expression, but no change was observed for Fabp4 and Arg1 (FIG. 2B). Arginase activity was also unaffected by high etomoxir (FIG. 3C), reinforcing previous findings.

Figure 2C:
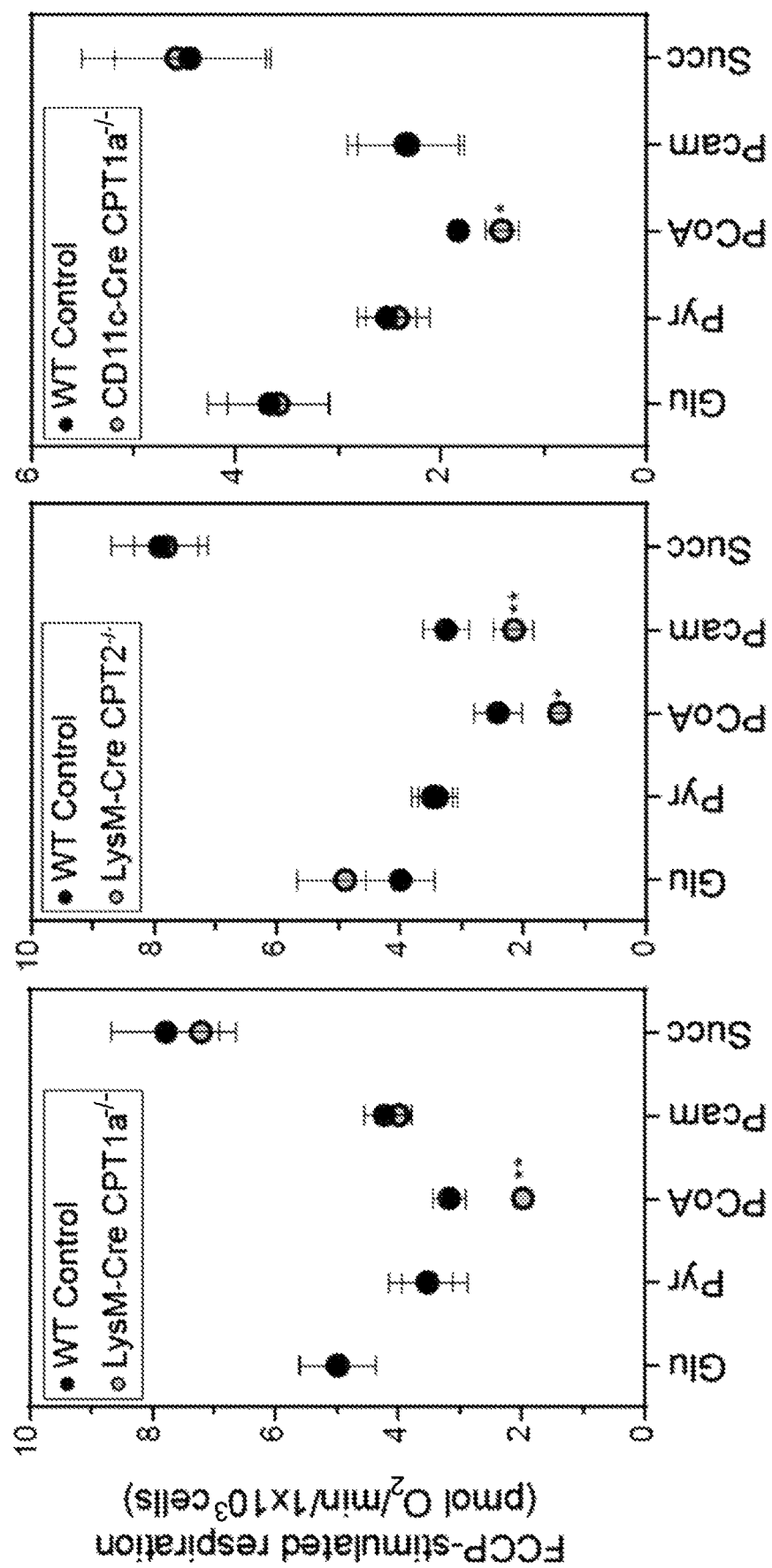
Figure 3B:
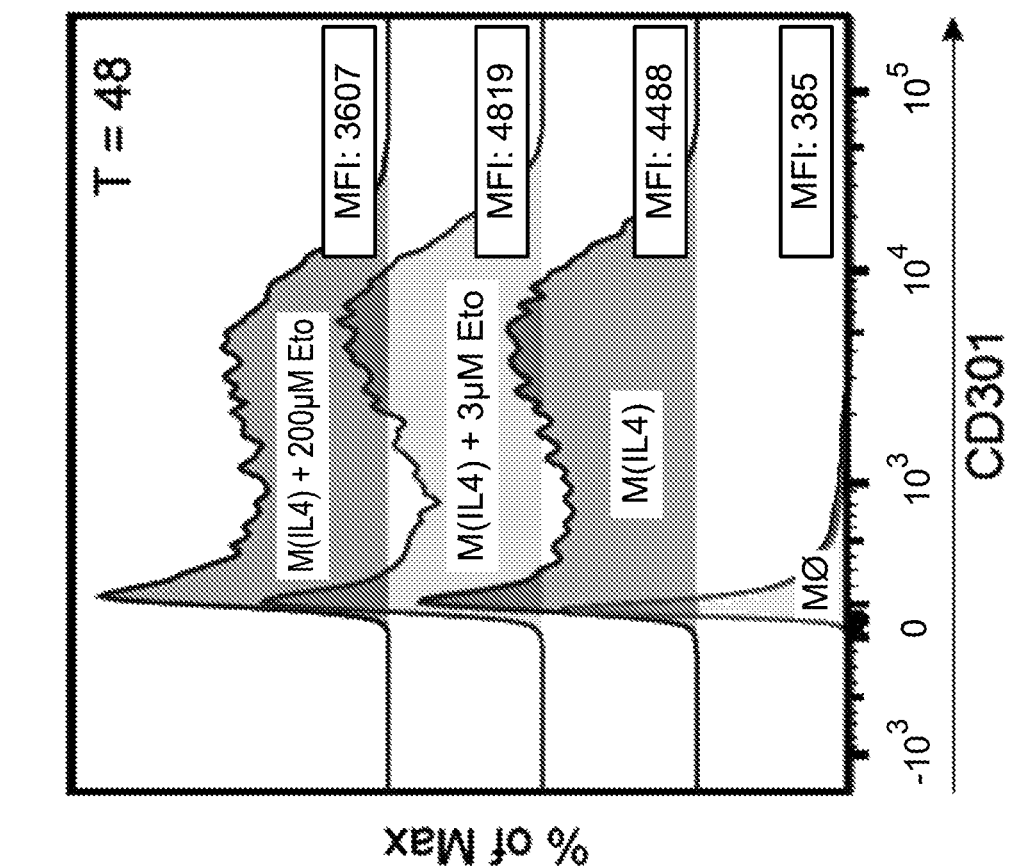
Figure 3A:
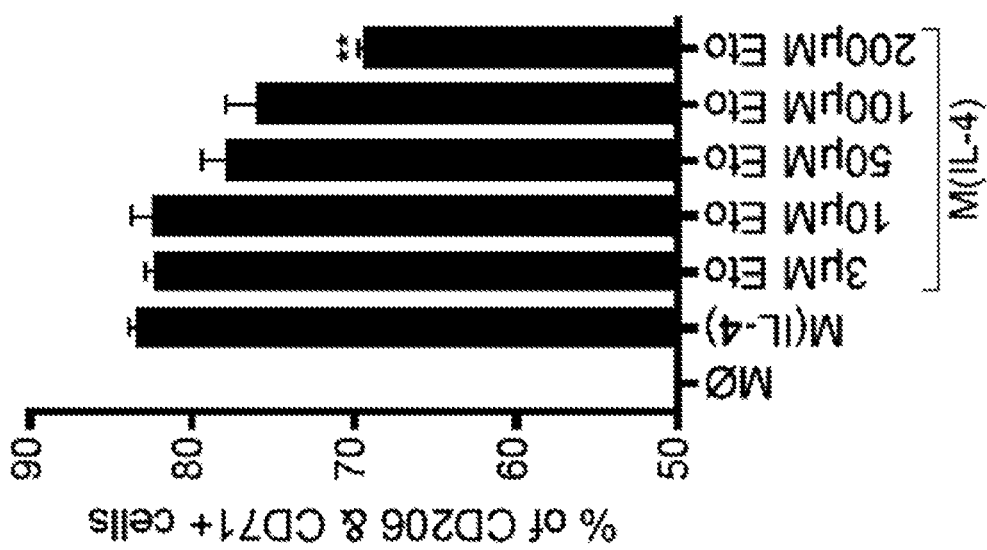
Figure 3D:
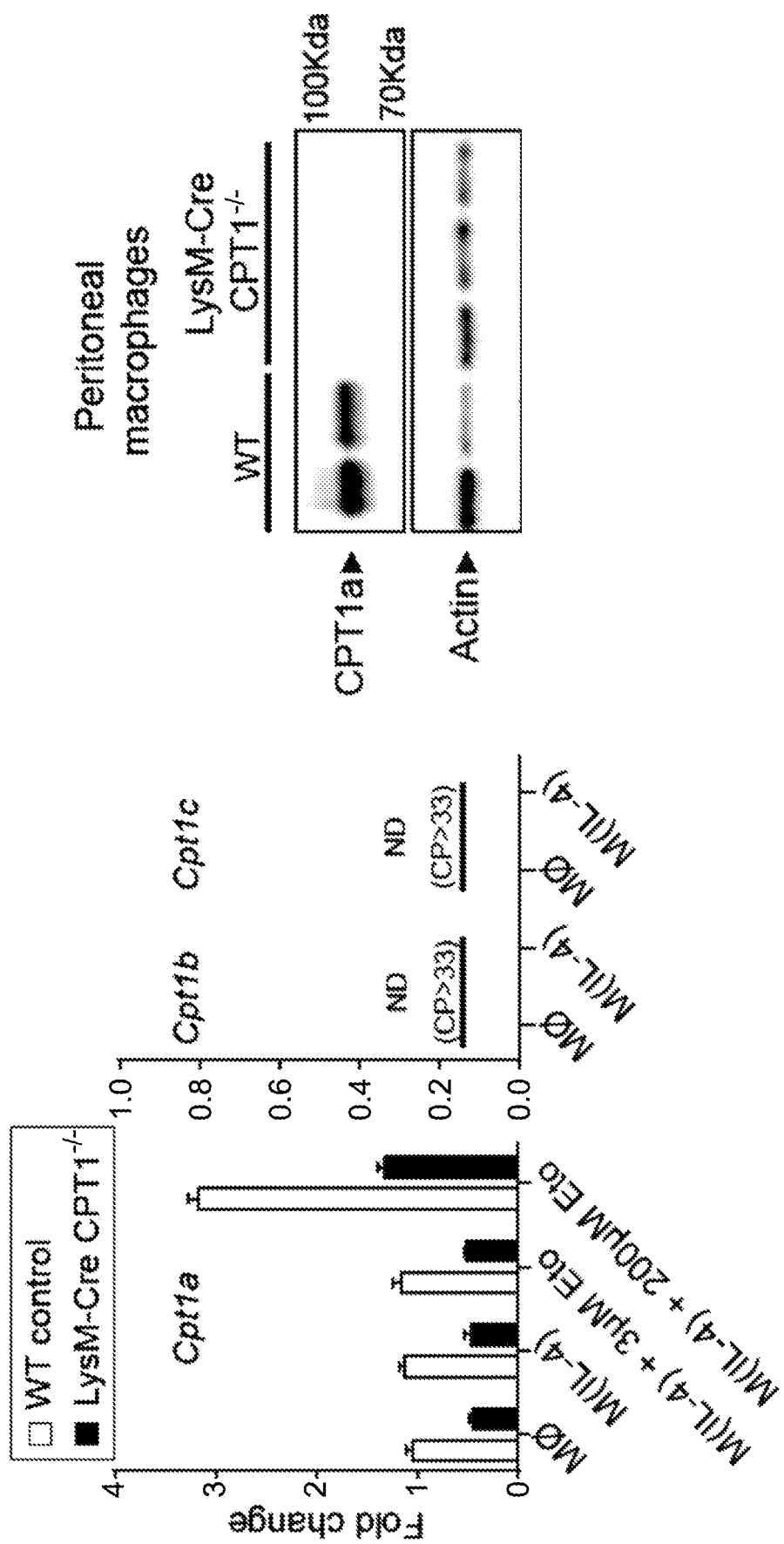
Figure 3E:
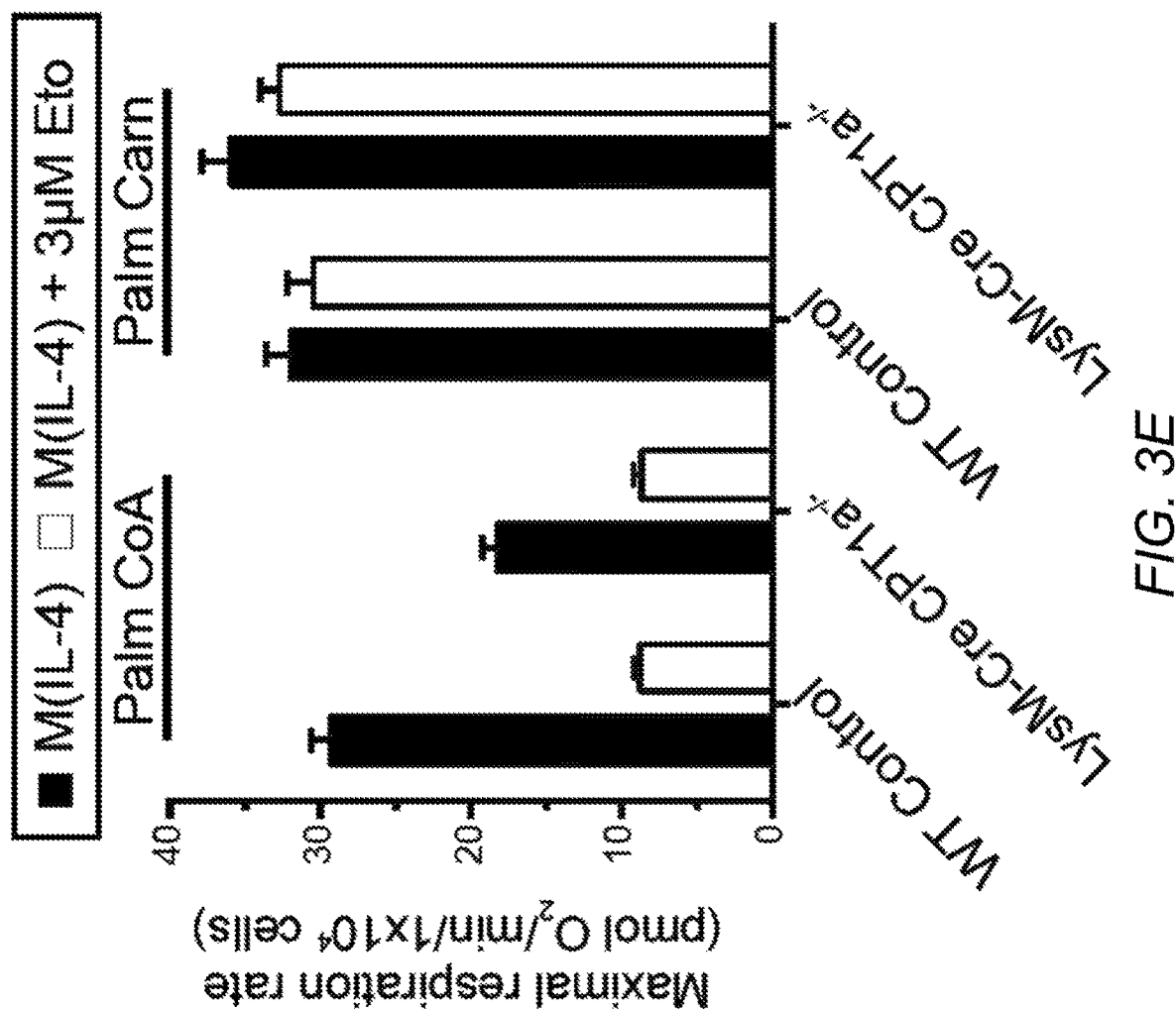
Figure 3F:
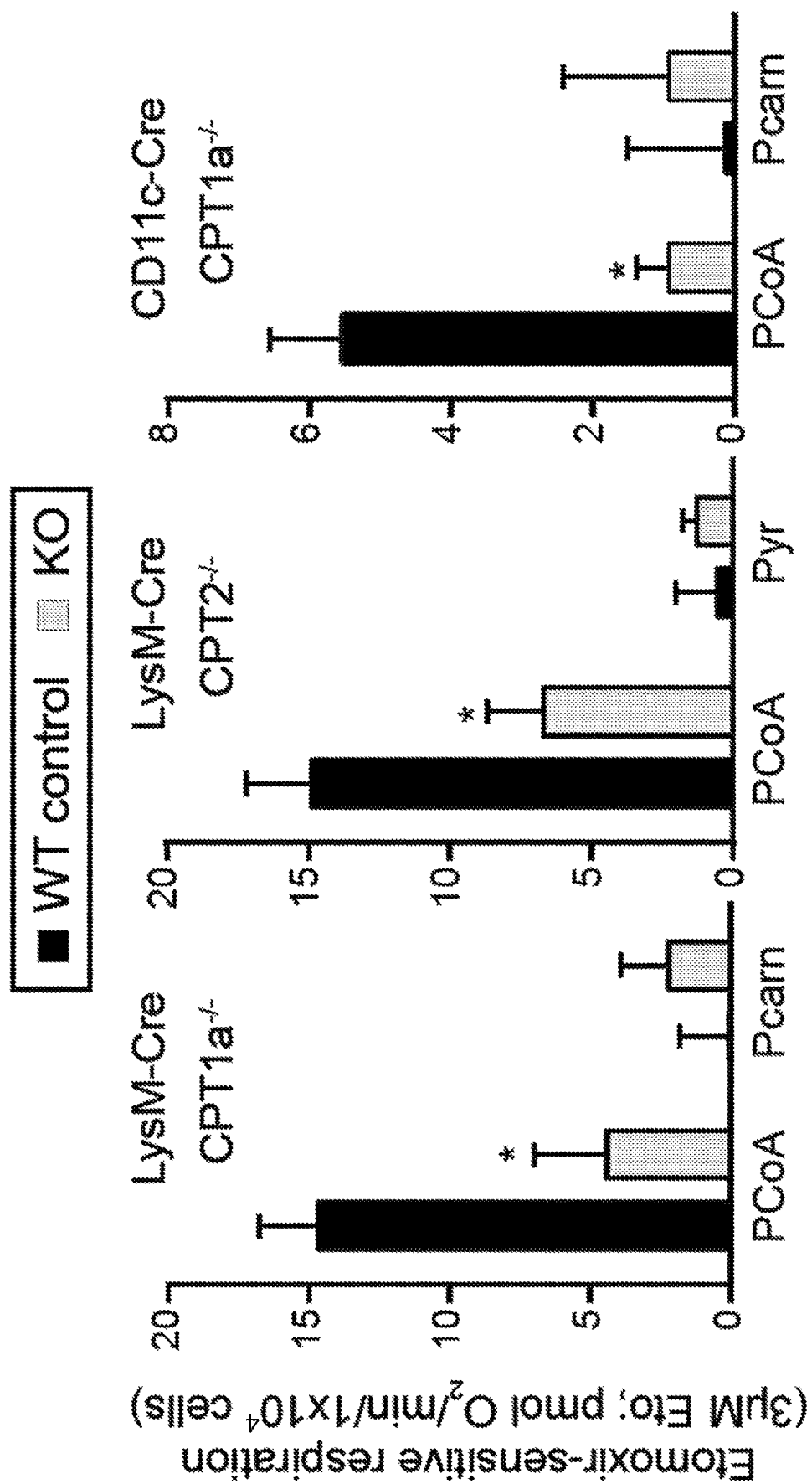
Figure 3G:
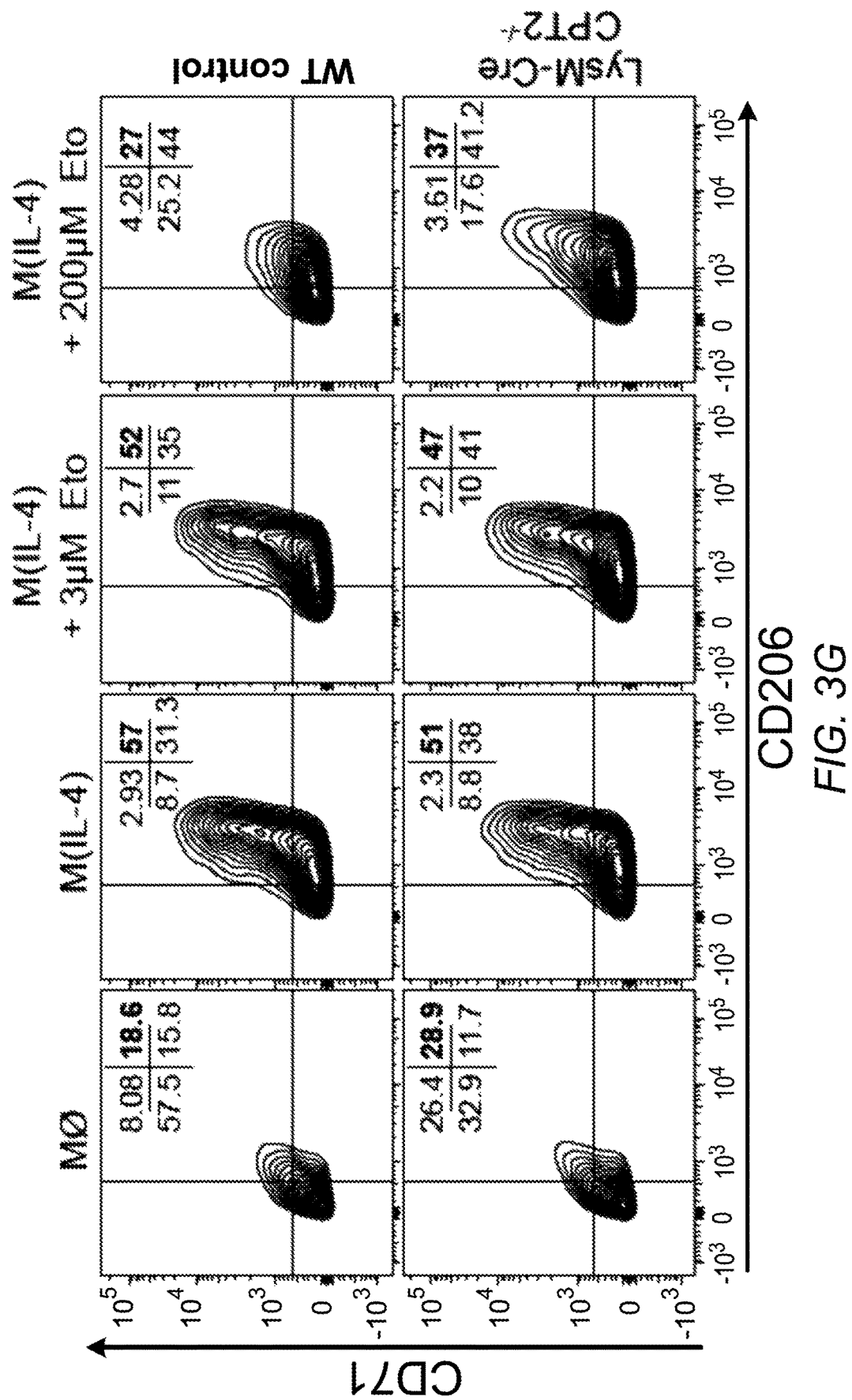

To further confirm that the effect of excess etomoxir on M(IL-4) polarization was independent of LCFA oxidation, we characterized macrophage polarization in BMDMs with genetic disruption of CPT-1a or CPT-2. BMDMs with a myeloid-specific deletion of Cpt1a were generated by breeding LoxP-Cpt1a mice with either LysM-Cre or CD11c-Cre mice, and a similar strategy was used for generation of Cpt2−/− mice. In addition to reduced expression at the transcript and protein level (FIG. 3D), functional deficiency of CPT1a was characterized by substrate-specific respirometry in permeabilized BMDMs (FIG. 2C). Analogous to the specificity of 3 µM etomoxir (FIG. 1F), decreased rates of palmitoyl CoA-driven respiration were observed in the two conditional Cpt1a−/− strains while respiration on other mitochondrial substrates was unchanged relative to controls (FIG. 2C). Moreover, since CPT-2 is required for the oxidation of both palmitoyl CoA and palmitoylcarnitine (FIG. 1C), BMDMs from Cpt2−/− mice demonstrated compromised rates when oxygen consumption was driven by these substrates but not others (FIG. 2C), aligning with radiometric measurements of LCFA oxidation in these cells. Sensitivity of respiration to 3 µM etomoxir, a concentration shown to be specific to CPT-1 (FIG. 1), was largely absent in all three conditional CPT KO cells, further confirming a specific reduction in LCFA oxidation (FIG. 3E, FIG. 3F).

Figure 2D:
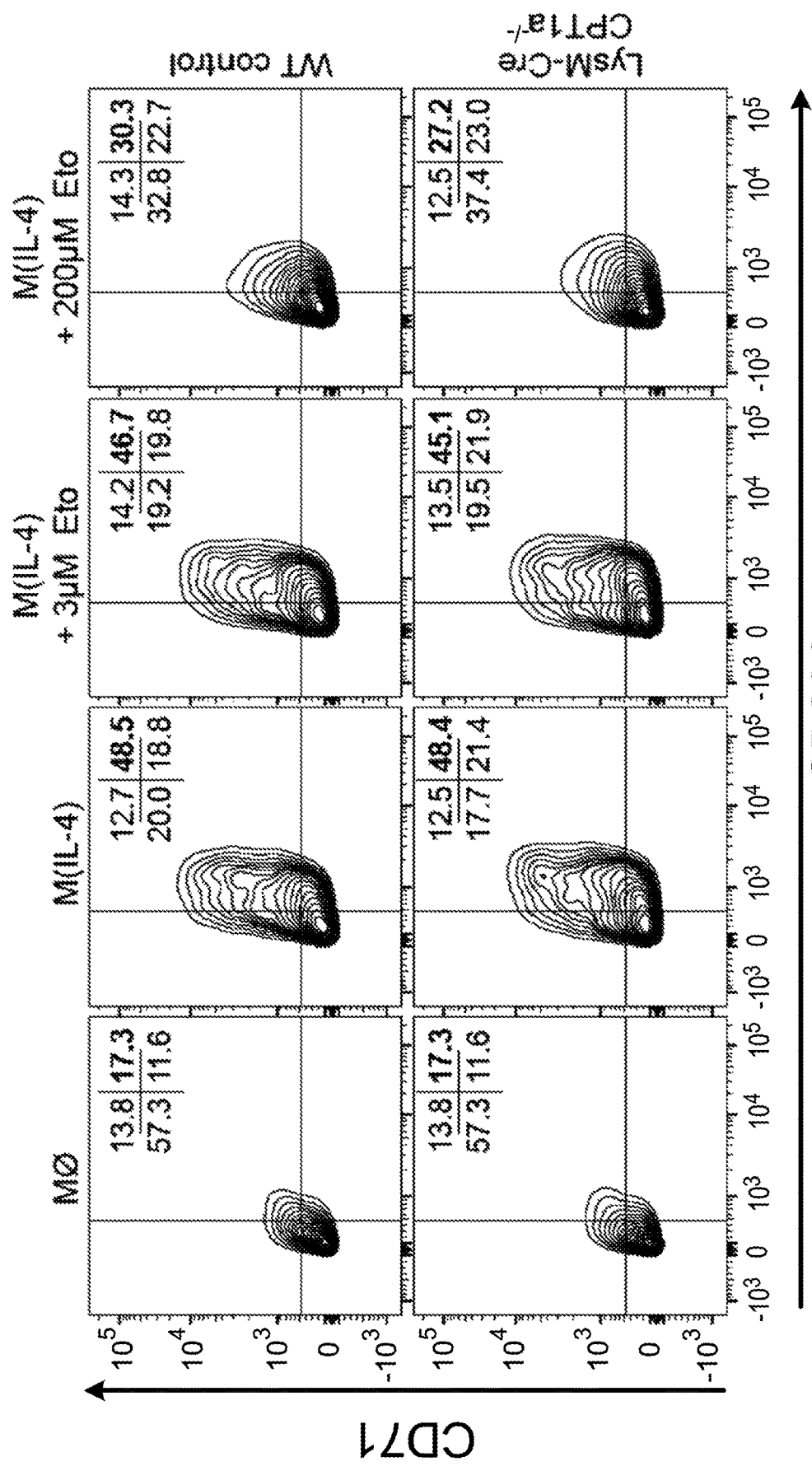
Figure 3H:
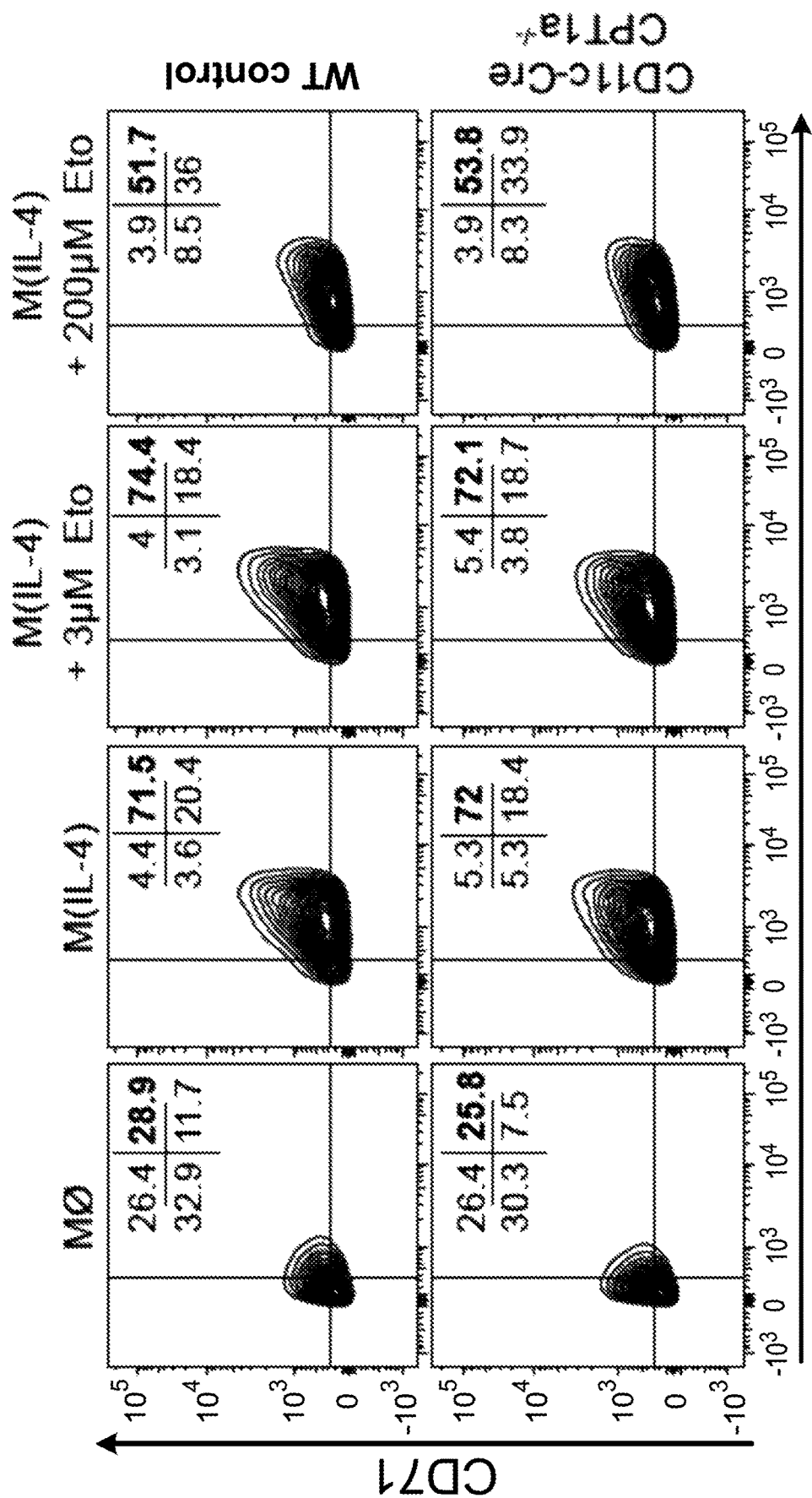
Figure 3I:
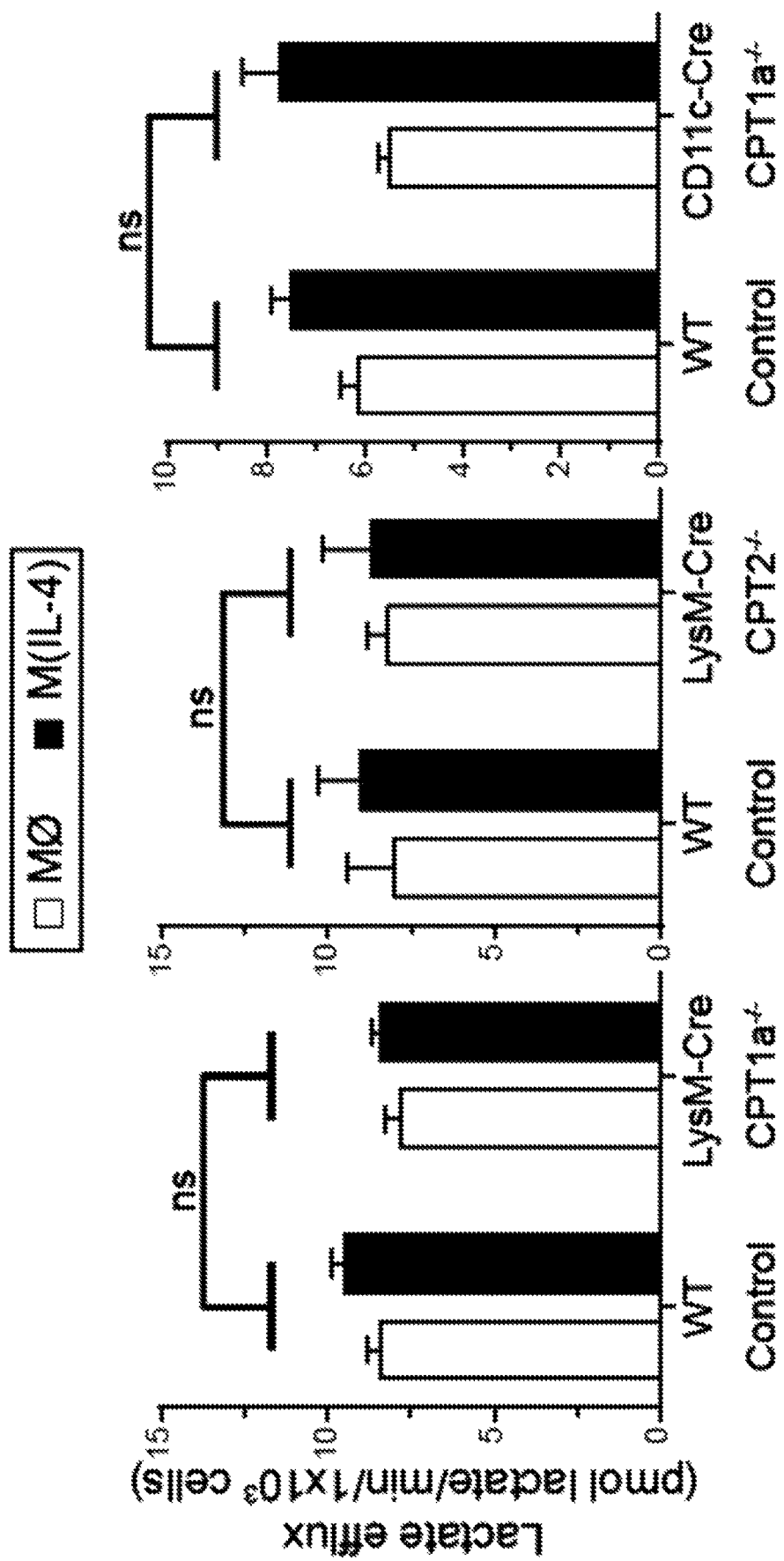

Similar to pharmacologic inhibition of CPT-1 using 3 µM etomoxir, genetic disruption of LCFA oxidation did not affect the response to IL-4. The population of CD206+/CD71+ in LysM-Cre Cpt1a−/− macrophages was unchanged upon M(IL-4) polarization (FIG. 2D). Moreover, the lack of an effect from 3 µM etomoxir but a robust block of CD206+/CD71+ expression from 200 µM was observed in both WT and Cpt1a−/− macrophages. A similar result was observed with the Cpt2−/− (FIG. 3G) and the CD11c-Cre Cpt1a−/− BMDMs (FIG. 3H). IL-4-stimulated lactate efflux was also unchanged despite genetic disruption of LCFA oxidation in all three cell types (FIG. 3I). In summary, these data reinforce the concept that LCFA oxidation is dispensable for alternative macrophage activation, and show the effects of excess etomoxir on M(IL-4) polarization are independent of CPT activity.

Detailed description of FIG. 2. High concentrations of etomoxir block M(IL-4) polarization independently of CPT-1 activity. (FIG. 2A) Flow cytometric analysis of CD206 and CD71 on macrophages treated with IL-4±200 µM etomoxir co-treatment after 24 hr. The data shown are from one experiment representative of a total of six independent biological replicates. (FIG. 2B) qPCR analysis of Relma, Mgl2, Ym1, Fabp4, and Arg1 in BMDM with IL-4±200 µM etomoxir co-treatment after 24 hr. (n=6 independent biological replicates). (FIG. 2C) Effect of various respiratory substrates in permeabilized WT, Cpt1−/−, and Cpt2−/− BMDMs. Glu, glutamate/malate; Pyr, pyruvate/malate; PCoA, palmitoyl CoA/carnitine/malate; Pcarn, palmitoylcarnitine/malate; Succ, succinate/rotenone. (n=4 independent biological replicates). (FIG. 2D) Flow cytometric analysis for the CD206+/CD71+ population in WT and Cpt1a−/− BMDMs differentiated with IL-4±3 µM or 200 µM etomoxir. The data shown are from one experiment representative of a total of four independent biological replicates. See also FIG. 3.

Detailed description of FIG. 3. (FIG. 3A) Aggregate flow cytometric data of IL-4-stimulated BMDMs showing CD206+/CD71+ treated with increasing concentrations of etomoxir for 24 hr. Values given are the geometric mean of fluorescence intensity. (n=6 independent biological replicates). (FIG. 3B) Flow cytometric analysis of CD301 expression in response to low (3 µM) or high (200 µM) etomoxir. The data shown are from one experiment representative of a total of six independent biological replicates. (FIG. 3C) Measurements of arginase activity in BMDMs with IL-4±200 µM etomoxir co-treatment for 24 hr. Data represents two independent biological replicates. (FIG. 3D) (Left) qPCR analysis on the expression of Cpt1a, Cpt1b, and Cpt1c in WT and Cpt1a−/− BMDMs co-treated with IL-4±etomoxir for 24 hr. Data represent two independent replicates. (Right) Quantification of CPT1a protein levels in WT or Cpt1−/− peritoneal macrophages. Each lane represents one individual mouse. (FIG. 3E) Representative data from an individual experiment measuring uncoupler-stimulated respiration±3 μM etomoxir in permeabilized WT or LysM-Cre Cpt1−/−. BMDMs were offered either palmitoyl CoA/malate/carnitine or palmitoylcarnitine/malate as substrates to measure respiration specifically mediated by CPT-1 activity. (n=5 technical replicates from a single biological replicate). BMDMs were treated with IL-4 for 24 hr. prior to measurements. (FIG. 3F) Etomoxir-sensitive respiration was defined as the difference in FCCP-simulated respiration rates±3 μM etomoxir. (n=4 independent biological replicates). Cpt2−/− BMDMs were offered pyruvate, rather than palmitoylcarnitine, because CPT-2 is required for oxidation of both palmitoyl CoA as well as palmitoylcarnitine. (FIG. 3G) Flow cytometric analysis for CD206+/CD71+ in WT and Cpt2−/− BMDMs differentiated with IL-4±3 μM or 200 μM etomoxir. The data shown are from one experiment representative of a total of three independent biological replicates. (FIG. 3H) Flow cytometric analysis for the CD206+/CD71+ population in WT and Cpt1a−/− BMDMs differentiated with IL-4±3 μM or 200 μM etomoxir. The data shown are from one experiment representative of a total of three independent biological replicates. (FIG. 3I) Lactate effluxed to the experimental medium by WT, Cpt1−/−, and Cpt2−/− BMDMs in response to 24 hr treatment with IL-4. Cells were offered 8 mM glucose, 2 mM glutamine, and 2 mM pyruvate. (n=3 independent biological replicates)

Example 3. High Concentrations of Etomoxir Inhibit the Adenine Nucleotide Translocase Having shown LCFA oxidation does not control alternative macrophage activation, we then sought to determine the off-target effect by which etomoxir was blocking M(IL-4) polarization. A growing body of literature has linked M(IL-4) polarization with genetic programs supporting mitochondrial biogenesis and aerobic glucose oxidation. Thus, we hypothesized that the off-target effect(s) of etomoxir on immune cell phenotypes could be via perturbed mitochondrial metabolism. Indeed, the extent of respiratory inhibition by 200 μM etomoxir was similar in WT and Cpt1a−/− or Cpt2−/− BMDMs (FIG. 4A). The observation suggests the reductions in respiration are attributable to effects on energy metabolism independent of LCFA oxidation.

Figure 5A:
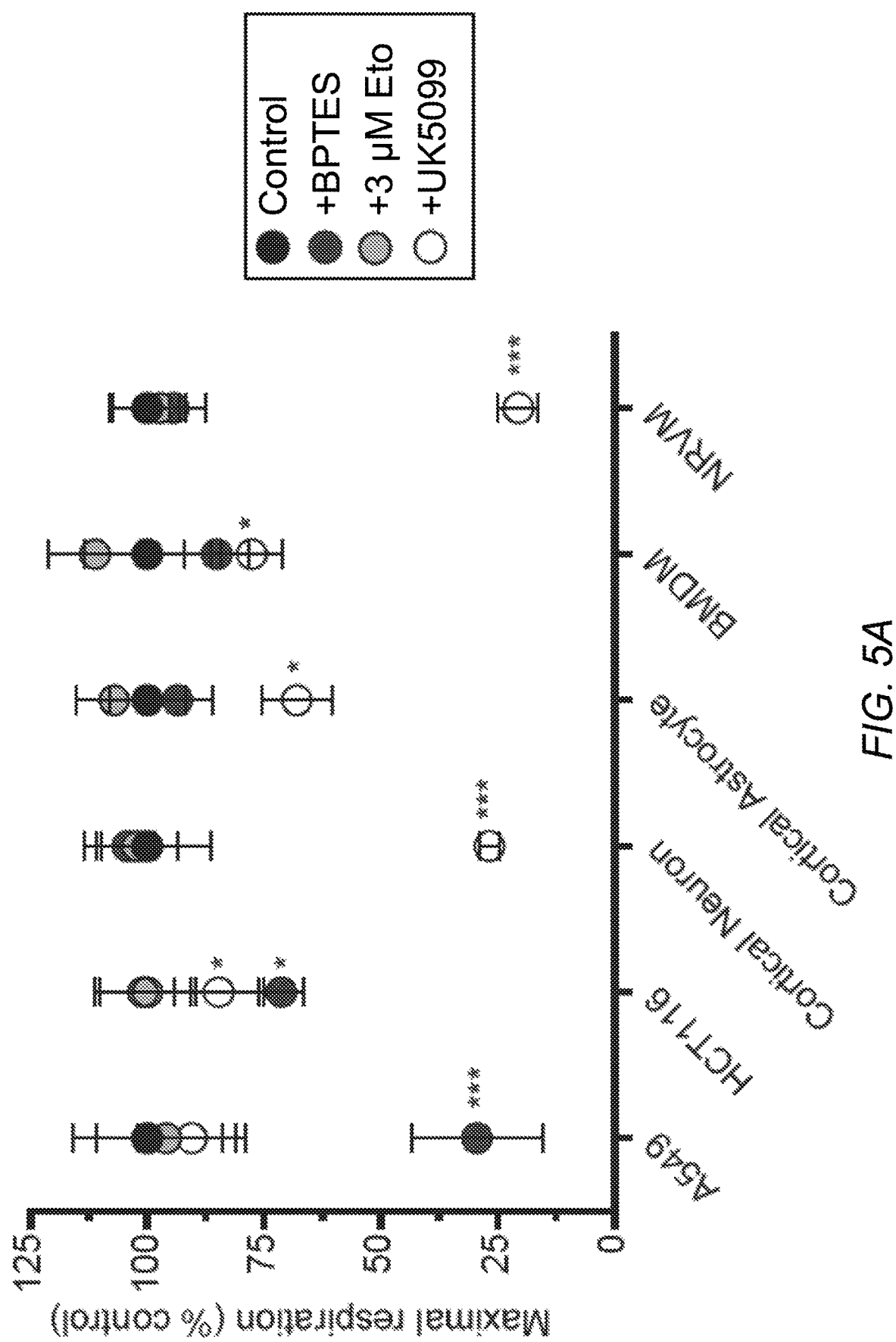
Figure 5B:
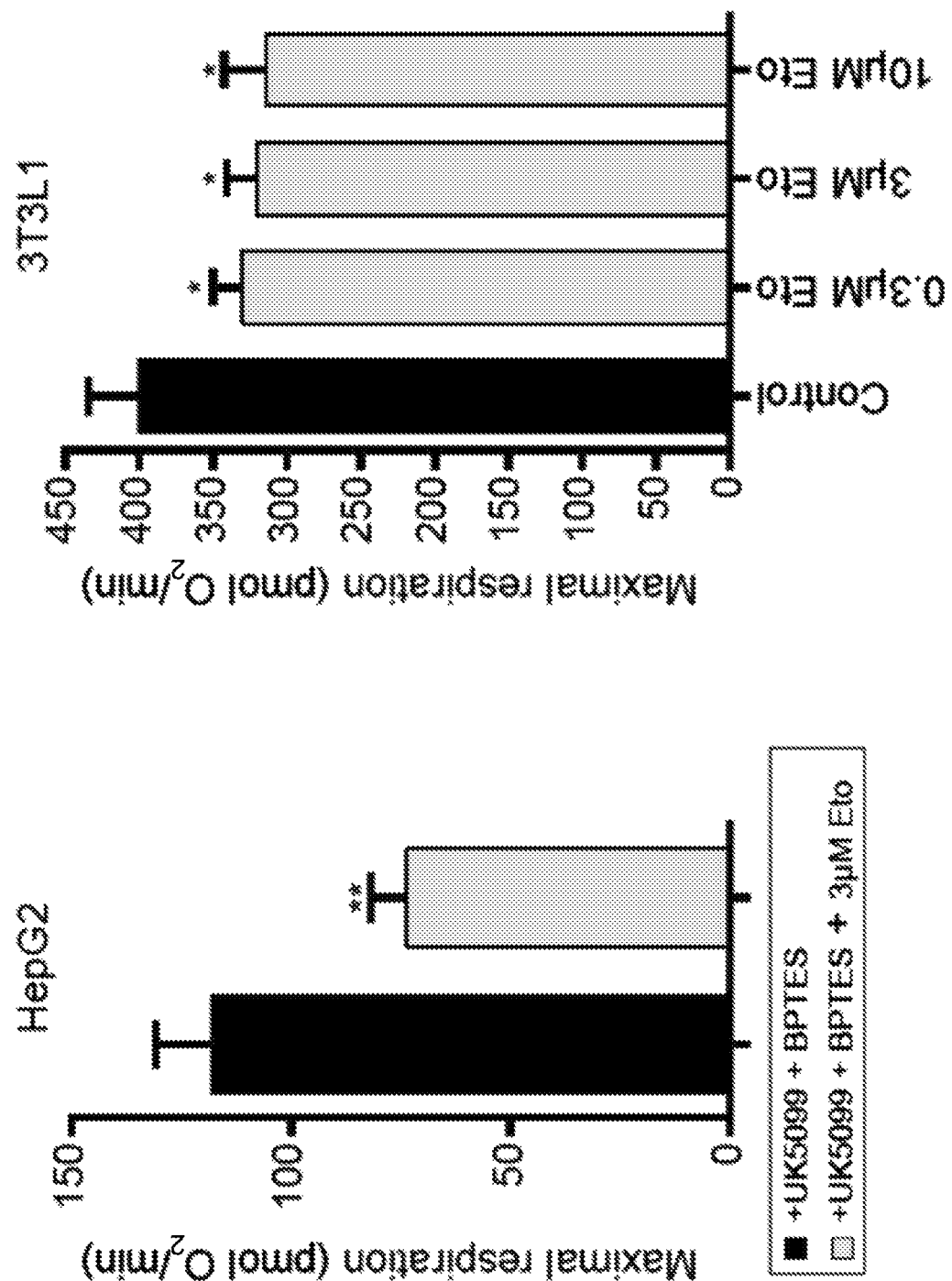

To localize the specific protein(s) inhibited, we first identified assay conditions and cell types in which CPT-1 inhibition with 3 μM etomoxir had no effect on the maximal respiratory rate (FIG. 5A). In six different cell types, this low concentration of etomoxir did not inhibit respiration when intact cells were offered glucose, glutamine, and pyruvate (with no fatty acids or carnitine). This panel included A549s and BMDMs, in which 3 μM etomoxir blocks CPT-1 activity (FIG. 1F). It therefore stands to reason that any effects on respiration from concentrations above 3 μM etomoxir in these cells are attributable to off-target interactions. Indeed, other laboratories have observed a lack of significant changes in respiration under similar conditions in BMDMs at concentrations as high as 100 μM etomoxir, far exceeding the concentration required to maximally inhibit CPT-1. As an important positive control, 3 μM etomoxir was sufficient to inhibit respiration in intact HepG2 hepatoma cells and 3T3-L1 adipocytes (FIG. 5B), cells that can oxidize endogenous LCFAs under certain experimental conditions.

Figure 5C:
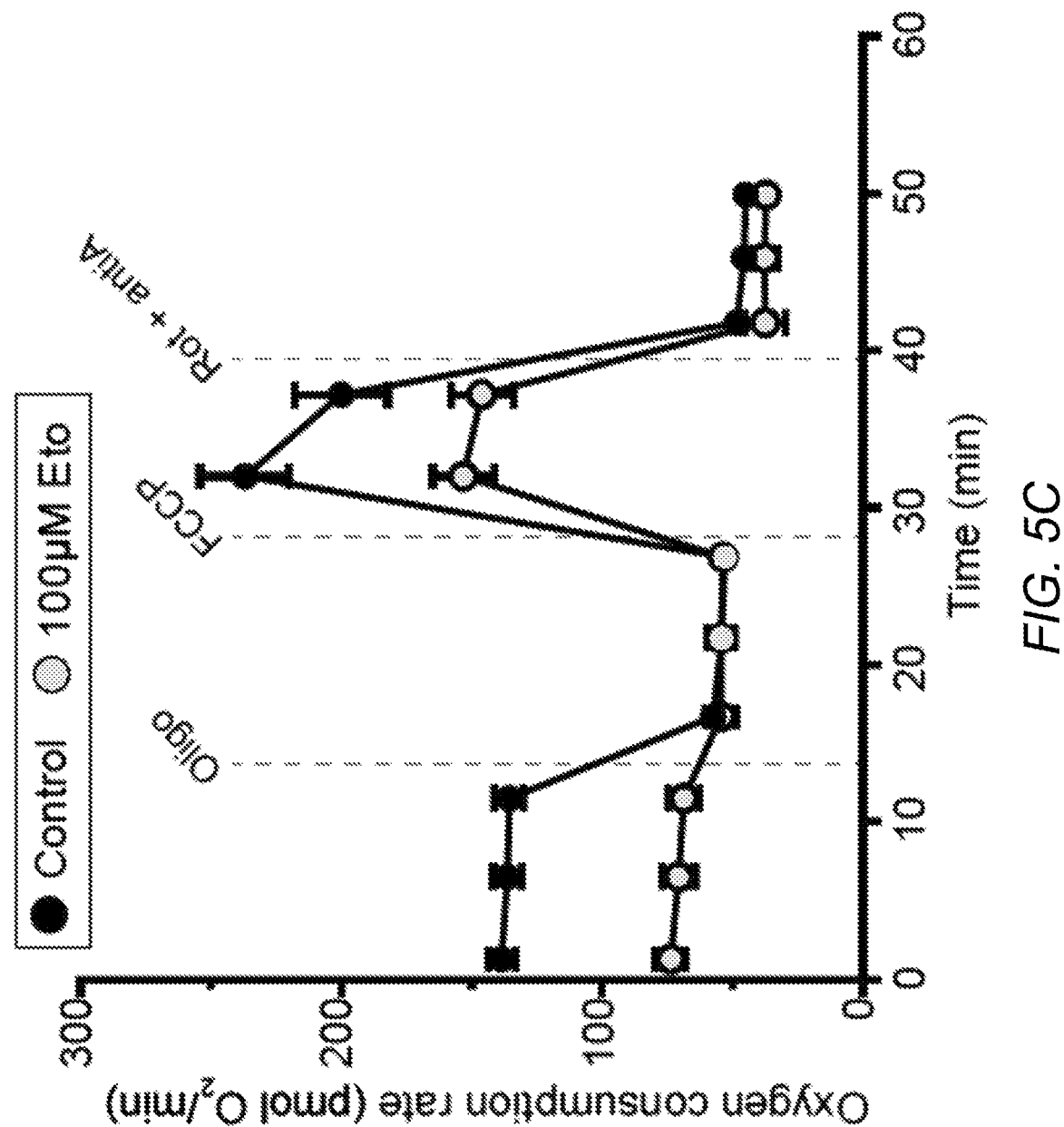
Figure 5D:
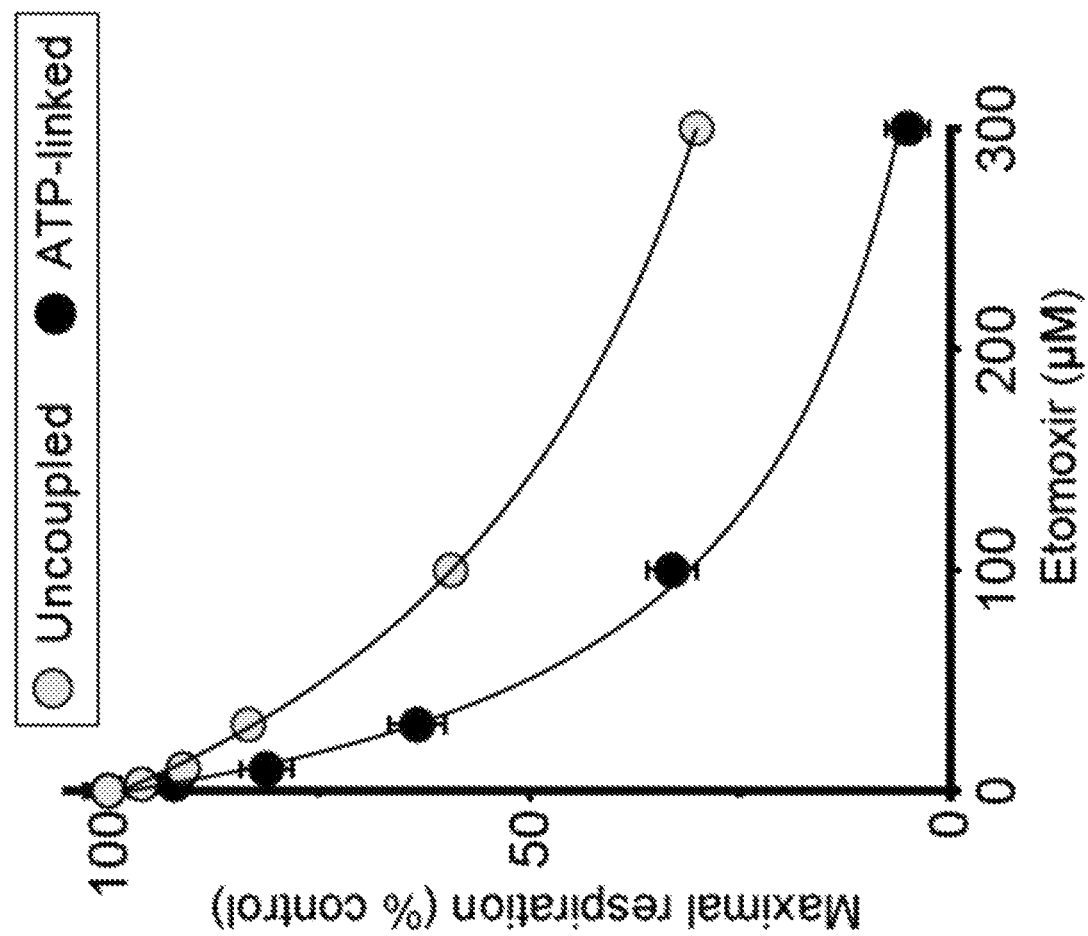
Figure 5E:
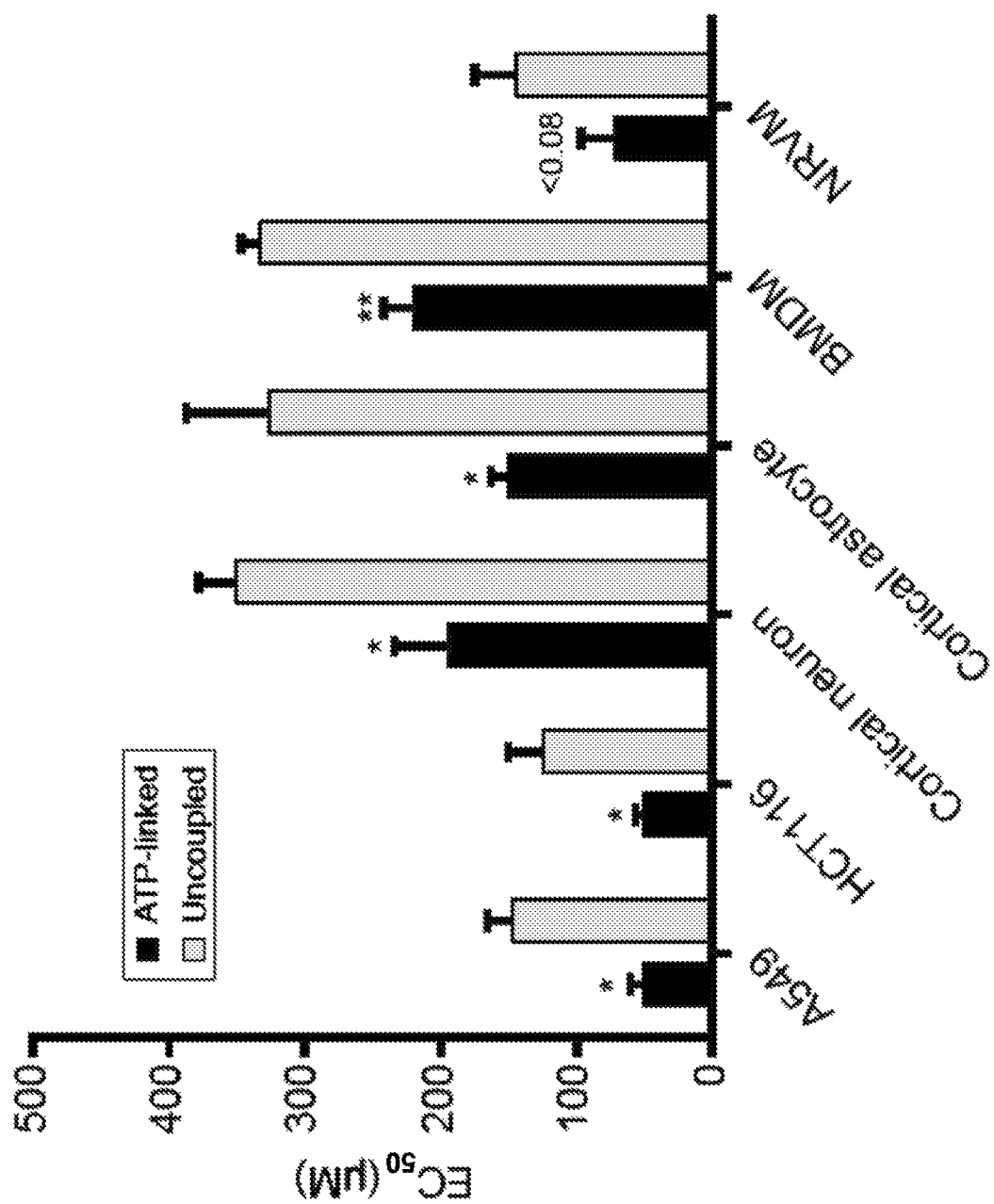

Indeed, in all six cell types tested in FIG. 5A, high concentrations of etomoxir inhibited respiration with a uniform and instructive profile (FIG. 5C, FIG. 5D, FIG. 5E). Inhibitors of the electron transport chain often have greater effects on the maximal FCCP-stimulated rate of respiration (when oxygen consumption is uncoupled from energy metabolism and can approach a maximal rate) compared to respiration coupled to ATP synthesis (when rates are limited by the energy demands of the cell). High concentrations of etomoxir, however, showed the opposite effect: increasing concentrations of etomoxir disproportionately inhibited ATP-linked respiration relative to uncoupler-stimulated respiration (FIG. 5C, FIG. 5D, FIG. 5E). We therefore hypothesized that the primary off-target effect of etomoxir was inhibition of a protein directly involved in ATP synthesis: the ATP synthase, ANT, or the phosphate (Pi) transporter.

Figure 6D:
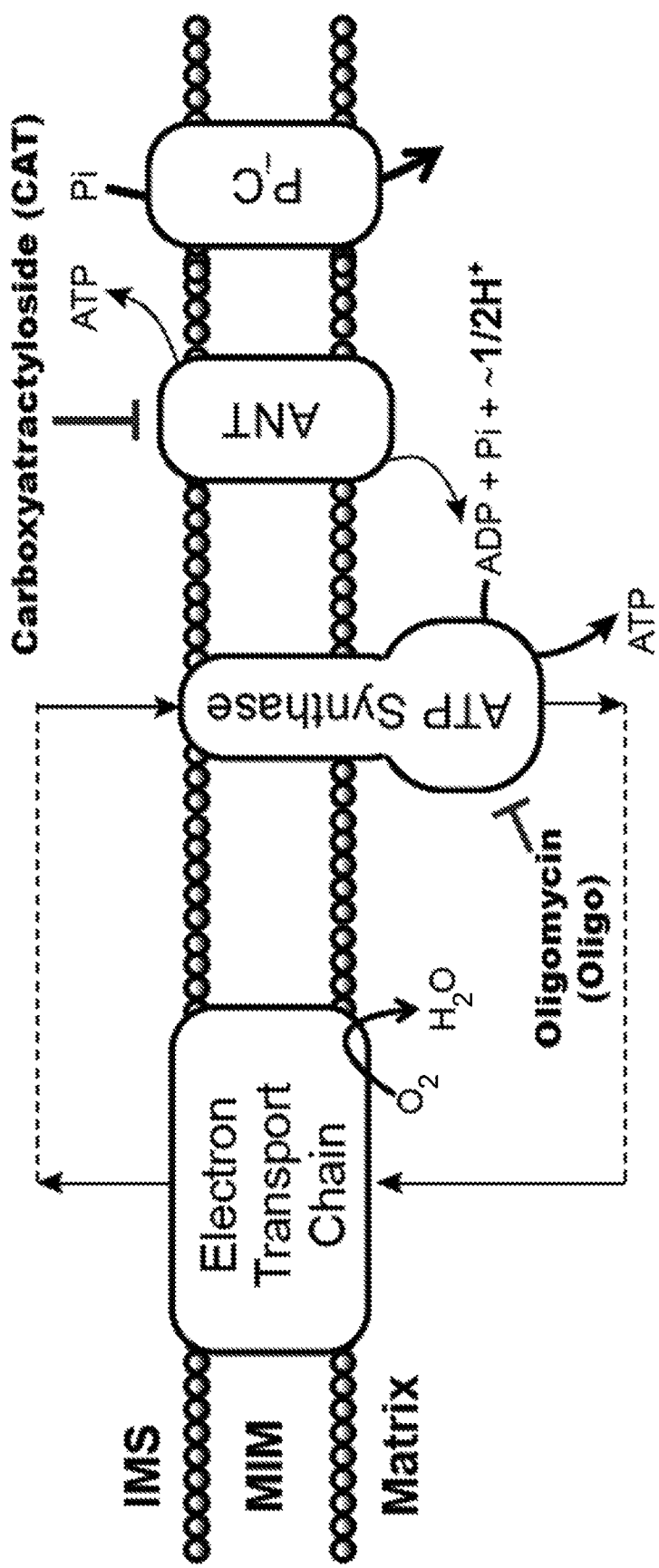
Figure 6D:
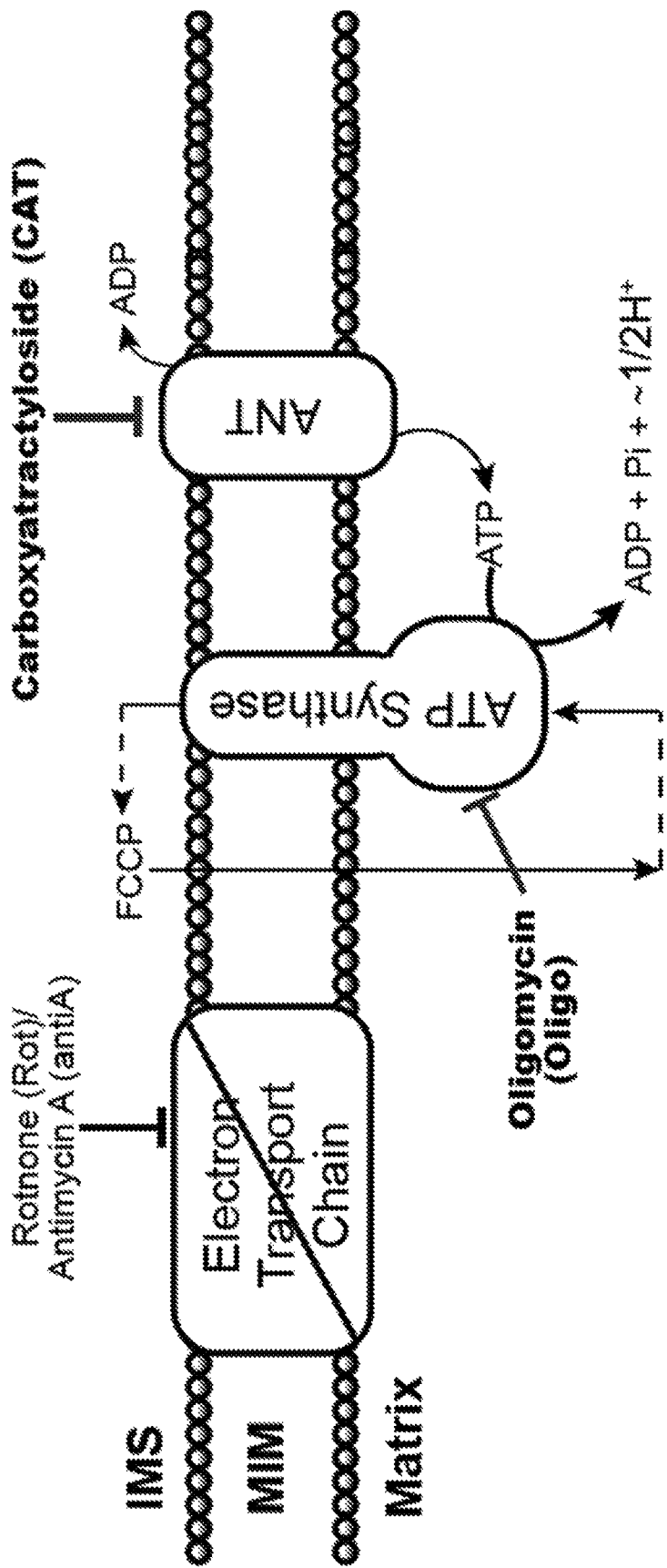
Figure 6E:
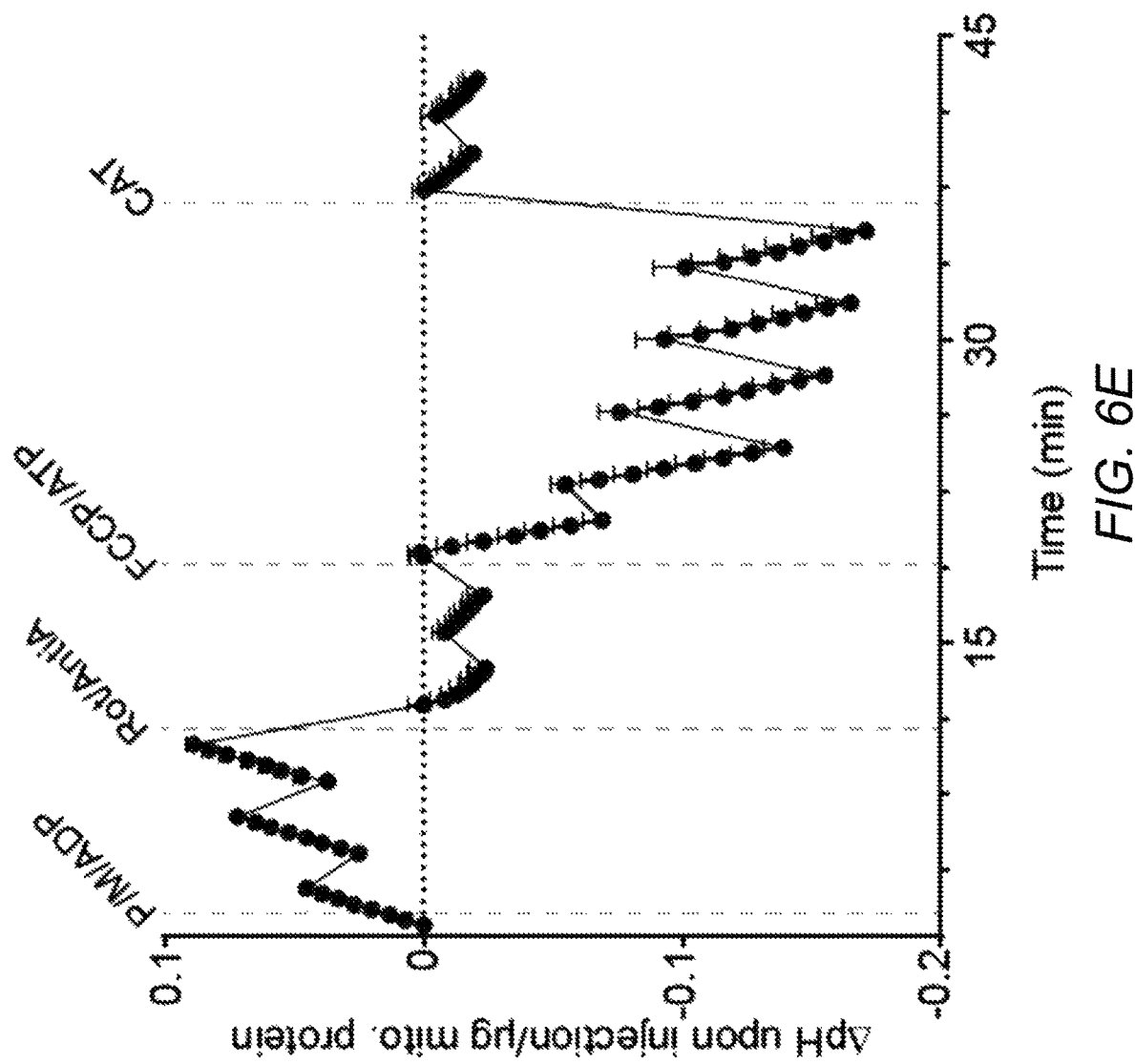

To more directly examine the effect of etomoxir on the enzymes and transporters involved in oxidative phosphorylation, we measured respiration in isolated mitochondria and plasma membrane-permeabilized cells. As expected, high concentrations of etomoxir had a greater inhibitory effect on respiration driven by ADP versus FCCP in both isolated rat liver mitochondria (FIG. 4B) as well as permeabilized cells (FIG. 6A, FIG. 6B), supporting a direct effect of etomoxir on mitochondrial proteins rather than an effect on cytoplasmic ATP-consuming reactions. After showing high etomoxir does not inhibit the Pi transporter (FIG. 6C), we used ATP hydrolysis measurements in isolated mitochondria to discriminate between effects on the ATP synthase versus the ANT (FIG. 4C; FIG. 6D, FIG. 6E). In intact isolated mitochondria, etomoxir inhibited ATP hydrolysis, as did both oligomycin (ATP synthase inhibitor) and carboxyatractyloside (CAT; ANT inhibitor) (FIG. 4C, left; FIG. 6D). However, when alamethicin was used to permeabilize mitochondria to small solutes and eliminate the need for nucleotide transport across the inner membrane, both etomoxir and CAT showed no effect while oligomycin remained inhibitory (FIG. 4C, right; FIG. 6D). Thus, high concentrations of etomoxir inhibit the ANT.

Figure 6F:
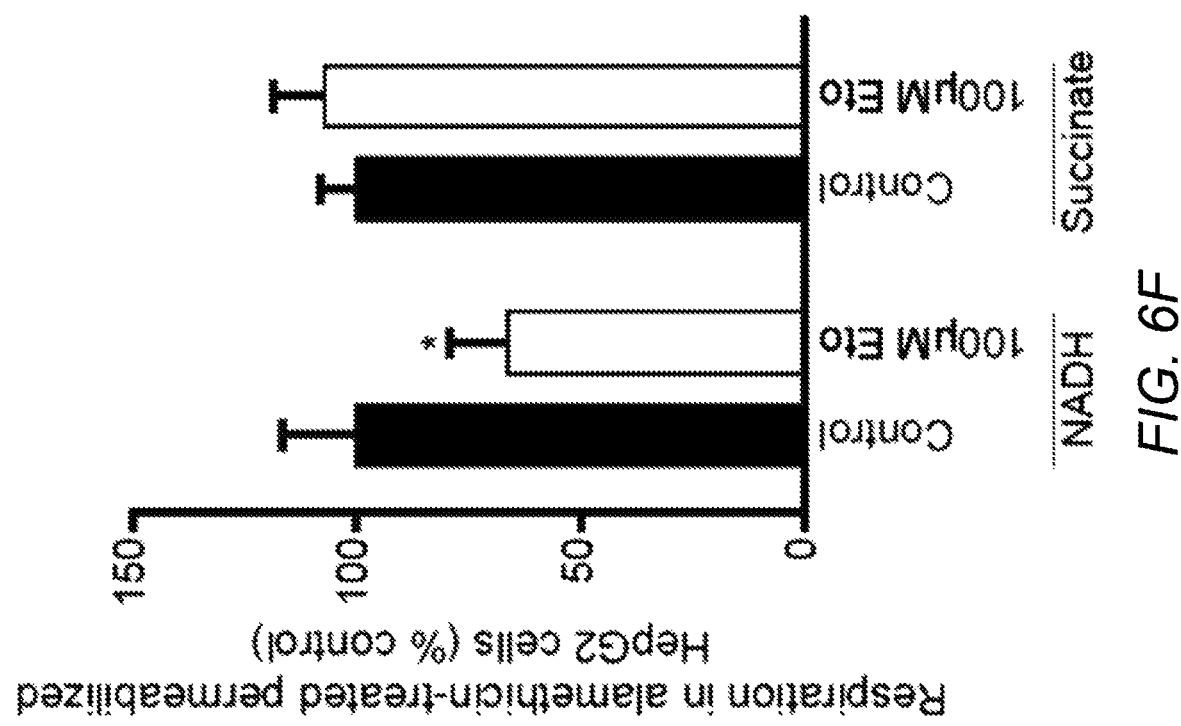

Additionally, oxygen consumption measurements with double-permeabilized cells show high concentrations of etomoxir inhibit oxidation of NADH but not succinate (FIG. 6F). This demonstrates a secondary off-target effect at respiratory complex I, which has been noted by others and provides an explanation for why excess etomoxir also inhibits uncoupler-stimulated respiration (FIG. 4B, FIG. 6A, FIG. 6B). A similar profile of a pronounced off-target effect on phosphorylating respiration with a secondary effect at uncoupled respiration is apparent in both BMDMs and Treg cells, and is independent of CPT-1 activity in both cell types (FIG. 6G). We examined whether off-target effects on oxidative phosphorylation can also explain why etomoxir blocks M(IL-4) polarization.

Detailed description of FIG. 4. Excess etomoxir has off-target effects on mitochondrial bioenergetics, but these cannot explain its inhibition of M(IL-4). (FIG. 4A) Effects of 200 μM etomoxir on basal mitochondrial respiration in intact WT, Cpt1a−/−, and Cpt2−/− BMDMs. Cells were offered 8 mM glucose, 2 mM glutamine, and 2 mM pyruvate (no fatty acids or carnitine) in the experimental medium. (n=4 independent biological replicates). (FIG. 4B) ADP-stimulated (State 3) or maximal FCCP-stimulated respiration was measured±100 μM etomoxir in isolated rat liver mitochondria. Mitochondria were offered pyruvate/malate as respiratory substrates. (n=4 independent biological replicates) (FIG. 4C) Inhibition of ANT activity was assessed by measuring the rate of ATP hydrolysis in both intact (left) and permeabilized (right) rat liver mitochondria. ATP hydrolysis acidifies the experimental medium (see FIG. 4). Mitochondria were treated with alamethicin to permeabilize the inner membrane to small solutes such as ATP to discriminate between effects of ATP transport versus hydrolysis, Eto., etomoxir (100 μM); CAT, carboxyatractyloside (7.5 ng/mg mito. protein); Oligo., oligomycin (3 ng/mg mito. protein). (n=4 independent biological replicates) (FIG. 4D) Basal mitochondrial respiration in intact BMDMs after 24 hr treatment with 200 μM etomoxir (Eto), 200 nM rotenone (Rot), 200 nM antimycin A (antiA), 1.2 μM oligomycin (Oligo), or 5 μM carboxyatractyloside (CAT). (n=4 independent biological replicates). (FIG. 4E) Cellular ATP production rates were estimated as the sum of ATP generated from oxidative phosphorylation and glycolysis. BMDMs were treated with IL-4 for 24 hr±200 μM etomoxir or 200 nM rotenone. (n=4 independent biological replicates). See also FIG. 5, FIG. 6, FIG. 7.

Detailed description of FIG. 5. (FIG. 5A) Maximal FCCP-stimulated respiration in response to 3 μM etomoxir in six cell types (experimental conditions in Materials and Methods). As positive controls, all cell types showed sensitivity to either the glutaminase inhibitor BPTES or the mitochondrial pyruvate carrier inhibitor UK5099 (both at 3 μM). (n≥3 independent biological replicates). (FIG. 5B) (Left) Maximal respiration in HepG2 cells offered 8 mM glucose, 2 mM glutamine, and 2 mM pyruvate in the experimental medium with BPTES and UK5099 (both at 3 μM)±3 μM etomoxir. (n=4 independent biological replicates). (Right) Maximal respiration in 3T3-L1 adipocytes offered 1 mM glucose and 0.5 mM carnitine in the experimental medium with increasing concentrations of etomoxir. (n=3 independent biological replicates). (FIG. 5C) Sample respirometry trace of A549 cells offered 8 mM glucose, 2 mM glutamine, and 2 mM pyruvate in the experimental medium±100 μM etomoxir. (n=5 technical replicates). (FIG. 5D) Sample concentration-response curve of ATP-linked and maximal FCCP-stimulated respiration in A549 cells [conditions as in (FIGS. 5A & FIG. 5C)] in response to increasing concentrations of etomoxir. (n=5 technical replicates). (FIG. 5E) Aggregate EC50 values for the inhibition of ATP-linked and maximal FCCP-stimulated respiration by etomoxir in a range of intact cells. Experimental conditions are as in (FIG. 5A) and available in Materials and Methods. (n≥3 independent biological replicates)

Detailed description of FIG. 6. (FIG. 6A) Sample respirometry trace of permeabilized HepG2 cells offered pyruvate/malate and either 30 μM or 300 μM of etomoxir. (n=5 technical replicates). (FIG. 6B) Aggregate EC50 values for the inhibition of ATP-linked and maximal FCCP-stimulated respiration by etomoxir in permeabilized HepG2 or A549 cells. Pyr, cells offered pyruvate/malate as respiratory substrates; Glu, glutamate/malate; Gln, glutamine (no malate required). (n=4 independent biological replicates). (FIG. 6C) Phosphate-induced swelling assay in isolated rat liver mitochondria. Loss of absorbance reflects mitochondrial swelling due to activity of the Pi carrier (see Materials and Methods). Etomoxir does not affect the rate of swelling as there was no change in loss of absorbance relative to the control. As expected, inhibitors of mitochondrial carriers including N-ethyl maleimide (NEM) and mersalyl both inhibited the rate of swelling. As a positive control for rapid and complete loss of absorbance, 10 μg/mL alamethicin (Alm) was used to permeabilize the inner membrane to small solutes and induce osmotic swelling. (FIG. 6D) Scheme depicting how ATP hydrolysis can be measured by pH changes in the experimental medium. Phosphorylating respiration will alkalinize the experimental medium (top), and ATP hydrolysis by the ATP synthase will acidify the experimental medium. IMS, intermembrane space; MIM, mitochondrial inner membrane. (FIG. 6E) A sample kinetic trace using isolated rat liver mitochondria showing pH changes in the experimental medium in response to ATP synthesis or hydrolysis by the ATP synthase. P/M/ADP, pyruvate/malate/ADP; rot/antiA, 2 μM rotenone/1 μM antimycin A.; FCCP/ATP, 1 μM FCCP and 25 mM ATP; CAT, 5 μg/mg mito. Protein carboxyatractyloside. (n=10 technical replicates). (FIG. 6F) Effects of 100 μM etomoxir in "double-permeabilized" HepG2 cells. In the presence of both rPFO (plasma membrane permeabilization) and 10 ug/mL alamethicin (mitochondrial membrane permeabilization), NADH and succinate can reach the matrix side of the inner membrane unimpeded, allowing, respectively, direct measurement of complex I- and complex II-mediated respiration. [NADH], 2 mM; [succinate], 5 mM. Both NADH (2 mM) and succinate (5 mM) were added in the presence of 10 μM cytochrome c. (n=4 independent biological experiments). (FIG. 6G) ADP-stimulated (State 3) or maximal FCCP-stimulated respiration was measured in permeabilized WT, Cpt1a−/−, and Cpt2−/− BMDMs±200 μM etomoxir. Permeabilized cells were offered pyruvate/malate as respiratory substrates. (n=4 independent biological replicates).

Example 4. Oxidative Phosphorylation does not Regulate Many Markers of M(IL-4) Polarization To test whether the inhibitory effects at the ANT and complex I could explain inhibition of IL-4-driven macrophage polarization by 200 μM etomoxir, we measured whether other inhibitors of oxidative phosphorylation could phenocopy this effect. Specifically, we used compounds that block both ATP synthesis (CAT or oligomycin) and respiratory chain activity (rotenone, piericidin A, or antimycin A; FIG. 4D). Indeed, each of the five compounds strongly reduced respiration at 24 hr., well beyond the extent of inhibition by etomoxir (FIG. 4E, FIG. 7A). Additionally, and as is expected with potent respiratory chain blockers, rates of 3H2O release from 9,10-3H-palmitate showed rotenone or antimycin A suppressed LCFA oxidation to levels in line with 200 μM etomoxir (FIG. 7B). Remarkably, however, none of the inhibitors of ATP synthesis or the electron transport chain significantly lowered the population of CD206+/CD71+ cells (FIG. 4F, FIG. 7C, FIG. 7D), suggesting that inhibition of oxidative phosphorylation cannot explain the effects of excess etomoxir on M(IL-4) polarization.

Figure 4G:
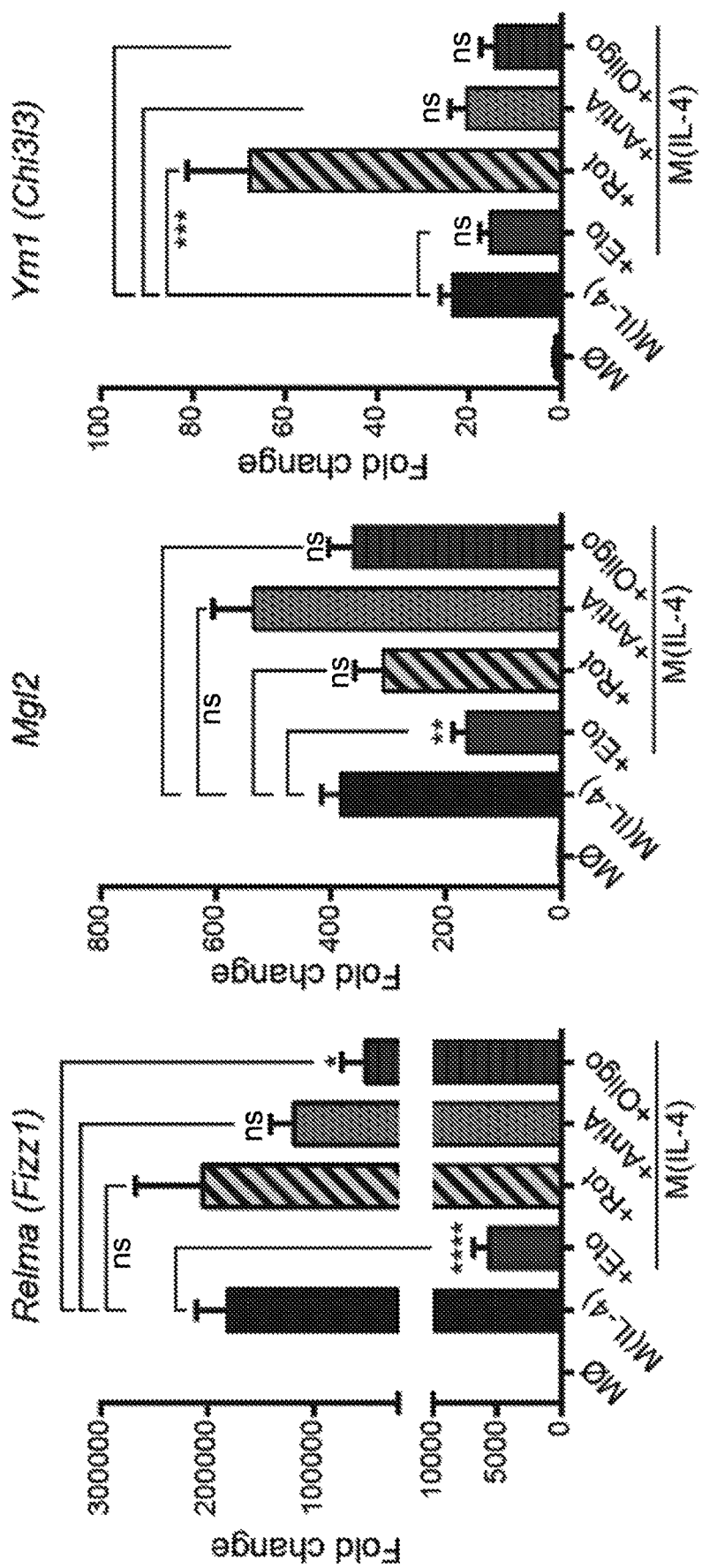
Figure 4G:
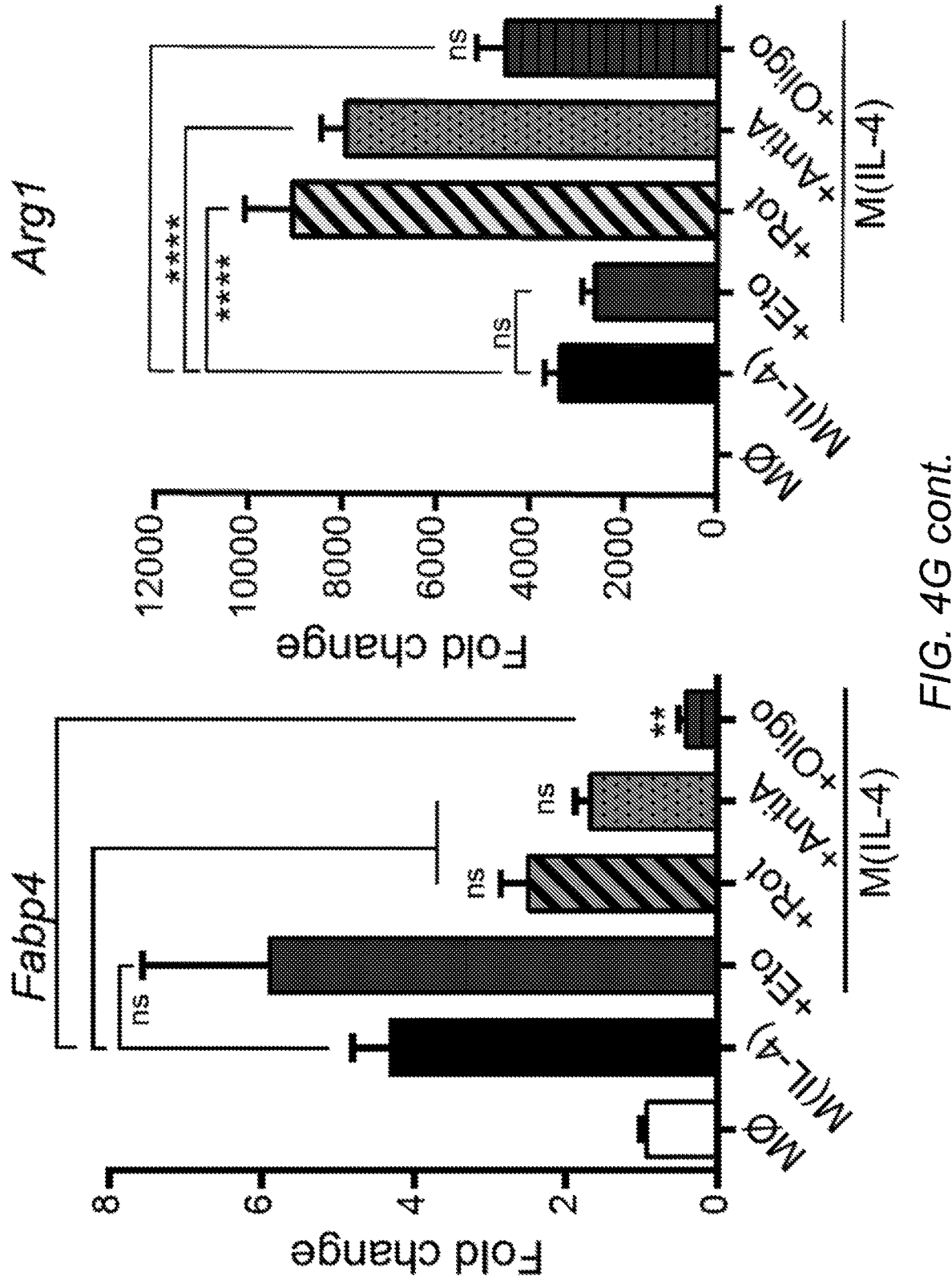
Figure 7E:
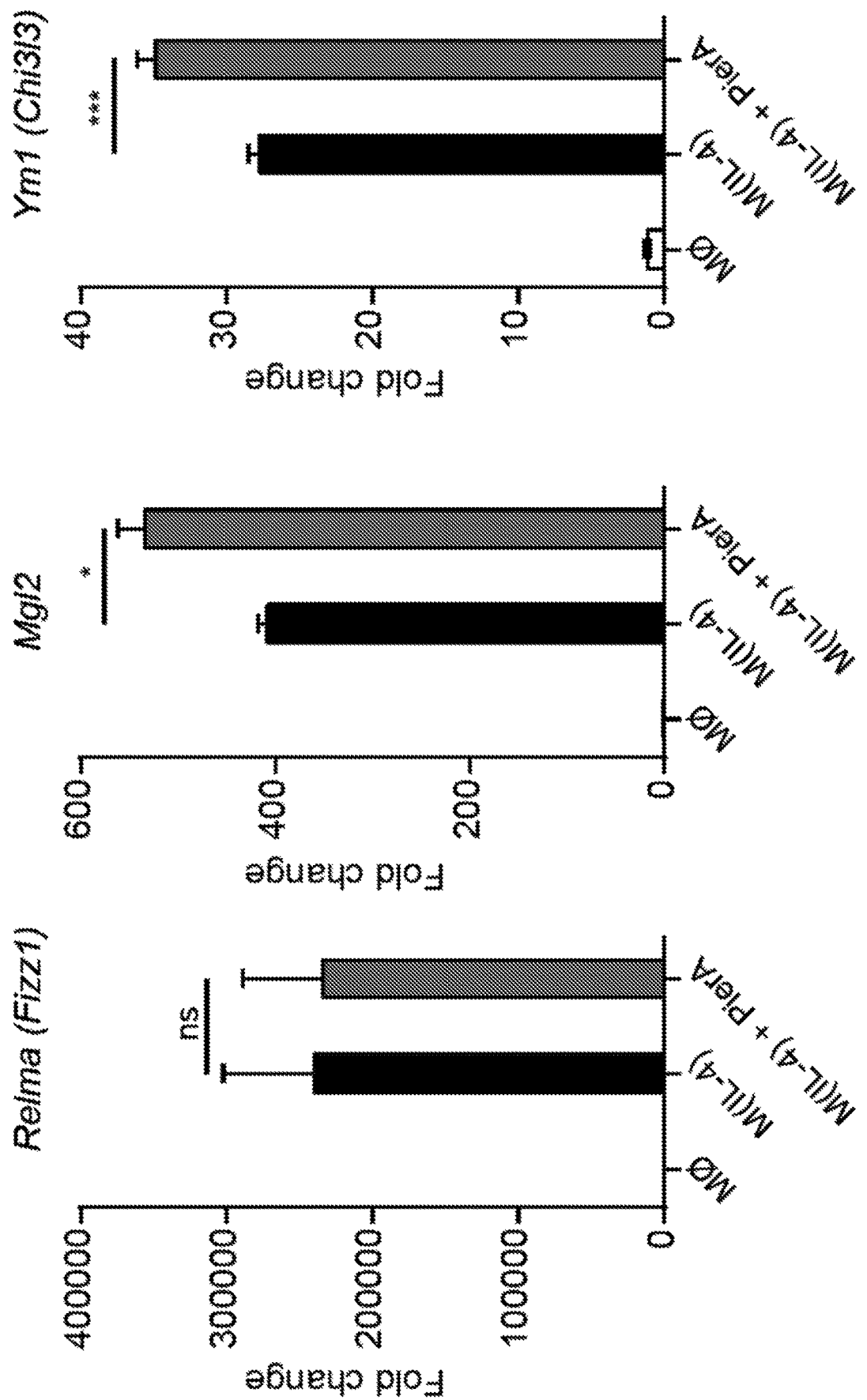
Figure 7E:
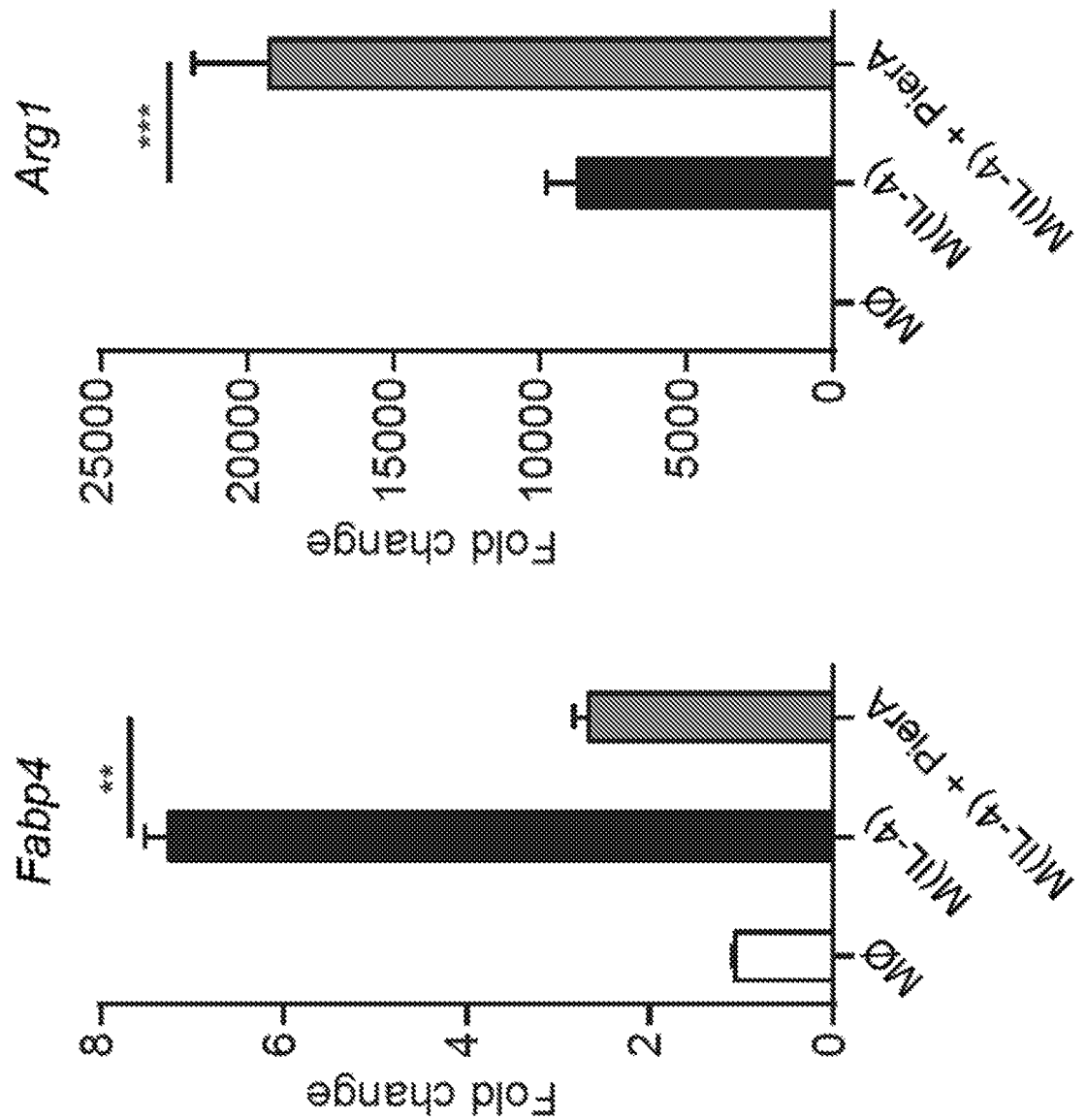

Gene expression results further confirmed that the mechanism by which etomoxir blocks alternative macrophage activation is distinct from electron transport chain activity and oxidative mitochondrial metabolism (FIG. 4G, FIG. 7E). In the same way that only a subset of IL-4-associated genes was affected by high concentrations of etomoxir (FIG. 2B), inhibitors of oxidative phosphorylation had a mosaic-like effect on IL-4-responsive genes, and varied based on the site of inhibition. The most striking observation was that rotenone, piericidin A, and antimycin A, potent inhibitors of the electron transport chain, failed to reduce IL-4-induced expression of Relma, Ym1, and Mgl2, all of which were significantly decreased (relative to IL-4) by 200 μM etomoxir (FIG. 2B, FIG. 4G). Moreover, the complex I inhibitors rotenone and piericidin A actually increased expression of Ym1 and Arg1, but similar changes were not observed with the ATP synthase inhibitor oligomycin (FIG. 4G, FIG. 7E). Further separating the effects of etomoxir from respiratory chain activity, Fabp4 expression was unresponsive to etomoxir despite being sensitive to other mitochondrial inhibitors (FIG. 4G, FIG. 7E).

Figure 4H:
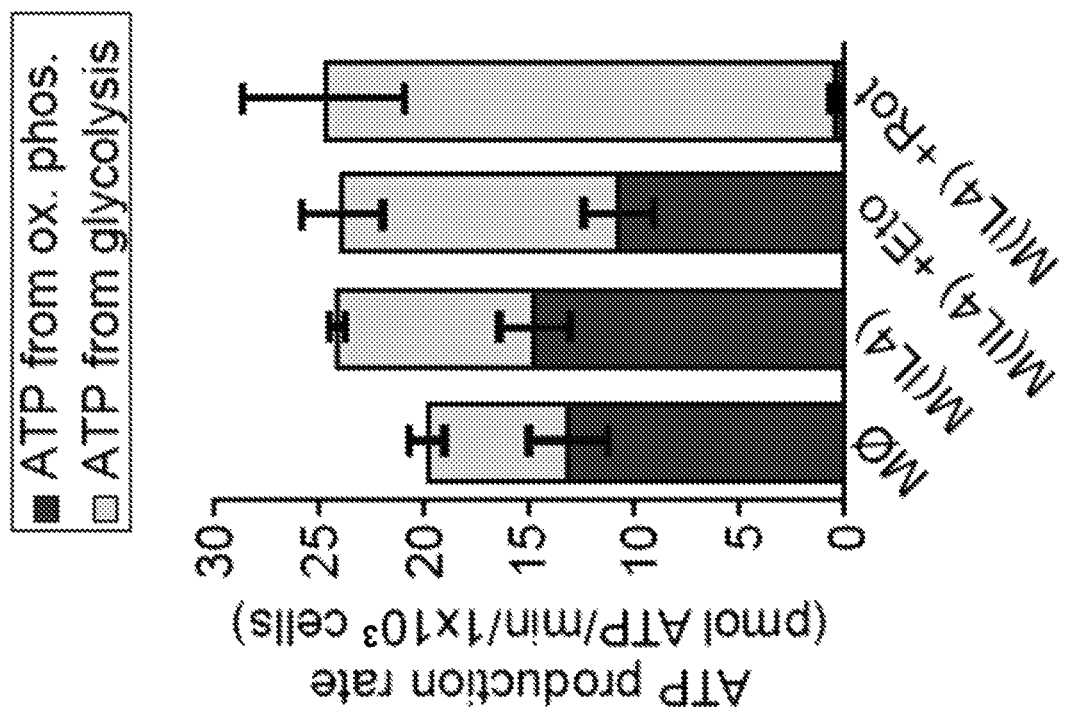

Finally, to demonstrate that rotenone-treated BMDMs were not bioenergetically compromised, we estimated rates of ATP synthesis using respirometry and matched enzymatic lactate assays. Although complex I inhibition with rotenone predictably limited ATP production from oxidative phosphorylation, IL-4-treated BMDMs sufficiently increased glycolytic ATP production to maintain overall rates of energy metabolism (FIG. 4H). Thus, high concentrations of etomoxir inhibit alternative macrophage activation by a mechanism independent from its off-target effects on mitochondrial ATP synthesis.

Detailed description of FIG. 7. (FIG. 7A) Basal mitochondrial respiration in intact BMDMs after 24 hr treatment with 100 nM piericidin A (PierA). (n=4 independent biological replicates). (FIG. 7B) Measurement of β-oxidation in IL-4-stimulated BMDMs treated with etomoxir (either 3 or 200 μM), rotenone (200 nM) or antimycin A (200 nM). Data represents three independent experiments. (FIG. 7C) Normalized cell counts from Seahorse XF96 plates for WT BMDM stimulated with IL-4 and co-treated with 200 μM etomoxir (Eto), 200 nM rotenone (Rot), 200 nM antimycin A (AntiA), 1.2 μM oligomycin (Oligo), or 5 μM carboxyatractyloside (CAT) for 24 hr. (FIG. 7D) Flow cytometric analysis for CD206, CD71, and CD301 in BMDMs stimulated with IL-4±200 nM rotenone or 100 nM piericidin A (PierA, co-treated with IL-4) for 48 hr. The data shown are from one experiment representative of a total of four independent biological replicates. (FIG. 7E) qPCR analysis of Relma, Mgl2, Ym1, Fabp4, and Arg1 after 24 hr treatment of IL-4±100 nM piericidin A for 24 hr. (n=3 independent biological experiment).

Example 5. High Concentrations of Etomoxir Disrupt CoA Homeostasis

Having eliminated reduced oxidative phosphorylation as the mechanism by which etomoxir inhibits M(IL-4) polarization, we then searched for other off-target effects that could explain its blockade of alternative macrophage activation. Given the well-documented polypharmacology of etomoxir, several promiscuous effects of the drug on metabolism have been identified in the literature, including inhibition of fatty acid and cholesterol synthesis (off-target transcriptional agonism), and depletion of cytoplasmic CoA. We therefore conducted a metabolomics screen for an unbiased analysis of what pathways might be most differentially affected between a low, specific concentration of etomoxir and a high, non-specific concentration during M(IL-4) polarization. Indeed, a principal component analysis (PCA) showed that treatment of IL-4 stimulated macrophages with 200 μM etomoxir caused a profound change in the metabolite composition of BMDMs relative to untreated or IL-4-stimulated macrophages (FIG. 8A). As important controls, the PCA showed not only that IL-4 stimulation created a shift in the metabolite profile of BMDMs relative to untreated cells, but also that there was no appreciable change in IL-4-treated cells upon CPT-1 inhibition with 3 μM etomoxir.

Figure 9A:
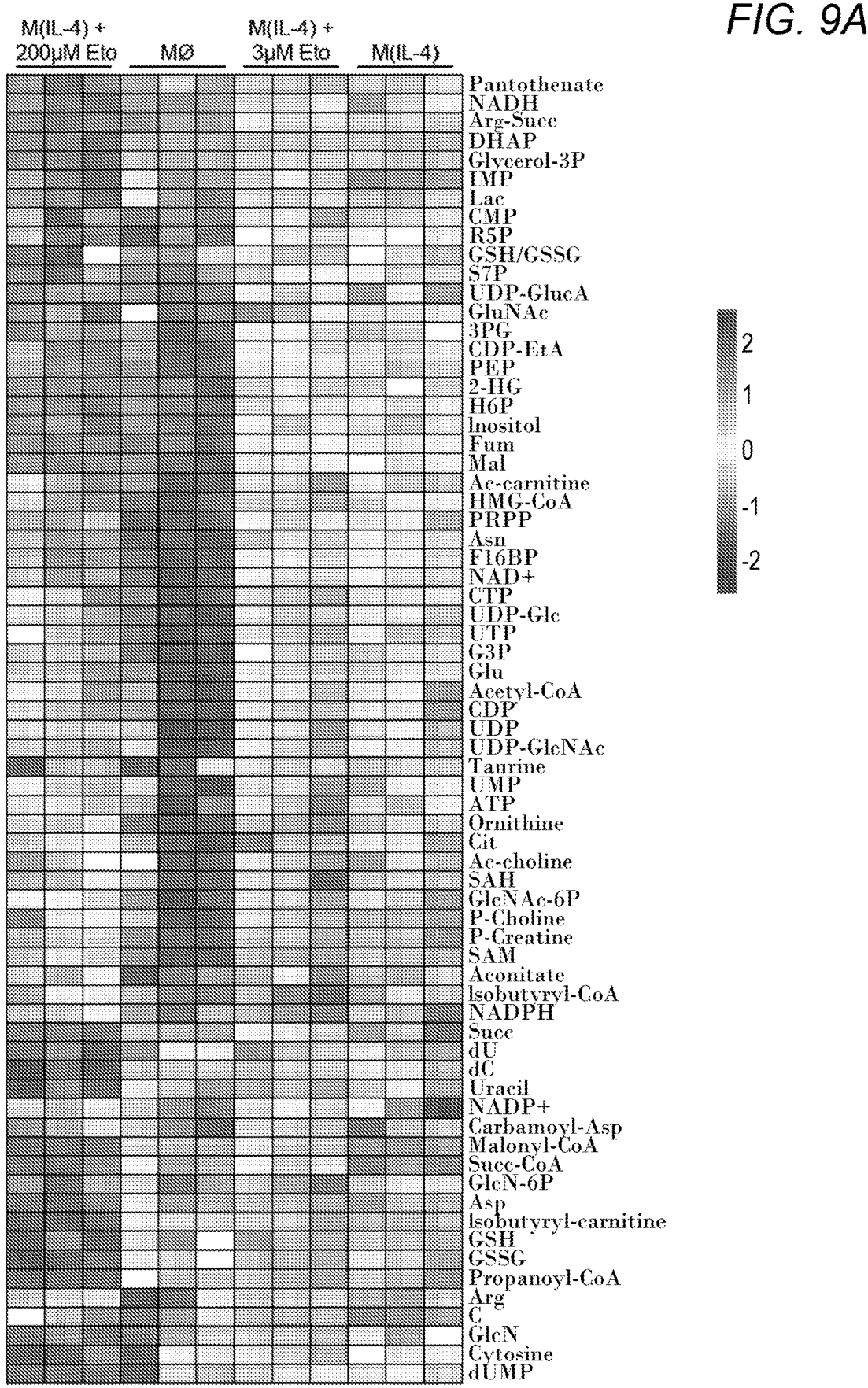

We then identified which metabolites were most altered by treatment with 200 μM etomoxir. The largest change observed was in pantothenate: excess etomoxir raised intracellular levels by three-fold whereas there was no change among untreated controls, IL-4-stimulated macrophages, and BMDMs treated with IL-4 and 3 μM etomoxir (FIG. 8B; FIG. 9A). Pantothenate (also known as vitamin B5) is the precursor for the biosynthesis of coenzyme A, which is an obligatory co-factor central to a broad range of metabolic pathways. This data, coupled with the fact that the active inhibitor against CPT-1 is the etomoxiryl-CoA thioester (a palmitoyl CoA mimetic generated by long chain acyl CoA synthetase), led us to explore whether excess etomoxir caused dysregulated CoA homeostasis.

Specifically, we hypothesized that high concentrations of etomoxir could sequester appreciable amounts of CoA as etomoxiryl-CoA. Free cytoplasmic CoA levels in mammalian tissues are estimated to range between 20-230 μM, though intramitochondrial concentrations are generally an order of magnitude greater. As such, if cytoplasmic levels of free CoA broadly match the concentrations of etomoxir required to block macrophage polarization, then formation of etomoxiryl-CoA from excess etomoxir could deplete free CoA below threshold levels necessary for IL-4-driven responses. As predicted, enzymatic measurements of free CoA showed that 200 μM significantly dropped intracellular CoA levels of IL-4-treated BMDMs (FIG. 8C). This loss of intracellular free CoA, however, could be restored by supplementation of CoA to the medium in these phagocytic cells. Additionally, provision of CoA in the absence of etomoxir significantly increased intracellular levels beyond IL-4-treated controls.

Detailed description of FIG. 8. Etomoxir disrupts intracellular CoA homeostasis. (FIG. 8A) principal component analysis of untargeted metabolomics data from WT BMDM after 24 hr. IL-4-treatment±3 μM or 200 μM etomoxir (co-treated with IL-4; n=3 technical replicates). The percent variance explained is indicated. Prediction ellipses are drawn such that a new observation from the same group will fall inside the ellipse with 95% certainty. (FIG. 8B) Intracellular pantothenate levels as measured by LC/MS in conditions as in (FIG. 8A). (FIG. 8C) Intracellular free coenzyme A (CoASH) measurement in BMDMs after 20 hr treatment with IL-4±200 μM etomoxir and ±500 μM CoA (all co-treatments with IL-4). The data shown are three independent biological replicates. See also FIG. 9.

Detailed description of FIG. 9. (FIG. 9A) Heat map of LC-MS metabolomics data showing the 70 metabolites with an ANOVA p-value≤0.05 from WT BMDM, 24 hr. IL-4 stimulation, IL-4+3 μM etomoxir, and IL-4+200 μM etomoxir. Cells were co-treated with IL-4 and etomoxir. Data are from three technical replicates. Bar reflects scaled relative amounts of metabolites across conditions. (FIG. 9B) Basal mitochondrial respiration in intact BMDMs after 24 hr treatment with IL-4±500 μM CoA. (n=4 independent biological replicates). (FIG. 9C) Flow cytometric analysis of the CD206+/CD71+ population in WT and Cpt2−/− BMDMs in response to IL-4±200 μM etomoxir±500 μM CoA. The data shown are from one experiment representative of a total of three independent biological replicates. (FIG. 9D) Flow cytometric analysis of the CD206+/CD71+ population in WT and CD11c-Cre Cpt1−/− BMDMs in response to IL-4±200 μM etomoxir±500 μM CoA. The data shown are from one experiment representative of a total of two independent biological replicates.

Example 6. Exogenous CoA Restores Expression of IL-4-Associated Markers

Figure 9B:
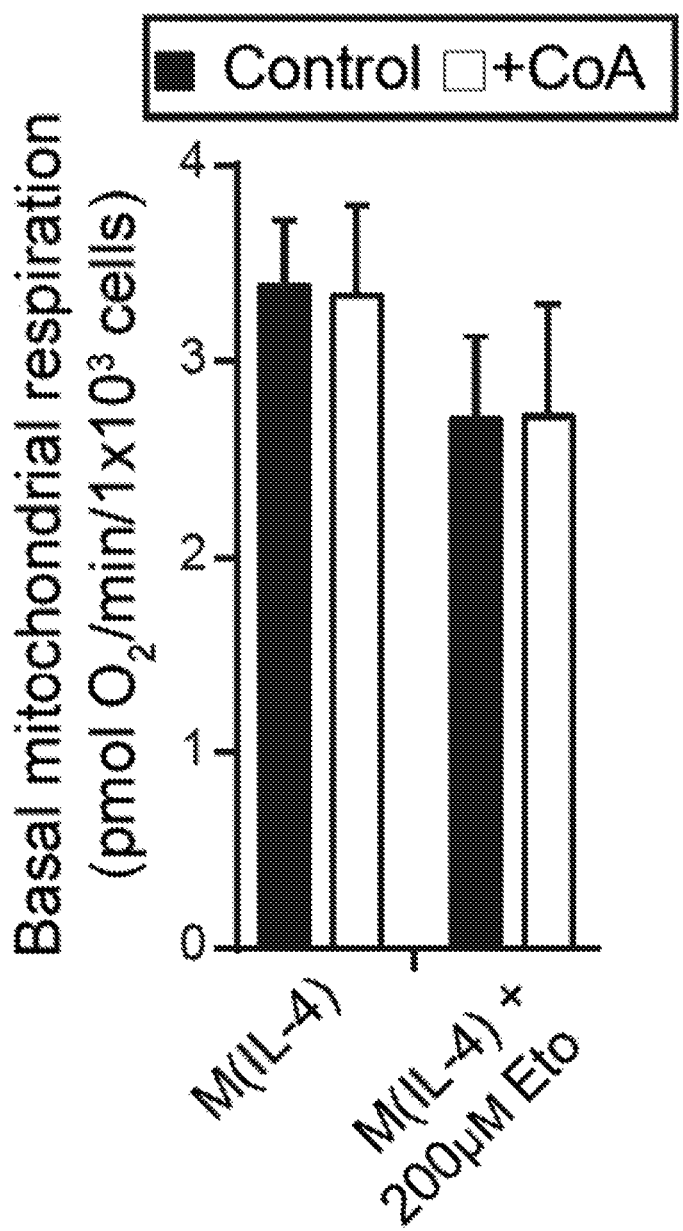
Figure 9C:
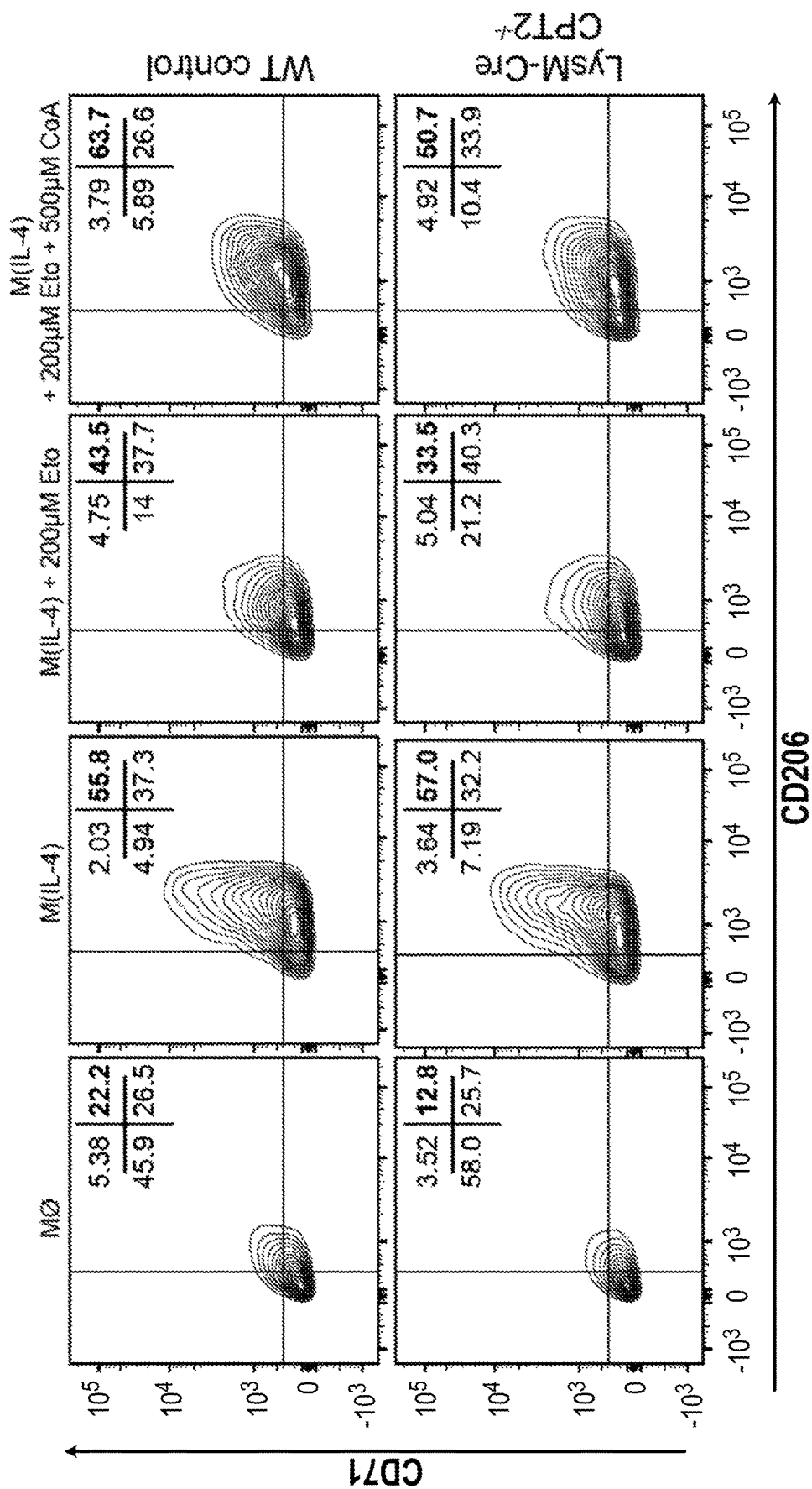
Figure 10A:
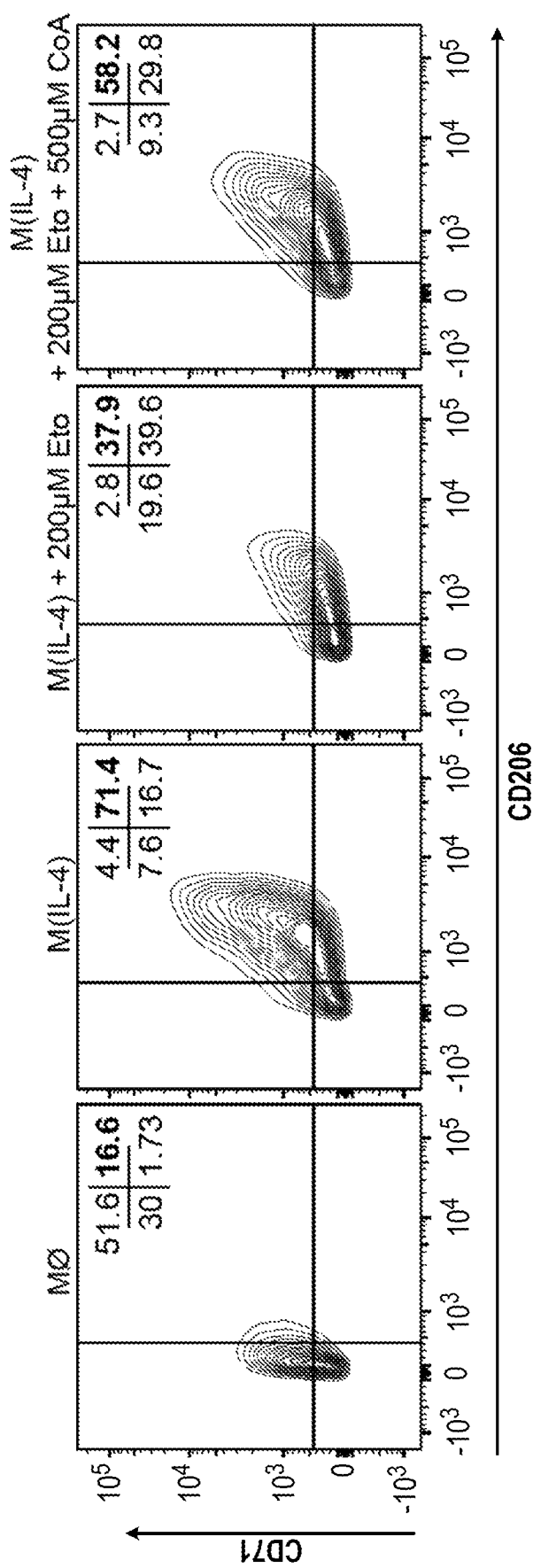
Figures 10B, 10C:
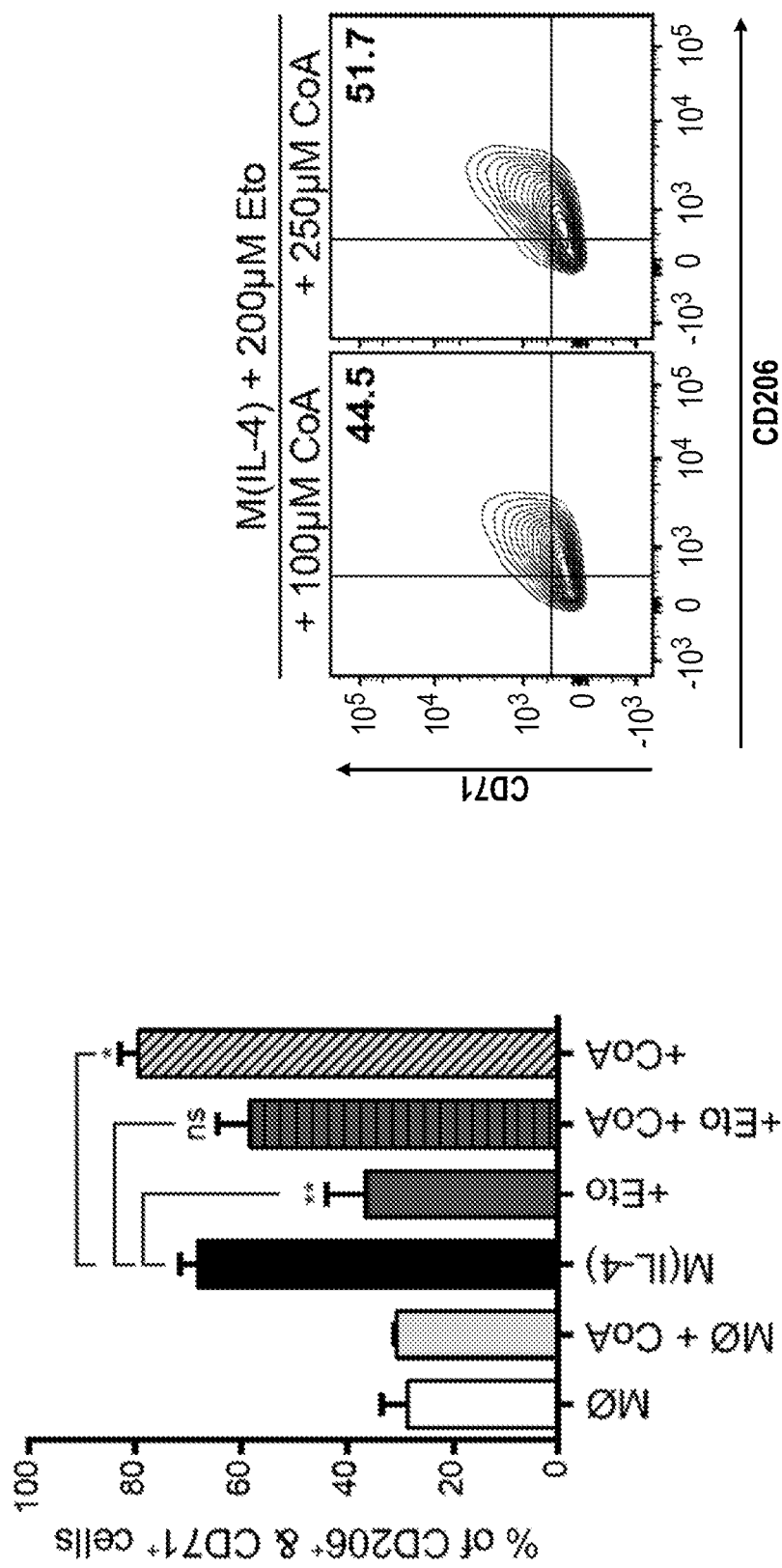
Figure 10D:
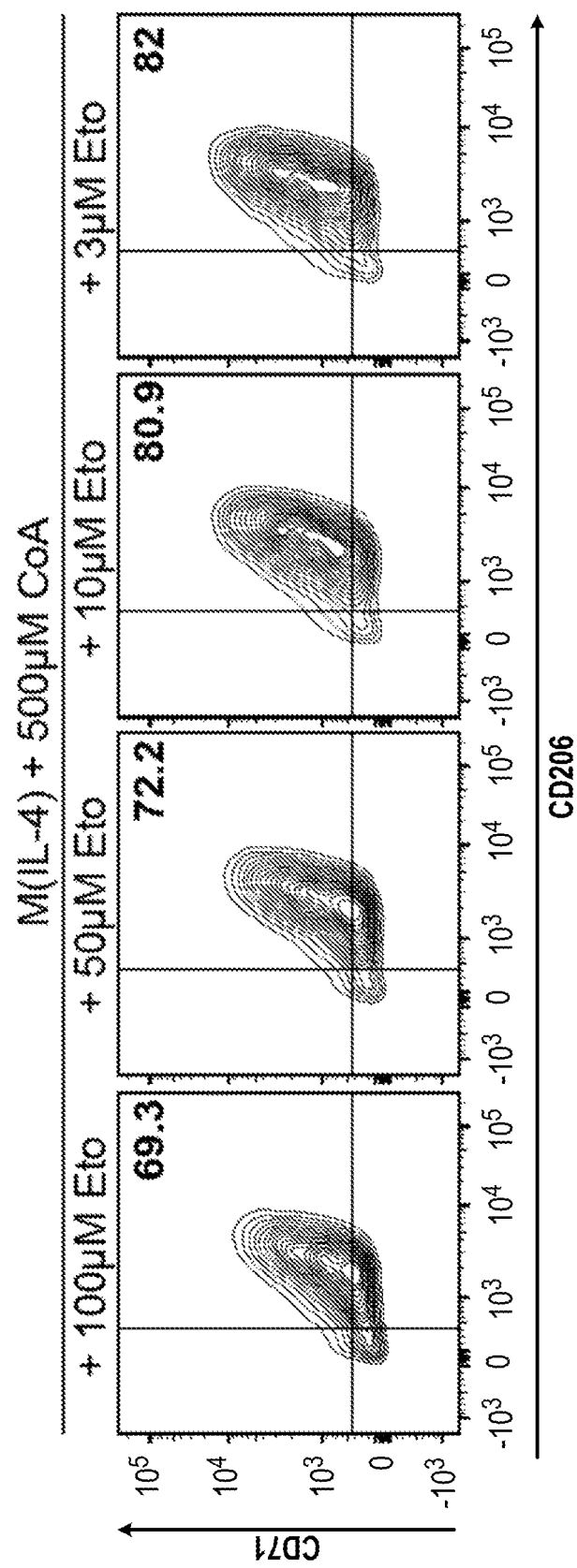
Figure 10E:
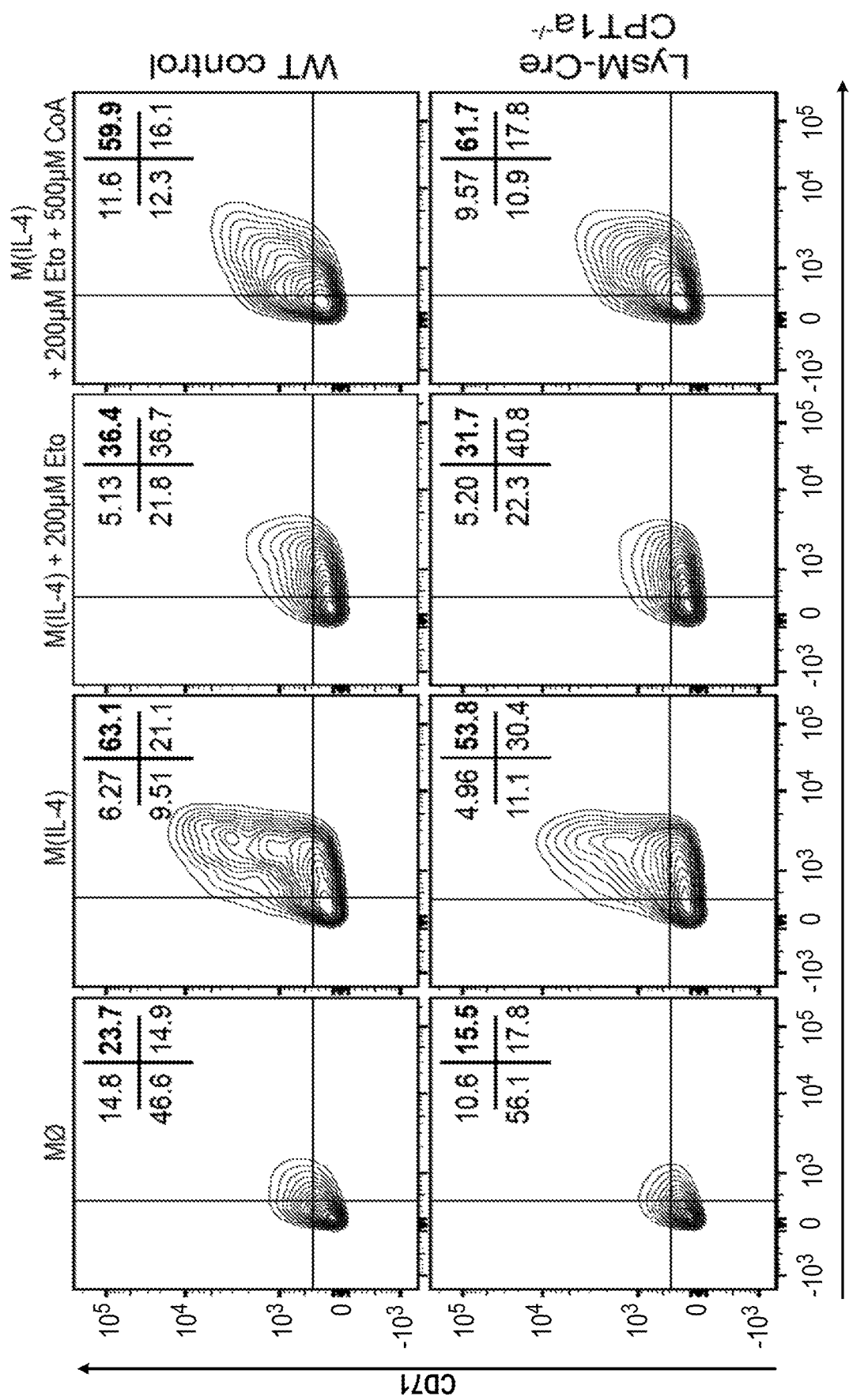

To test whether depletion of intracellular CoA is the mechanism by which etomoxir blocks M(IL-4) polarization, we measured IL-4-associated cell surface markers in response to 200 μM etomoxir with or without exogenously added CoA. As predicted, the reduction of CD206+/CD71+ cells upon etomoxir treatment can be rescued by provision of free CoA to the experimental medium (FIG. 10A, FIG. 10B). Importantly, free CoA significantly increased IL-4-induced expression of CD206 and CD71 in the absence of etomoxir, and had no effect on polarization in the absence of IL-4 (FIG. 10B). Indeed, the CD206+/CD71+ population can be adjusted as a function of the [etomoxir]:[CoA] ratio—the rescue of cell surface marker expression in the presence of 200 μM etomoxir is a concentration-dependent function of exogenously added CoA (FIG. 10A, FIG. 10C) Similarly, in the presence of 500 μM CoA, the population of CD206+/CD71+ cells can be proportionally decreased with increasing concentrations of etomoxir (FIG. 10A, FIG. 10D). CoA supplementation also did not alter basal respiration in BMDMs treated with excess etomoxir, further demonstrating that the effects of CoA are independent of the off-target effects of etomoxir on the ANT and complex I (FIG. 9B).

Figure 9D:
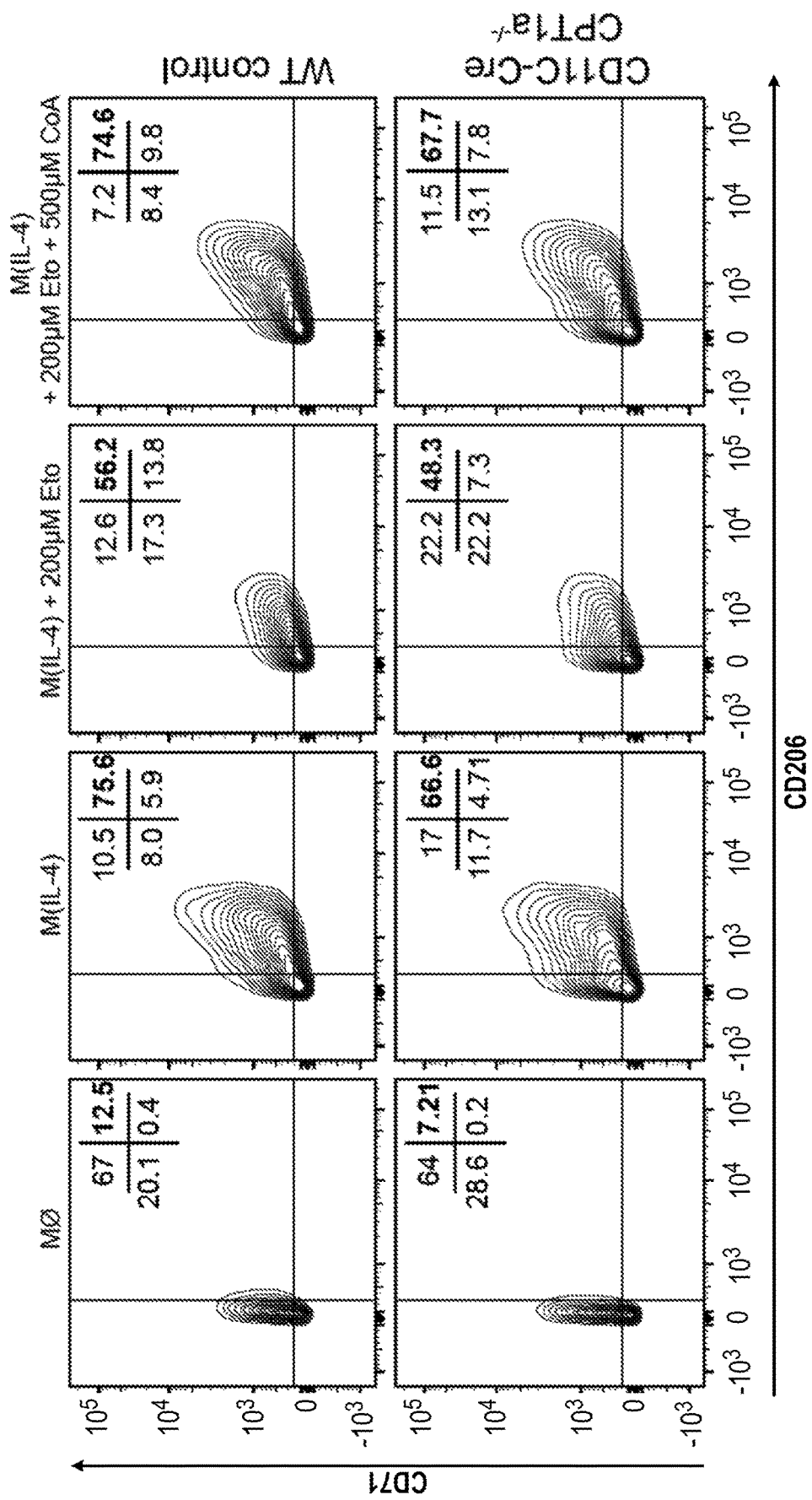

Finally, to further demonstrate that etomoxir influences macrophage polarization independently of LCFA oxidation, we measured whether CoA supplementation can overcome the effects of excess etomoxir on M(IL-4) polarization in Cpt1a−/− and Cpt2−/− cells. Indeed, the etomoxir-induced reduction in CD206+/CD71+ cells could be rescued by CoA supplementation in all three models with disrupted LCFA oxidation used in this study: LysM-Cre Cpt1a−/− (FIG. 10E), LysM-Cre Cpt2−/− (FIG. 9C), and CD11c-Cre Cpt1a−/− BMDMs (FIG. 9D). The result is consistent with our findings throughout the study demonstrating that high concentrations of etomoxir block alternative macrophage activation independently of CPT-1 and LCFA oxidation.

Detailed description of FIG. 10. Coenzyme A (CoA) rescues inhibition of M(IL-4) polarization by excess etomoxir. (FIG. 10A) Flow cytometric analysis of CD206+/CD71+ BMDMs after 24 hr treatment with 200 μM etomoxir±500 μM CoA. The data shown are from one experiment representative of a total of six independent biological replicates. (FIG. 10B) Aggregate data of the CD206+/CD71+ population in response to 200 μM etomoxir with or without 500 μM CoA. (n=6 independent biological replicates). (FIG. 10C) Flow cytometric analysis of BMDMs showing CD206+/CD71+ in the presence of 200 μM etomoxir and varying the concentration of added CoA. The data shown are from one experiment representative of a total of three independent biological replicates. (FIG. 10D) Flow cytometric analysis of CD206+/CD71+ BMDMs in the presence of 500 μM CoA and varying the etomoxir concentration between 3-100 μM etomoxir. The data shown are from one experiment representative of a total of three independent biological replicates. (FIG. 10E) Flow cytometric analysis of the CD206+/CD71+ population in WT and Cpt1a−/− BMDMs in response to IL-4±200 μM etomoxir±500 μM CoA. The data shown are from one experiment representative of a total of four independent biological replicates. See also FIG. 9.

Example 7. Increasing Intracellular CoA In Vivo Increases Alternative Macrophage Activation In a murine acute liver injury model using sterile injury or tetracycline administration, intravenous administration of coenzyme A is shown to decrease healing time and improve the extent of resolution from the injury. Increased expression of alternative liver macrophage activation biomarkers is identified on macrophages obtained from peritoneal macrophages and/or Kupffer cells.

In a murine model of Limonoids sigmodontis, a nematode infection, administration of coenzyme A is shown to reduce parasite burden and replication, proportional to the extent of the immune cell response.

Example 8. Decreasing Intracellular CoA In Vivo Decreases Alternative Macrophage Activation In a rat model of diet-induced NASH (Hui, S. T., Kurt, Z., Tuominen, I., Norheim, F., Davis, R. C., Pan, C., Dirks, D. L., Magyar, C. E., French, S. W., Chella Krishnan, K., Sabir, S., Campos-Pérez, F., Mendez-Sanchez, N., Macias-Kauffer, L., León-Mimila, P., Canizales-Quinteros, S., Yang, X., Beaven, S. W., Huertas-Vazquez, A., Lusis, A. J. The Genetic Architecture of Diet-induced Hepatic Fibrosis in Mice. Hepatology. 2018 Jun. 16. doi: 10.1002/hep.30113), intravenous administration of the pantothenate kinase inhibitor alpha-methyl-N-phenethyl-pantothenamide is shown to reduce inflammation and fibrosis in the liver. Decreased expression of alternative macrophage activation biomarkers is identified on Kupffer cells and/or myeloid-derived precursors obtained from the liver.

In a model to assess the effect of agents on suppression of tumor growth inhibition by tumor associated macrophages (TAMs) and/or myeloid-derived suppressor cells (MDSCs), administration of an agent that reduces intracellular coenzyme A levels in TAMS and/or MDSCs reduces the size and aggressiveness of the tumor.

Example 9. In Vitro Mechanism of Action of CoA

As described herein, CoA enhances anti-inflammatory macrophage activation. One possibility suggested was that depletion of intracellular CoA might limit the availability of acetyl CoA, thereby adjusting histone acetylation and IL-4-driven gene expression. It is well established epigenetic modification is associated with acquisition of the IL-4-associated phenotype and it has even been linked to metabolic changes associated with M(IL-4) activation.

Preliminary data suggests, however, that the mechanism by which CoA boosts markers of M(IL-4) may not be simply boosting acetyl CoA levels. FIG. 11 shows that CoA and acetyl CoA have different effects on cell surface markers (FIG. 11A) and gene expression (FIG. 11B) associated with IL-4. FIG. 11A shows that, in the presence of IL-4, acetyl CoA cannot reproduce the effect of CoA in increasing the number of cells positive for both CD206 and CD71. Acetyl CoA counteracts the effect of CoA suggesting regulation by the CoA:acetyl CoA ratio. FIG. 11B shows that acetyl CoA has different effects than CoA on expression of the IL-4 associated genes Arg1, Mgl2 and Fabp4. Both compounds were used at 500 μM in experiments of FIGS. 11A and 11B. The experiments suggest that addition of CoA does not adjust anti-inflammatory macrophage activation by increasing acetyl CoA levels.

Example 10. Mechanistic Distinction Between Effects of CoA Depletion on Macrophage Activation and PANK2-Associated Neuropathy Mutations in Pantothenate Kinase 2 (PANK2), a rate-setting step in CoA synthesis, are associated with debilitating childhood neuropathy. As such, agents that boost intracellular CoA levels hold promise for the treatment of this disease. Evidence suggests that PANK2 is localized to the mitochondrial matrix, and mutations are likely to cause mitochondrial dysfunction and dysfunctional energy metabolism. Indeed, many inborn errors in metabolism from mutations in mitochondrial proteins manifest as neuropathies.

However, data shows that the mechanism by which CoA boosts anti-inflammatory macrophage activation (or its depletions blunts it) is distinct from the mechanism by which CoA depletion from mutations in PANK2. Although CoA enhances cell surface marker and gene expression associated with IL-4, it does not enhance oxygen consumption (FIG. 12), an integrative marker of mitochondrial function. Further, we previously described that IL-4 polarization can proceed even in the presence of potent mitochondrial inhibitors, suggesting mitochondrial ATP production is not obligatory for (and perhaps not the driver of) the effect of Coenzyme A.

What is claimed is:

1. A method for treating diet-induced obesity, sepsis, rheumatoid arthritis, eczemas, allergic or atopic dermatitis, an inflammatory condition of the eye, or promoting tissue repair, wound healing, repair of skin damage from burns, sunburn, or radiation damage, or suppressing or treating a parasitic infection in a subject comprising administering to the subject coenzyme A.

2. The method of claim 1 wherein the coenzyme A is administered orally, parenterally, topically, intraocularly, intradermally or subcutaneously.

* * * * *